United States Patent
Angehrn et al.

(10) Patent No.: US 6,583,133 B1
(45) Date of Patent: *Jun. 24, 2003

(54) PROPENYL CEPHALOSPORIN DERIVATIVES AND PROCESS FOR THE MANUFACTURE THEREOF

(75) Inventors: Peter Angehrn, Böckten (CH); Erwin Götschi, Reinach (CH); Ingrid Heinze-Krauss, Schliengen (DE); Hans G. F. Richter, Grenzach-Wyhlen (DE)

(73) Assignee: Basilea Pharmaceutica AG, Binningen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/337,908

(22) Filed: Jun. 22, 1999

(30) Foreign Application Priority Data

Jun. 22, 1998 (EP) .............................................. 98111415
Apr. 26, 1999 (EP) .............................................. 99108149

(51) Int. Cl.⁷ .................... C07D 501/24; A61K 31/545; A61K 31/546; A61P 31/04
(52) U.S. Cl. ...................... 514/200; 514/202; 514/203; 514/204; 514/205; 540/215; 540/222; 540/224; 540/225; 540/226; 540/227; 540/229
(58) Field of Search ................................ 514/200, 202, 514/203, 204, 205; 540/215, 222, 224, 225, 226, 227, 229

(56) References Cited

U.S. PATENT DOCUMENTS

| | | | |
|---|---|---|---|
| 3,983,113 A | | 9/1976 | Beeby .................... 540/226 |
| 4,486,586 A | | 12/1984 | Narita et al. ................. 540/225 |
| 4,751,295 A | | 6/1988 | Oka et al. .................... 540/222 |
| 5,075,298 A | | 12/1991 | Aszödi et al. .............. 540/222 |
| 5,494,666 A | * | 2/1996 | Bohringer .................... 514/210 |
| 5,523,400 A | * | 6/1996 | Wei ............................. 514/202 |
| 5,804,577 A | * | 9/1998 | Hebeisen .................... 514/202 |
| 6,150,350 A | * | 11/2000 | Angehern .................... 514/202 |

FOREIGN PATENT DOCUMENTS

| | | |
|---|---|---|
| DE | 34 04615 | 8/1984 |
| DE | 35 12225 | 10/1985 |
| EP | 0 315 518 | 5/1989 |
| EP | 0 333 154 | 9/1989 |
| EP | 0 503 453 | 9/1992 |
| EP | 0 528 343 | 2/1993 |
| EP | 0 841 339 | 5/1998 |

OTHER PUBLICATIONS

P. Jeffrey et al., J. Org. Chem., vol. 47, p. 587–590 (1982).
A. Merzouk et al., Tetrahedron Letters, vol. 33, No. 4, p. 477–480 (1992).
T. Green, Protective Groups in Organic Synthesis, Chapter 5, p. 152–192 (1981).
T. Green, Protective Groups in Organic Synthesis, Chapter 7, p. 218–287 (1981).

* cited by examiner

Primary Examiner—Mark L. Berch
(74) Attorney, Agent, or Firm—George W. Johnston; Patricia S. Rocha-Tramaloni; Lyman H. Smith

(57) ABSTRACT

Disclosed are cephalosporin derivatives of the general formula

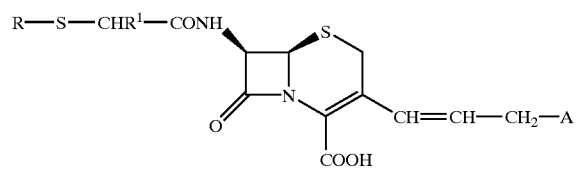

wherein R is an organic residue with a molecular weight not exceeding 400 bonded to the adjacent sulphur atom via carbon and consisting of carbon, hydrogen, and optional oxygen, sulfur, nitrogen and/or halogen atoms; $R^1$ is hydrogen, lower alkyl or phenyl; and A is a secondary, tertiary or quaternary nitrogen atom bound directly to the propenyl group and being substituted by an organic residue with a molecular weight not exceeding 400 and consisting of carbon, hydrogen, and optional oxygen, sulfur, nitrogen and/or halogen atoms, as well as readily hydrolyzable esters thereof, pharmaceutically acceptable salts of said compounds and hydrates of the compounds of formula I and of their esters and salts.

51 Claims, No Drawings

PROPENYL CEPHALOSPORIN DERIVATIVES AND PROCESS FOR THE MANUFACTURE THEREOF

FIELD OF THE INVENTION

The present invention relates to cephalosporin-type antibiotics.

BACKGROUND OF THE INVENTION

Cephalosporins are known for their antibiotic properties.

SUMMARY OF THE INVENTION

The present invention provides cephalosporin derivatives of the general formula

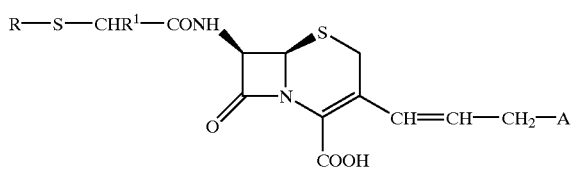

wherein R is an organic residue with a molecular weight not exceeding 400 bonded to the adjacent sulfur atom via carbon and consisting of carbon, hydrogen, and optionally oxygen, sulfur, nitrogen and/or halogen atoms; $R^1$ is hydrogen, lower alkyl or phenyl; and A is a secondary, tertiary or quaternary nitrogen atom bound directly to the propenyl group and being substituted by an organic residue with a molecular weight not exceeding 400 and consisting of carbon, hydrogen, and optionally oxygen, sulfur, nitrogen and/or halogen atoms,
as well as readily hydrolyzable esters thereof, pharmaceutically acceptable salts of said compounds and hydrates of the compounds of formula I and of their esters and salts.

DETAILED DESCRIPTION OF THE INVENTION

The compounds of the present formula I are useful in the treatment of infectious diseases in that they have potent and broad antibacterial activity; especially against Gram-positive organisms, e.g. methicillin-sensitive (MSSA) and methicillin-resistant (MRSA) staphylococci, enterococci and pneumococci.

In the above compounds of formula I the substituent in position 3 of the cephalosporin ring can be present in the E-form:

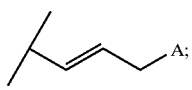

or in the Z-form:

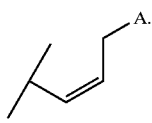

Compounds of formula I wherein the substituent in position 3 is in the E-form are generally preferred.

Compounds of formula I, in which $R^1$ is lower alkyl or phenyl, $R^1$ is attached at an asymmetric carbon atom which can have (R) or (S) configuration:

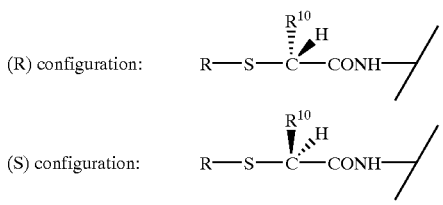

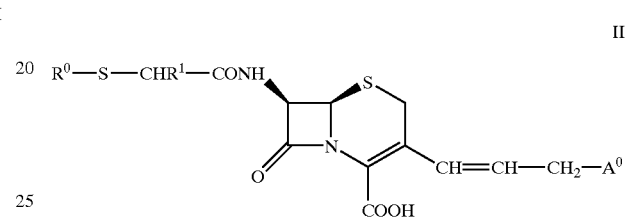

Generally, the S-form is preferred.

A subgroup of the compounds of the invention consists of compounds of the general formula

II $R^0$—S—CHR$^1$—CONH

CH=CH—CH$_2$—A$^0$

COOH wherein $R^0$ is lower alkyl or lower alkenyl, these groups being optionally substituted by one or more substituent(s) $R^7$ represented by:
halogen
lower cycloalkyl
naphthyl
optionally substituted phenyl or heterocyclyl
optionally substituted acyl
optionally etherified or acylated hydroxy
optionally acylated amino
(lower alkyl)amino, (di-lower alkyl)amino, lower cycloalkylamino
optionally esterified or amidated carboxy
etherified mercapto, lower alkylsulfinyl, phenylsulfinyl
lower alkylsulfonyl, phenylsulfonyl
cyano
amidino, (lower alkyl)amidino, (di-lower alkyl) amidino, guanidino, (lower alkyl)guanidino, (di-lower alkyl)guanidino; or $R^0$ is phenyl, naphthyl or heterocyclyl, these groups being optionally substituted by one or more substituents $R^8$ represented by:
halogen
optionally substituted lower alkyl, lower alkenyl or lower cycloalkyl
optionally substituted phenyl or heterocyclyl
optionally substituted acyl
optionally etherified or acylated hydroxy
optionally acylated amino
(lower alkyl)amino, (di-lower alkyl)amino, lower cycloalkylamino
optionally esterified or amidated carboxy
etherified mercapto, lower alkylsulfinyl, phenylsulfonyl
optionally amidated sulfonyl
lower alkylsulfonyl, phenylsulfonyl
cyano;

$A^\ominus$ is a quaternary nitrogen residue of the general formula

III

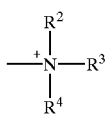

wherein $R^2$, $R^3$ and $R^4$ may be the same or different and each are alkyl cycloalkyl, alkenylalkyl or saturated heterocyclyl;

or $R^2$ and $R^3$ together with the N atom represent a saturated or partly unsaturated 5 to 8 membered heterocyclic ring or a 10 to 14 membered fused heterocyclic ring which may contain additional hetero atoms selected from oxygen, sulfur and nitrogen, $R^4$ being as above or may represent a 1–2-, 1–3- or 1–4-alkylene or a vinylene bridge to the heterocyclic ring represented by $R^2$ and $R^3$;

or $R^2$, $R^3$ and $R^4$ together with the N atom represent an aromatic 5 or 6 membered, optionally fused heterocyclic ring which may contain additional hetero atoms selected from oxygen, sulfur and nitrogen; or $A^\ominus$ is a secondary or tertiary nitrogen residue of the general formula

IV

wherein $R^5$ and $R^6$ may be the same or different and each are alkyl, cycloalkyl, alkenylalkyl or heterocyclyl or $R^5$ is hydrogen;

or $R^5$ and $R^5$ together with the N atom represent a saturated or partly unsaturated or aromatic 5 or 6 membered heterocyclic ring or a 10 to 12 membered fused heterocyclic ring which may contain additional hetero atoms selected from oxygen, sulfur and nitrogen, and wherein, where $R^2$, $R^3$, $R^4$, $R^5$ and/or $R^6$ represent alkyl, this group is optionally substituted by carbamoyloxy or one or more substituents $R^7$, wherein $R^7$ has the above meaning; and where $R^2$, $R^3$ and $R^4$ and $R^5$ and $R^6$ represent heterocyclyl or together form part of a heterocyclic ring as defined above, this heterocyclyl group/heterocyclic ring is optionally substituted by one or more substituents $R^8$, wherein $R^8$ has the above meaning, as well as readily hydrolyzable esters thereof, pharmaceutically acceptable salts of said compounds and hydrates of the compounds of formula II and of their esters and salts.

Subgroups of the compounds of formula II are as follows:
Compounds of the general formulas

IIA

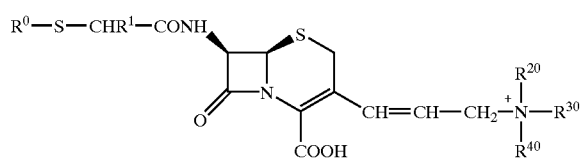

wherein $R^0$ and $R^1$ are as defined above and $R^{20}$, $R^{30}$ and $R^{40}$ may be the same or different and each are alkyl (optionally substituted by $R^7$ as for $R^2$, $R^3$ and $R^4$ above), cycloalkyl, alkenylalkyl or saturated heterocyclyl (optionally substituted by $R^8$ as for $R^2$, $R^3$ and $R^4$ above);

IIB

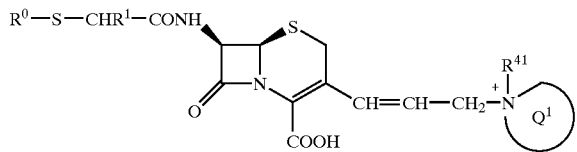

wherein $R^0$ and $R^1$ are as defined above, $Q^1$ is a saturated or partly unsaturated 5 to 8 membered heterocyclic ring or a 10 to 14 membered fused heterocyclic ring which may contain additional hetero atoms selected from oxygen, sulfur and nitrogen, and any of the ring atoms are optionally substituted by $R^8$ as for $R^2$ and $R^3$ above, and $R^{41}$ is alkyl (optionally substituted by $R^7$ as for $R^4$ above), cycloalkyl, alkenylalkyl or saturated heterocyclyl or may represent a 1–2-, 1–3- or 1–4-alkylene or a vinylene bridge to the heterocyclic ring of $Q^1$;

IIC

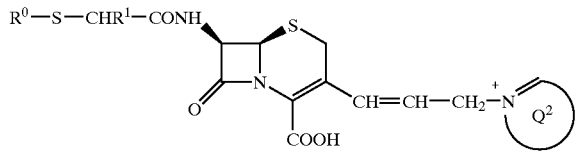

wherein $R^0$ and $R^1$ are as defined above and $Q^2$ is an aromatic 5 or 6 membered heterocyclic ring or a 10 to 12 membered fused heterocyclic ring which may contain in addition to the represented nitrogen atom hetero atoms selected from oxygen, sulfur and nitrogen, and any of the ring atoms are optionally substituted by $R^8$ as for $R^2$, $R^3$ and $R^4$ above;

IID

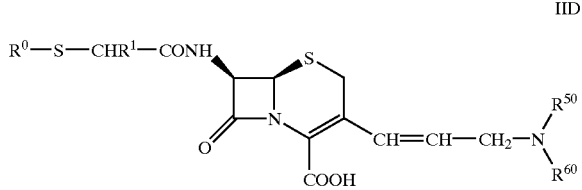

wherein $R^0$ and $R^1$ are as defined above and $R^{50}$ and $R^{60}$ may be the same or different and each are alkyl (optionally substituted by $R^7$ as for $R^5$ and $R^6$ above), cycloalkyl, alkenylalkyl or saturated heterocyclyl (optionally substituted by $R^8$ as for $R^5$ and $R^6$ above) or $R^{50}$ is hydrogen;

IIE

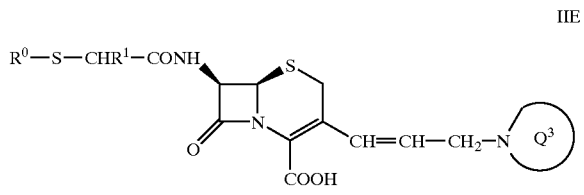

wherein $R^0$ and $R^1$ are as defined above and $Q^3$ is a saturated or partly unsaturated or aromatic 5 or 6 membered heterocyclic ring or 10 to 12 membered fused heterocyclic ring which may contain additional hetero atoms selected from oxygen, sulfur and nitrogen, and any of the ring atoms are optionally substituted by $R^8$ as for $R^5$ and $R^6$ above, as well as readily hydrolyzable esters thereof, pharmaceutically acceptable salts of said compounds and hydrates of the compounds of formulas IIA–IIE and of their esters and salts.

The term "halogen" or "halo" used herein refers to chlorine or chloro; bromine or bromo; iodine or iodo; and fluorine or fluoro, unless specified otherwise.

As used herein, the terms "alkyl" and "lower alkyl" refer to both straight and branched chain saturated hydrocarbon groups having 1 to 8, and preferably 1 to 4, carbon atoms, for example, methyl, ethyl, n-propyl, isopropyl, t-butyl and the like.

By the term "substituted lower alkyl" is meant a "lower alkyl" moiety as defined above substituted by, for example, halogen, amino, lower alkylamino, di-(lower alkyl)amino, hydroxy, lower alkoxy, cyano, carboxy, carbamoyl etc., such as carboxymethyl, carbamoylmethyl, trifluoromethyl, 2,2,2-trifluoroethyl, 2-chloroethyl, 2-hydroxyethyl, methoxymethyl, methylaminomethyl, dimethylaminoethyl and the like.

As used herein, the term "lower alkoxy" refers to a straight or branched chain hydrocarbonoxy group wherein the "alkyl" portion is a lower alkyl group as defined above. Examples include methoxy, ethoxy, n-propoxy and the like. The "alkyl" portion may be substituted as defined above.

As used herein, "alkenyl" and "lower alkenyl" refer to unsubstituted or substituted hydrocarbon chain radical having from 2 to 8 carbon atoms, preferably from 2 to 4 carbon atoms, and having at least one olefinic double bond, e.g. allyl, vinyl, 2-propenyl, 2-butenyl, 3-butenyl, 2-methyl-2-propenyl.

The expressions "alkenylalkyl" and "lower alkenylalkyl" are employed to indicate that the double bonds of said radicals are not connected with the first carbon atom (such as in vinyl and 1-propenyl), but that these radicals are limited to groups having their unsaturation in 2-, 3- and further positions. It is understood that "lower alkenylalkyl" refers to groups containing up to and including 8 carbon atoms, e.g. 2-propenyl, 2-butenyl, 3-butenyl, 2-methyl-2-propenyl.

By the term "substituted lower alkenyl" is meant a lower alkenyl moiety as defined above, preferably vinyl, substituted as for "substituted lower alkyl" but preferably substituted by cyano or by carboxy which may be amidated by amino, lower alkylamino, (di-lower alkyl)-amino or by the amino group of a natural α-amino acid such as glycine, alanine or phenylalanine.

By the term "cycloalkyl" or "lower cycloalkyl" is meant a 3–7 membered saturated carbocyclic moiety, e.g., cyclopropyl, cyclobutyl, cyclohexyl, etc.

By the term "substituted lower cycloalkyl" is meant a lower cycloalkyl moiety as defined above substituted by, for example, lower alkyl, halogen, amino, lower alkylamino, di-(lower alkyl)amino, hydroxy, lower alkoxy, cyano, carboxy etc., such as 3-hydroxy-cyclobutyl, 4-methyl-cyclohexyl or 3,4-dimethoxy-cyclopentyl.

"Acyl" alone or in combination with other groups such as in "acylamino", is preferably derived from a carboxylic acid and is thus e.g. lower alkanoyl, e.g. formyl, acetyl, propionyl, isobutyryl, pivaloyl; lower cycloalkanoyl, e.g. cyclopropylcarbonyl; benzoyl.

By the term "aryl" is meant a radical derived from an aromatic hydrocarbon by the elimination of one atom of hydrogen and it can be substituted or unsubstituted. The aromatic hydrocarbon can be mononuclear or polynuclear. Examples of aryl include phenyl, naphthyl, anthryl, phenanthryl and the like. The aryl group can have at least one substituent selected from, as for example, halogen, hydroxy, cyano, carboxy, nitro, amino, dimethylamino, lower alkyl, lower alkoxy, carbamoyl, such as in tolyl, xylyl, mesityl, cumenyl, 2,4-difluorophenyl, 4-carboxyphenyl, 4-nitrophenyl, 4-dimethyl-aminophenyl, 4-methoxyphenyl, 2,4,5-trichlorophenyl and 6-carboxy-2-naphthyl.

As used herein, the term "lower alkylamino and di-lower alkylamino" refers to mono and dialkylamino residues wherein lower alkyl is as defined above, for example methylamino, 2-ethylamino, N-methylamino, N-ethylamino, N,N-dimethylamino, N,N-diethylamino and the like. The terms (lower alkyl)amidino, (di-lower alkyl) amidino, (lower alkyl)guanidino, (di-lower alkyl)guanidino are defined in analogous manner.

As used herein "heterocyclyl" or "heterocyclic ring" refers to an unsaturated or saturated, unsubstituted or substituted 4-, 5-, 6-, 7- or 8-membered heterocyclic ring. Unsaturated heterocyclic rings may be partly unsaturated or aromatic. The heterocyclic ring contains at least one hetero atom selected from the group consisting of oxygen, nitrogen, or sulfur. Exemplary heterocyclic rings include, but are not limited to, for example, the following groups: azetidinyl, pyridyl, pyrazinyl, piperidyl, morpholinyl, pyrimidyl, piperazinyl, pyrrolidinyl, pyridazinyl, pyrazolyl, triazinyl, imidazolyl, thiazolyl, 1,2,3-thiadiazolyl, 1,2,4-thiadiazolyl, 1,2,4-oxadiazolyl, 1,3,4-oxadiazolyl, 1,2,3-triazolyl, 1,2,4-triazolyl, 1H-tetrazolyl, 2H-tetrazolyl; furyl, 1H-azepinyl, thiophenyl, isoxazolyl, isothiazolyl, oxazolidinyl, etc. Substituents for the heterocyclic ring include, for example, optionally hydroxy substituted lower alkyls such as methyl, ethyl, propyl, hydroxypropyl, etc., lower alkoxys such as methoxy, ethoxy, etc., halogens such as fluorine, chlorine, bromine, etc., halogen substituted alkyls such as trifluoromethyl, trichloroethyl, etc., amino, mercapto, hydroxyl, carbamoyl, or carboxyl groups. A further substituent is oxo, such as in 2-oxo-oxazolidin-3-yl, 1,1-dioxo-tetrahydrothiophen-3-yl. Further examples of substituted heterocycles are 6-methoxy-pyridin-3-yl, 5-methyl-isoxazol-3-yl, 2-methylpyridinyl, 3-hydroxypyridinyl, 4-[4-(3-hydroxy-propyl)]-pyridinyl, 1-methylpyrrolidinyl, 4-methyl-morpholinyl and 4-ethoxycarbonyl-5-methyl-thiazolyl.

The terms "heterocyclyl" or "heterocyclic ring" may also mean a "fused heterocyclic ring". By the expression "fused heterocyclic ring" utilized hereinabove is meant a heterocyclic ring fused e.g. to a second carbocylic or heterocyclic 5- or 6-membered saturated or unsaturated ring forming a bicyclic saturated, partly unsaturated or aromatic ring system containing at least 1 heteroatom selected from oxygen, nitrogen and sulfur. Exemplary of fused heterocyclic rings include, but are not limited to, for example the following groups: 1-quinolinyl, 2-quinolinyl, benzimidazolyl, benzoxazolyl, benzothiazolyl, 1-quinuclidinyl(1-azonia-bicyclo[2,2,2]oct-1-yl), 3-hydroxy-quinuclidinyl, dehydroquinuclidinyl, 1,5-diazabicyclo[3.3.0]octanyl, 1,4-diazabicyclo[2.2.2]octanyl(4-aza-bicyclo[2,2,2]oct-1-yl), 4-aza-1-azonia-bicyclo[2,2,2]oct-1-yl, 1-aza-5-methyl-4,6-dioxabicyclo-[3.3.1]nonanyl, 2,3,4,6,7,8,9,10-octahydro-pyrimido[1,2-a]azepin-1-yl and the like. The heterocyclic rings falling under $Q^1$ and $Q^2$ in formulas IIB and IIC above are quaternary, i.e. the above examples for heterocyclic rings apply also to their quaternary forms, e.g. 1-methyl-pyrrolidin-1-ium (in formula IIB), pyridin-1-ium (in formula IIC).

By the term "hetero atom" is meant an atom selected from the group consisting of oxygen, nitrogen and sulfur.

By the term "substituted phenyl" is meant phenyl mono, di- or tri-substituted by halogen, optionally substituted lower alkyl, optionally protected hydroxy, cyano, hydroxy or carbamoyl.

As readily hydrolyzable esters of the compounds of formula I there are to be understood compounds of formula I, the carboxy group(s) of which (for example the 2-carboxy group) is/are present in the form of readily hydrolyzable ester groups. Examples of such esters, which can be of the conventional type, are the lower alkanoyloxy-alkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyl-oxymethyl, 1-ethoxycarbonyloxy-ethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used. Other examples of such esters are the following: (2,2-dimethyl-1-oxopropoxy)methyl ester; 2-[(2-methylpropoxy)carbonyl]-2-pentenyl ester; 1-[[(1-methylethoxy)carbonyl]oxy]ethyl ester; (5-methyl-2-oxo-1,3-dioxol-4-yl) methyl ester; 1-[[(cyclohexyloxy)carbonyl]oxy]ethyl ester; and 3,3-dimethyl-2-oxobutyl ester. It will be appreciated by those of ordinary skill in the art that the readily hydrolyzable esters of the compounds of the present invention can be formed at a free carboxy group of the compound.

As used herein pharmaceutically acceptable salts useful in this invention include base addition salts derived from metals, the ammonio salt or quaternary ammonio salts derived from organic bases or, preferably, acid addition salts derived from inorganic or organic acids. Examples of preferred metal salts are those derived from the alkali metals, for example, sodium. Examples of quaternary ammonio salts derived from organic bases include tetramethylammonio, tetraethylammonio and the like. These salts derived from amines include salts with N-ethylpiperidine, procaine, dibenzylamine, N,N'-dibenzylethylenediamine, alkylamines or dialkylamines as well as salts with amino acids such as, for example, salts with arginine or lysine. Especially preferred are hydrochlorides, chlorides, sulfates, phosphates, lactates, mesylates and the inner salts.

The compounds of formula I as well as their salts and readily hydrolyzable esters can be hydrated. The hydration can be effected in the course of the manufacturing process or can occur gradually as a result of hygroscopic properties of an initially anhydrous product.

The term "amino protecting groups" refers to protecting groups conventionally used to replace an acidic proton of an amino group. Examples of such groups are described in Green, T., Protective Groups in Organic Synthesis, Chapter 7, John Wiley and Sons, Inc. (1981), pp. 218–287, herein incorporated by reference. These examples include carbamates, e.g fluorenylmethyl, 2,2,2-trichloroethyl, 2-haloethyl, 2-(trimethylsilanyl)ethyl, t-butyl, allyl, benzyl. Further protecting groups are 3,5-dimethoxybenzyl, p-nitrobenzyl, diphenylmethyl, triphenylmethyl, benzyl, formyl, acetyl, phenylacetyl, trifluoroacetyl, chloro-acetyl, cyclic imides of N-phthaloyl, N-trimethylsilanyl, N-benzenesulfonyl, N-toluenesulfonyl, N-p-methylbenzylsulfonyl. Preferred is BOC [t-butoxycarbonyl, other name (1,1-dimethylethoxy)-carbonyl], benzyloxycarbonyl and allyloxycarbonyl.

The term "carboxylic acid protecting group" refers to protecting groups conventionally used to replace the acidic proton of a carboxylic acid. Examples of such groups are described in Greene, T., Protective Groups in Organic Synthesis, Chapter 5, pp. 152–192 (John Wiley and Sons, Inc. 1981), incorporated herein by reference. Preferably these examples include methoxymethyl, methylthiomethyl, 2,2,2-trichloroethyl, 2-haloethyl, 2-(trimethylsilanyl)ethyl, t-butyl, allyl, benzyl, triphenylmethyl (trityl), benzhydryl, p-nitrobenzyl, p-methoxybenzyl, trimethylsilanyl, triethylsilanyl, t-butyldimethylsilanyl, i-propyl-dimethylsilanyl. Preferred are benzhydryl, t-butyl, p-nitrobenzyl, p-methoxybenzyl and allyl.

The term "hydroxy protecting group" refers to protecting groups as conventionally used in the art such as trimethylsilanyl, t-butyl-dimethylsilanyl, dimethylphenylsilanyl, triphenylmethyl, lower alkanoyl, acetyl, tetrahydropyranyl, benzyl, p-nitrobenzyl or t-butyloxycarbonyl.

More specific embodiments of $R^7$ and $R^8$ in Formulas II and IIA–IIE are as follows:

$R^8$ when substituted lower alkyl, lower alkenyl or lower cycloalkyl is substituted by hydroxy, lower alkoxy, cyano, carboxy, amino, lower alkylamino, di-(lower alkyl)amino, carbamoyl, carbamoyloxy or 1–3 halogens. Substituted lower alkenyl is preferably vinyl and is preferably substituted by cyano or by carboxy which may be amidated by amino, lower alkylamino, (di-lower alkyl)-amino or by the amino group of a natural α-amino acid such as glycine, alanine or phenylalanine.

The carboxy group optionally present on lower alkyl, lower alkenyl or lower cycloalkyl $R^8$ can be esterified or amidated quite in the same way as indicated below for esterified and amidated carboxy values $R^7$ or $R^8$. Preferably, $R^8$ is esterified or amidated carboxymethyl, e.g. ethoxycarbonylmethyl, hydroxyethylcarbamoylmethyl, hydroxyethoxyethylcarbamoylmethyl.

$R^7$ or $R^8$ when substituted phenyl are substituted by 1–3 halogens, lower alkoxy, cyano, hydroxy or carbamoyl.

$R^7$ or $R^8$ when optionally substituted heterocyclyl is a saturated or unsaturated 5 to 6 membered heterocyclic ring which may contain additional heteroatoms selected from oxygen, sulfur and nitrogen and is optionally substituted by hydroxy, halogen, lower alkoxy, carboxy, amino, lower alkylamino, di-(lower alkyl)amino, cyano or oxo.

$R^7$ or $R^8$ when optionally substituted acyl is lower alkanoyl, lower cycloalkanoyl or benzoyl optionally substituted by 1–3 halogens, hydroxy, lower alkoxy, amino, lower alkylamino, di-(lower alkyl)amino, carbamoyl, carbamoyloxy, cyano or phenyl.

$R^7$ or $R^8$ when etherified hydroxy is lower alkoxy, lower cycloalkoxy or phenoxy, each optionally substituted by 1–3 halogens, amino, hydroxy, methoxy, carbamoyloxy, carboxy or carbamoyl.

$R^7$ or $R^8$. when acylated hydroxy is lower alkanoyloxy, benzoyloxy, heterocyclyl-carbonyloxy or lower alkoxycarbonyloxy, each optionally substituted by amino, (lower alkyl)amino, (di-lower alkyl)amino, carboxy, carbamoyl, carbamoyloxy or 1–3 halogen atoms.

$R^7$ or $R^8$ when acylated amino is lower alkanoylamino, lower cycloalkylamino, benzoylamino, heterocyclyl-carbonylamino or lower alkoxycarbonylamino, each optionally substituted by amino, (lower alkyl)amino, (di-lower alkyl)amino, hydroxy, methoxy, carboxy, carbamoyl, carbamoyloxy or 1–3 halogen atoms.

$R^7$ or $R^8$ when esterified carboxy is lower alkoxycarbonyl, cycloalkoxycarbonyl, phenoxycarbonyl, phenyl-lower alkoxycarbonyl, each optionally substituted by amino, (lower alkyl)amino, (di-lower alkyl)amino, methoxy, carboxy, carbamoyl, carbamoyloxy or 1–3 halogen atoms.

$R^7$ or $R^8$ when amidated carboxy is carbamoyl, lower alkylcarbamoyl, (di-lower alkyl)carbamoyl or lower cycloalkylcarbamoyl, each optionally substituted by amino, (lower alkyl)amino, (di-lower alkyl)amino, carboxy, carbamoyl, carbamoyloxy or 1–3 halogen atoms.

$R^8$ when substituted lower alkylcarbamoyl or lower cycloalkylcarbamoyl is substituted by hydroxy, lower alkoxy, hydroxy-lower alkoxy, amidino, (lower alkyl) amidino, (di-lower alkyl)amidino, guanidino, (lower alkyl) guanidino, (di-lower alkyl)guanidino or heterocyclyl. "Amidino" above is attached at either of its 1-, 2- or 3-position "Guanidino" is attached at either of its two possible isomeric positions.

$R^7$ or $R^8$ when etherified mercapto is lower alkylthio, lower cycloalkylthio or phenylthio, each optionally substituted by amino, (lower alkyl)amino, (di-lower alkyl)amino, hydroxy, methoxy, carboxy, carbamoyl, carbamoyloxy or 1–3 halogen atoms.

$R^7$ or $R^8$ when amidated sulfonyl is lower alkyl-aminosulfonyl, lower or cycloalkyl-aminosulfonyl, each optionally substituted by amino, (lower alkyl)amino, (di-lower alkyl)amino, hydroxy, methoxy, carboxy, carbamoyl, carbamoyloxy or 1–3 halogen atoms.

The rings $Q^1$, $Q^2$ and $Q^3$ in Formulas IIB, IIC and IIE may be unsubstituted or substituted by one or more substituents $R^8$ as disclosed above.

Preferred embodiments of $R/R^0$ in Formulas I, II and IIA–IIE are as follows:

optionally substituted phenyl, e.g. phenyl, 2,4,5-trichlorophenyl, 3,4-dichlorophenyl, 2,5-dichlorophenyl, 4-hydroxymethylphenyl or 3,5-dimethylphenyl;

optionally substituted naphthyl e.g. 2-naphthyl, 6-carboxy-2-naphthyl;

optionally substituted heterocyclyl, e.g., 2-benzooxazolyl, 2-benzothiazolyl or 4-pyridinyl;

Preferred embodiments of $A/A^0$ in formulas I, II and IIA–IIE are as follows:

a group of formula

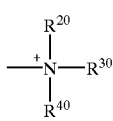

IIIA wherein $R^{20}$, $R^{30}$ and $R^{40}$ are as defined above, e.g. where $A/A^0$ is trimethyl-ammonio or carbamoylmethyl-dimethyl-ammonio; or dimethyl-(2-hydroxyalkyl)-ammonio, (2-hydroxy-1-hydroxymethyl-ethyl)-dimethyl-ammonio, bis-(2-hydroxy-ethyl)-methyl-ammonio; or a group of formula

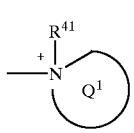

IIIB wherein $Q^1$ and $R^{41}$ are as defined above, e.g. where $A/A^0$ is-1-methyl-pyrrolidin-1-ium or 4-methyl-morpholin-4-ium; 4-aza-1-azonia-bicyclo[2,2,2]oct-1-yl or 1-azonia-bicyclo[2,2,2]oct-1-yl; or a group of formula

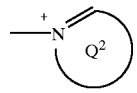

IIIC wherein $Q^2$ is as defined above, e.g. where $A/A^0$ is pyridin-1-ium, 2-methyl-pyridin-1-ium, 4-carbamoyl-pyridin-1-ium or quinolin-1-ium;

a group of formula

IIID wherein $R^{50}$ and $R^{60}$ are as defined above, e.g. where $A/A^0$ is dimethylamino or methylcyclopropylamino;

group of formula

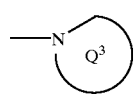

IIIE wherein $Q^3$ is as defined above, e.g. where $A/A^0$ is benzoimidazol-1-yl, pyrrolidin-1-yl, 4-hydroxy-piperidin-1-yl.

Preferred compounds of formula I are:

(E)-(6R,7R)-8-Oxo-7-(2-phenylsulfanyl-acetylamino)-3-(3-pyridin-1-ium-1-yl-propenyl)-5-thia-1-aza-bicyclo[4.2.0]oct-2-ene-2-carboxylate (E)-(6R,7R)-7-[2-(5-Ethoxycarbonyl-4-methyl-thiazol-2-ylsulfanyl)-acetylamino]-8-oxo-3-(3-pyridin-1-ium-1-yl-propenyl)-5-thia-1-aza-bicyclo[4.2.0]oct-2-ene-2-carboxylate (E)-(6R,7R)-3-[3-(2-Methyl-pyridin-1-ium-1-yl)-propenyl]-7-[2-(naphthalen-2-ylsulfanyl)-acetylamino]-8-oxo-5-thia-1-aza-bicyclo[4.2.0]oct-2-ene-2-carboxylate (E)-(6R,7R)-3-[3-(2-Methyl-pyridin-1-ium-1-yl)-propenyl]-8-oxo-7-(2-phenylsulfanyl-acetylamino)-5-thia-1-aza-bicyclo[4.2.0]oct-2-ene-2-carboxylate (E)-(6R,7R)-3-[3-(3-Hydroxy-pyridin-1-ium-1-yl)-propenyl]-8-oxo-7-(2-phenylsulfanyl-acetylamino)-5-thia-1-aza-bicyclo[4.2.0]oct-2-ene-2-carboxylate (E)-(6R,7R)-8-Oxo-7-[2-phenylsulfanyl)-acetylamino]-3-(3-quinolin-1-ium-1-yl-propenyl)-5-thia-1-aza-bicyclo[4.2.0]oct-2-ene-2-carboxylate (E)-(6R,7R)-3-[3-(1-Methyl-pyrrolidin-1-ium-1-yl)-propenyl]-8-oxo-7-(2-phenylsulfanyl-acetylamino)-5-thia-1-aza-bicyclo[4.2.0]oct-2-ene-2-carboxylate and (E)-(6R,7R)-7-[2-(Naphthalen-2-ylsulfanyl)-acetylamino]-8-oxo-3-(3-trimethylammonio-propenyl)-5-thia-1-aza-bicyclo[4.2.0]oct-2-ene-2-carboxylate.

Especially preferred compounds of formula I are:

(E)-(6R,7R)-7-[2-(Benzothiazol-2-ylsulfanyl)-acetylamino]-8-oxo-3-(3-pyridin-1-ium-yl-propenyl)-5-thia-1-aza-bicyclo[4.2.0]oct-2-ene-2-carboxylate (E)-(6R,7R)-8-Oxo-3-(3-pyridin-1-ium-1-yl-propenyl)-7-[2-(2,4,5-trichlorophenylsulfanyl)-acetylamino]-5-thia-1-aza-bicyclo[4.2.0]oct-2-ene-2-carboxylate (E)-(6R,7R)-3-[3-(3-Hydroxy-pyridin-1-ium-1-yl)-propenyl]-7-[2-(naphtalen-2-ylsulfanyl)-acetylamino]-8-oxo-5-thia-1-aza-bicyclo[4.2.0]oct-2-ene-2-carboxylate (E)-(6R,7R)-7-[2-(Naphthalen-2-ylsulfanyl)-acetylamino]-8-oxo-3-(3-quinolin-1-ium-1-yl-propenyl)-5-thia-1-aza-bicyclo[4.2.0]oct-2-ene-2-carboxylate (E)-(6R,7R)-3-[3-(1-Methyl-pyrrolidin-1-ium-1-yl)-propenyl]-7-[2-(naphtalen-2-ylsulfanyl)-acetylamino-8-oxo-5-thia-1-aza-bicyclo[4.2.0]oct-2-ene-2-carboxylate (E)-(6R,7R)-3-[3-(Carbamoylmethyl-dimethyl-ammonio)-propenyl]-7-[2-(naphtalen-2-ylsulfanyl)-acetylamino]-8-oxo-5-thia-1-aza-bicyclo[4.2.0]oct-2-ene-2-carboxylate (E)-(6R,7R)-7-[2-(Naphthalen-2-ylsulfanyl)-acetylamino]-8-oxo-3-[3-pyridin-1-ium-1-yl-propenyl]-5-thia-1-aza-bicyclo[4.2.0]oct-2-ene-2-carboxylate (E)-(6R,7R)-3-[3-[Dimethyl-(2-hydroxy-ethyl)-ammonio]-propenyl]-7-[2-(benzothiazol-2-ylsulfanyl)-acetylamino]-8-oxo-5-thias1-aza-bicyclo[4.2.0]oct-2-ene-2-carboxylate (E)-(6R,7R)-3-[3-(4-Aza-1-azonia-bicyclo[2,2,2]octan-1-yl)-propenyl]-7-[2-(naphthalen-2-ylsulfanyl)-acetylamino]-8-oxo-5-thia-1-aza-bicyclo[4.2.0]oct-2-ene-2-carboxylate (E)-(6R,7R)-3-[3-[(3-Hydroxy-propyl)-dimethyl-ammonio]-propenyl]-7-[2-(naphthalen-2-ylsulfanyl)-acetylamino]-8-oxo-5-thia-1-aza-bicyclo[4.2.0]oct-2-ene-2-carboxylate (E)-(6R,7R)-3-[3-[(2-Hydroxy-1-hydroxymethyl-ethyl)-dimethyl-ammonio]-propenyl]-2-[2-(naphthalen-2-ylsulfanyl)-acetylamino]-8-oxo-5-thia-1-aza-bicyclo[4.2.0]oct-2-ene-2-carboxylate (E)-(6R,7R)-7-[2-(Benzothiazol-2-ylsulfanyl)-acetylamino]-8-oxo-3-[3-[(2-hydroxy-1-hydroxymethyl-ethyl)-dimethyl-ammonio]-propenyl]-5-thia-1-aza-bicyclo[4.2.0]oct-2-ene-2-carboxylate (E)-(6R,7R)-3-[3-[Bis-(2-hydroxy-ethyl)-dimethyl-ammonio]-propenyl]-7-[2-(3,5-dimethyl-phenylsulfanyl)-acetylamino]-8-oxo-5-thia-1-aza-bicyclo[4.2.0]oct-2-ene-2-carboxylate (E)-(6R,7R)-3-[3-Carbamoylmethyl-dimethyl-ammonio]-propenyl]-7-[2-(6-carboxy-naphthalen-2-ylsulfanyl)-acetylamino]-8-oxo-5-thia-1-aza-bicyclo[4.2.0]oct-2-ene-2-carboxylate and (E)-(6R,7R)-7-[2-(Benzothiazol-2-ylsulfanyl)-acetylamino]-8-oxo-3-[3-(1-carboxylatomethyl)-1,4-diazonia-bicyclo[2.2.2]octan-4-yl)-propenyl]-5-thia-1-aza-bicyclo[4.2.0]oct-2-ene-2-carboxylate.

The compounds of the present invention are useful as antibiotics having potent and broad antibacterial activity; especially against Gram-positive organisms, e.g. methicillin-sensitive (MSSA) and methicillin-resistant (MRSA) staphylococci, enterococci and pneumococci.

The products in accordance with the invention can be used as medicaments, e.g. in the form of pharmaceutical preparations which contain them or their salts in admixture with a pharmaceutical, organic or inorganic inert carrier material which is suitable for parenteral or enteral, e.g. oral, administration, such as e.g. water, gelatine, gum arabic, lactose, starch, magnesium stearate, talc, vegetable oils, polyalkylene glycols, Vaseline, etc. The pharmaceutical preparations can be present in solid form, e.g. as tablets, dragees, suppositories, capsules; or in liquid form, e.g. as solutions, suspensions or emulsions. They may be sterilized and/or may contain adjuvants such as preservatives, stabilizers, wetting agents or emulsifiers, salts for varying the osmotic pressure, anaesthetics or buffers. They come into consideration for parenteral administration and also for enteral administration.

Depending on the nature of the pharmacologically active compound the pharmaceutical preparations can contain the compound for the prevention and treatment of infectious diseases in mammals, human and non-human. A daily dosage of about 10 mg to about 4000 mg, especially about 100 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg and 2000 mg can be contemplated.

Representative compounds of the present invention were tested. In vitro activity was determined by minimum inhibitory concentration in a microorganism spectrum by the agar dilution method in Mueller Hinton agar, inoculum=$10^4$ CFU/spot.

The following shows the minimum inhibitory concentrations (MIC; $\mu$g/ml) against a series of pathogenic microorganisms of some representative compounds of formula I.

| Organism | MIC [$\mu$g/ml] Compounds of Example No. | | | | | | | |
|---|---|---|---|---|---|---|---|---|
|  | 2 | 6 | 7 | 9 | 13 | 15 | 19 | 22 |
| S. aureus 6538 (MSSA) | <0.1 | <0.1 | <0.1 | <0.1 | <0.1 | <0.1 | <0.1 | <0.1 |
| S. aureus 270A (MRSA) | 2 | 1 | 2 | 2 | 1 | 2 | 1 | 1 |
| E. faecalis 6 | 2 | 0.25 | 1 | 0.5 | 0.25 | 0.5 | 0.5 | 0.5 |
| S. pneumoniae 907 | <0.1 | <0.1 | <0.1 | <0.1 | <0.1 | <0.1 | <0.1 | <0.1 |
|  | 41 | 59 | 62 | 66 | 67 | 69 | 99 | 112 |
| S. aureus 6538 (MSSA) | <0.1 | <0.1 | <0.1 | <0.1 | <0.1 | <0.1 | <0.1 | <0.1 |
| S. aureus 270A (MRSA) | 4 | 2 | 2 | 2 | 2 | 4 | 2 | 4 |
| E. faecalis 6 | 1 | 2 | 1 | 0.5 | 1 | 2 | 4 | 2 |
| S. pneumoniae 907 | <0.1 | <0.1 | <0.1 | <0.1 | <0.1 | <0.1 | <0.1 | <0.1 |

Furthermore, it has been found that the combination of compounds of formula I with β-lactamase inhibitors or carbapenems leads to a synergistic effect that further improves the antibacterial activity against Gram-positive and Gram-negative bacteria. Therefore, compounds I can optionally be combined with β-lactamase inhibitors or carbapenems.

The ratio of the two components of such a combination can be widely varied from about 1:20 to 20:1.

For example, the combination with carbapenem antibiotics such as imipenem, or with β-lactamase-inhibitors such as (Z)-(2S,3S,5R)-3-(2-cyanoethenyl)-3-methyl-4,4,7-trioxo-4-thia-1-aza-bicyclo[3.2.0]heptane-2-carboxylic acid (below named "compound X"), enhances the antibacterial activity of compounds I against highly resistant strains of Graem-positive bacterias, e.g. methicillin-resistant strains of Staphylococcus aureus.

In the following this synergism is demonstrated by the effect of imipenem and compound X on the minimum inhibitory concentrations (MIC; μg/ml) of representative compounds I against methicillin-resistant strains of Staphylococcus aureus (MRSA)

| Compound I alone or in Combination with Imipenem or with compound X | MIC (μg/ml) against MRSA* | |
|---|---|---|
| | S. aureus 42080 | S. aureus SPO-19 |
| Imipenem | >16 | >16 |
| Compound of Example 22 | 4 | 4 |
| Compound of Example 22 + Imipenem (4 μg/ml) | 1 | 1 |
| Compound of Example 22 + Compound X (μg/ml) | 1 | 0.5 |
| Compound of Example 6 | 8 | 4 |
| Compound of Example 6 + Imipenem (4 μg/ml) | 1 | 0.5 |
| Compound of Example 59 | 4 | 4 |
| Compound of Example 59 + Imipenem (4 μg/ml) | 2 | 1 |
| Compound of Example 62 | 4 | 2 |
| Compound of Example 62 + Imipenem (4 μg/ml) | 2 | 1 |

*Agar dilution method on Mueller-Hinton agar, inoculum: 10⁵ CFU/spot

The compounds of the formula I in accordance with the invention as well as their pharmaceutical acceptable salts, hydrates, or readily hydrolyzable esters can be manufactured in accordance with the invention by (a) treating a compound having the formula

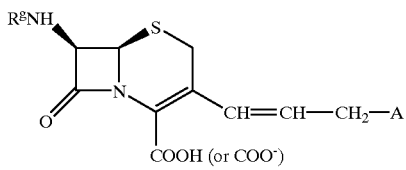

V

in which
A is as defined above and
$R^g$ is hydrogen or a silanyl protecting group;
or an ester or salt thereof with a carboxylic acid of the general formula

R—S—CHR¹—COOH      VI in which R and R¹ are as defined above,
or a reactive derivative thereof; or (b) treating a compound having the general formula

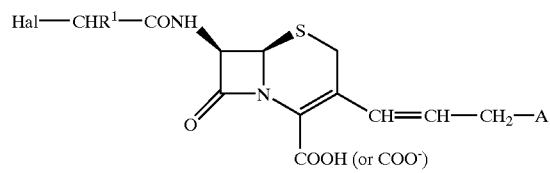

VII in which $R^1$ and A are as defined above and Hal is halogen,
or an ester or salt thereof with a thiol of formula R—SH or a salt thereof in the presence of a base; or (c) treating a compound having the formula

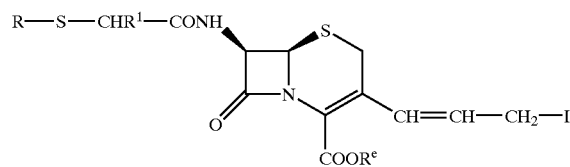

VIII in which R and $R^1$ are as defined above and $R^e$ is a carboxy protecting group, with a nitrogen nucleophile yielding the group A wherein A has the above meaning and splitting off the carboxy protecting group $R^e$; or (d) for the manufacture of compounds of formula I, in which A is a group of the formula NH—$R^6$, treating a compound having the formula VIII with a Schiff base of the general formula

Z—CH=N—R⁶      IX in which $R^6$ is as above and Z is the residue of an aldehyde ZCHO, in which Z is
alkyl, aryl or heterocyclyl, preferably phenyl, and subjecting the reaction product to hydrolysis or alcoholysis; or (e) for the manufacture of a compound of formula I in which R and/or A may contain free amino, hydroxy or carboxylic group(s) cleaving off the amino, hydroxy and/or carboxy protecting group(s) in a compound having the formula

X

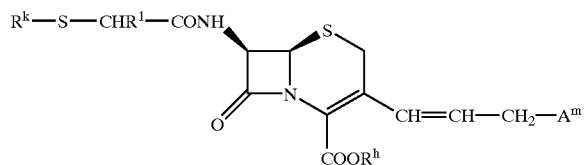

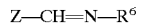

in which $R^1$ is as defined above, $R^h$ is hydrogen or a carboxy protecting group, $R^k$ is as R above and $A^m$ is as A above with the proviso that at least one of the following provisions is fulfilled:
(i) $R^h$ is a carboxylic acid protecting group,
(ii) $R^k$ is a residue defined under R having protected amino, protected hydroxy and/or protected carboxylic group(s);

(iii) $A^m$ is a residue defined under A having protected amino, protected hydroxy and/or protected carboxylic group(s);
or a salt thereof, or (f) for the manufacture of a readily hydrolyzable ester of a compound of formula I subjecting a carboxylic acid of formula I to a corresponding esterification, or (g) for the manufacture of salts or hydrates of a compound of formula I or hydrates of said salts converting a compound of formula I into a salt or hydrate or into a hydrate of said salts.

The reaction of a compound of formula V according to embodiment (a) with a compound of formula VI, or a reactive derivative thereof can be carried out in a manner known per se. A compound of formula V can be reacted in the form of a neutral inner salt formed between A and the carboxy group, or optionally, in the form of a mono- or di-addition salt with an organic or an inorganic acid, e.g. a bis-trifluoroacetate, a mono- or dihydrochloride, a mono- or dihydroiodide, or in the form of an ammonio salt with an organic amine, e.g. a trialkylammonio salt.

However, the carboxy group (or groups) in compounds of formula V and/or optionally present in compounds of formula VI (carboxy groups optionally present in R) can be protected intermediately or in situ, for example, by esterification to form readily cleavable esters such as a silanyl ester (e.g. trimethylsilanylester), a p-methoxy-benzylester or benzhydryl ester.

Furthermore, the amino groups optionally present in the group A of compounds of formula V and/or optionally present in R of compounds of formula VI can be protected, for example, with amino protecting groups which are cleavable with acid (e.g. the t-butoxycarbonyl or triphenylmethyl groups), by basic hydrolysis (e.g. the trifluoroacetyl group), by hydrazinolysis (e.g. the phthalimido group) or by catalytic cleavage in the presence of Pd (the allyloxycarbonyl group). Preferred protecting groups are the t-butyloxycarbonyl or the allyloxy-carbonyl group. Another preferred protecting group is phenylacetyl which can be cleaved off by treatment with phosphorus pentachloride or enzymatically.

Furthermore, the hydroxy groups optionally present in the group A of compounds of formula V and/or optionally present in R of compounds of formula VI can be protected, for example, with hydroxy protecting groups commonly known in the art, such as trimethylsilanyl, t-butyl-dimethylsilanyl, dimethylphenylsilanyl, triphenylmethyl, lower alkanoyl, acetyl, trifluoro-acetyl, tetrahydropyranyl, benzyl, p-nitrobenzyl or t-butoxycarbonyl.

The 7-amino group in compounds V can be protected in situ by a silanyl protecting group such as the trimethylsilanyl group.

In reacting an inner salt (i.e. salt where a carboxylate ion $COO^-$ is neutralized by a positively charged group A) or an addition salt (i.e. salt where an acid moiety is added to the 7-amino group) of a 7-amino compound of formula V, the compound V is reacted with a reactive functional derivative of a carboxylic acid of formula VI in an inert solvent (e.g. dimethylformamide, dimethylacetamide, dimethylsulfoxide and the like). According to another embodiment, a carboxylic acid of formula VI or a reactive functional derivative thereof, can be reacted, for example, with an aforementioned ester of a compound of formula V in the presence of a carbodiimide such as N,N'-dicyclohexyl-carbodiimide in an inert solvent such as ethyl acetate, acetonitrile, dioxane, chloroform, dichloromethane, benzene, N,N'-dimethylformamide or N,N'-dimethylacetamide, and subsequently the ester group can be cleaved off.

The reaction of a 7-amino compound of formula V with the carboxylic acid of formula VI or a reactive derivative thereof can conveniently be, carried out at a temperature between about −40° C. and +60° C., e.g. at room temperature. The silanyl protecting group is split off during the reaction.

Embodiment (b) of the process of the present invention involves treating a compound of formula VII with an appropriate thiol of formula R—SH or a salt thereof in the presence of a base, for example, a trialkylamine such as trimethylamine, triethylamine, sodium bicarbonate, DBU (1,8-diazabicyclo[5,4,0]undec-7-ene) to form the corresponding thioether. Carboxy, amino or hydroxy groups, which may be present, can be intermediately protected by protecting groups as described above.

Embodiment (c) of the process of the present invention involves treating a compound of formula VIII with an appropriate nitrogen nucleophile yielding the group A, e.g. a nucleophile of formula $NR^2R^3R^4$, where $R^2$, $R^3$ and $R^4$ are as above, e.g. with pyridine, 1-methyl-pyrrolidine or 2,2-dimethylamino-acetamide, or with a nitrogen nucleophile of formula $HNR^5R^6$, wherein $R^5$ and $R^6$ are as above, e.g. with pyrrolidine, or benzimidazole, (in analogy to the procedure described in EP 0 528 343) in an inert solvent such as dichloromethane at a temperature between about −40° C. and +20° C., preferably at 0° C. The carboxy protecting group $R^e$, which is preferably a silanyl protecting group such as trimethylsilanyl, is split off in the reaction (when $R^e$ is a silanyl group) or otherwise split off subsequently, such as when p-methoxybenzyl or benzhydryl is employed.

Embodiment (d) of the process of the present invention involves reacting a Schiff base of formula IX, prepared by using generally known procedures from an amino compound $H_2NR^6$, e.g. cyclopropylamine or 2-aminopyridine, and an aldehyde ZCHO, in which Z is alkyl, aryl or heterocyclyl, e.g. benzaldehyde, with a compound of formula VIII in an inert solvent such as dichloromethane or toluene. The aldehyde component liberated upon hydrolysis of the reaction mixture is separated by generally known procedures, e.g. by chromatographic methods.

Subsequently to the reactions carried out in accordance with the embodiments (a)–(d), deprotection (removal) of protected amino, hydroxy or carboxylic groups present in compounds of formula X can be achieved according to embodiment (e) of the process of the present invention as follows:

Removal of Amino Protecting Groups

Possible amino-protecting groups are those employed in peptide chemistry. Examples thereof are mentioned above.

Preferred amino protecting groups are t-butoxycarbonyl (t-BOC), trityl, allyloxycarbonyl and trimethylsilanyl.

The amino protecting groups may be cleaved off by acid hydrolysis (e.g. the t-butoxycarbonyl or trityl group), e.g. aqueous formic acid, or by basic hydrolysis (e.g. the trifluoroacetyl group). The chloroacetyl group is cleaved off by treatment with thiourea.

The allyloxycarbonyl group is cleaved in a palladium(O) catalyzed transallylation in the presence of an allyl group scavenger such as, e.g. trimethylsilanyldimethylamine, as described in Tetrahedron Letters 33, 477–480 (1992). The trimethylsilanyl group is cleaved off by hydrolysis or alcoholysis, e.g. by treatment with isopropanol.

Amino-protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about −30° C. to +40° C.). Protecting groups which are cleavable under basic conditions are generally hydrolyzed with dilute aqueous caustic alkali at 0° C. to 30° C. The chloroacetyl protecting group can be cleaved off using thiourea in acidic, neutral or alkaline medium at about 0° C.–30° C.

Removal of Hydroxy Protecting Groups

Possible hydroxy protecting groups are such as are commonly known in the art, e.g.

for protection of hydroxy groups present in R and/or in A usually trityl, lower alkanoyl, preferably acetyl, tetrahydropyranyl, p-nitrobenzyl or trialkylsilanyl, preferably trimethylsilanyl or t-butyl-dimethyl-silanyl, protecting groups are employed.

These protecting groups are e.g. removed as follows:

trityl in acidic solvents like 90% formic acid at about 0 to 50° C. or triethylsilane in trifluoroacetic acid at about −20 to 25° C.; in organic solutions of hydrochloric acid at about −50 to 25° C.;

acetyl with weak inorganic bases like sodium bicarbonate in ethanol/water at about 0 to 50° C.;

tetrahydropyranyl with weak organic acids like p-toluenesulfonic acid in an alcohol, e.g. ethanol, at about 0° C. to the boiling point of the mixture;

p-nitrobenzyl with hydrogen or a hydrogen donor like cyclohexene or cyclohexadiene and a catalyst like Pd/C in solvents like alcohols, ethyl acetate, acetic acid, DMF etc., or mixtures of these at about 0 to 50° C.

trimethylsilanyl, t-butyl-dimethyl-silanyl with e.g. $NH_4F$ in methanol or ethanol or with $NBu_4F$ in tetrahydrofuran at 0 to 20° C.

Removal of Protecting Groups at the Carboxy Function

Carboxylic acid protecting groups are such as mentioned above and preferably include ester forms which can be easily converted into a free carboxyl group under mild conditions, the ester form being exemplified by, for example, t-butyl, p-nitrobenzyl, p-methoxybenzyl, benzhydryl, allyl or trimethylsilanyl, etc.

These protecting groups may be removed as follows:

benzhydryl trifluoroacetic acid with anisol, phenol, cresol or triethylsilane at about −40° C. to room temperature; hydrogen with Pd/C in an alcohol such as ethanol or in tetrahydrofuran; $BF_3$-etherate in acetic acid at about 0 to 50° C.;

t-butyl formic acid or trifluoroacetic acid with or without anisol, phenol, cresol or triethylsilane and a solvent such as dichloromethane at about −10° C. to room temperature;

p-nitrobenzyl sodium sulfide in acetone/water at about 0 to room temperature; or hydrogen with Pd/C in an alcohol such as ethanol or in tetrahydrofuran;

p-methoxybenzyl formic acid at about 0 to 50° C.; or trifluoroacetic acid and anisol, phenol or triethylsilane at about 40° C. to room temperature; allyl palladium(O) catalyzed transallylation reaction in the presence of sodium or potassium salt of 2-ethyl hexanoic acid, see for example J. Org. Chem. 1982, 47, 587.

trimethylsilanyl with water or an alcohol such as methanol or ethanol, or a mixture of them optionally in the presence of an acid or base such as hydrochloric acid or sodium bicarbonate at 0–20° C.

In order to manufacture a readily hydrolyzable ester of the carboxylic acids of formula I in accordance with embodiment (f) of the process provided by the present invention, a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. The esterification is preferably carried out in an inert organic solvent such as dimethylacetamide, hexamethylphosphoric acid triamide, dimethyl sulfoxide or, especially, dimethylformamide. The reaction is preferably carried out at a temperature in the range of about 0–40° C.

The manufacture of the salts and hydrates of the compounds of formula I or the hydrates of said salts in accordance with embodiment (g) of the process provided by the present invention can be carried out in a manner known per se; for example, by reacting a carboxylic acid of formula I or a salt thereof with an equivalent amount of the desired base, conveniently in a solvent such as water or an organic solvent (e.g. ethanol, methanol, acetone and the like). Correspondingly, salt formation is brought about by the addition of an organic or inorganic acid. The temperature at which the salt formation is carried out is not critical. The salt formation is generally carried out at room temperature, but it can be carried out at a temperature slightly above or below room temperature, for example in the range of 0° C. to +50° C.

The manufacture of the hydrates usually is taken place automatically in the course of the manufacturing process or as a result of the hygroscopic properties of an initially anhydrous product. For the controlled manufacture of a hydrate, a completely or partially anhydrous carboxylic acid of formula I or salt thereof can be exposed to a moist atmosphere (e.g. at about +10° C. to +40° C.).

Exemplary of the process for obtaining products in accordance with the invention is the following reaction scheme (Scheme 1) below.

The preparation of starting materials V, VII and VIII and their conversion to the compounds of formula I in accordance with the present invention is given in Scheme 1.

A compound V can be prepared according to EP 0333154 by converting an acetoxy compound XI (EP 0503453) to the iodide XII which is subsequently treated in analogous manner as described above for embodiment (c) with a nitrogen nucleophile $NR^2R^3R^4$ or $HNR^5R^6$ wherein $R^2$, $R^3$, $R^4$, $R^5$ and $R^6$ taken together with the nitrogen atom have the significance given above, and $R^5$ preferably is different from hydrogen; or when A represents a group $NH-R^6(R^5=H)$, in analogous manner as described above for embodiment (d) with a corresponding Schiff base. Protecting groups can be cleaved off as described above, and the resulting product can be isolated in form of a neutral inner salt, or an addition salt with an inorganic or organic acid such as hydrogen chloride or trifluoroacetic acid.

An acetoxy compound XI may be prepared in known manner. For example it may be prepared from a 7-silanylated-3-iodomethyl-3-cephem4-carboxylic acid silanyl ester (obtainable from e.g. 7-ACA) by the method described in EP 0503453.

A compound VII can be prepared by treating a compound V or a salt or ester (preferably a trimethylsilanyl ester)

thereof with a compound Hal-CHR¹—COBr(or Cl) (XII), Hal being a halogen atom, preferably chloro or bromo and $R^1$ being as defined above, for example in dichloromethane. The product VII is isolated, after cleaving off the optional ester groups, preferably as a monohydrogen bromide (or chloride) salt.

A compound VIII can be prepared by reacting a compound XI in an analogous manner as described above for the preparation of I according to embodiment (a) with a compound of formula VI, or a reactive derivative thereof, and subsequently subjecting the resulting compound XIV in an analogous manner to the procedure described above for the preparation of XII from XI. A compound VIII is preferably converted in situ to a compound I in analogous manner to the conversion of XII into V according to embodiments (c) or (d).

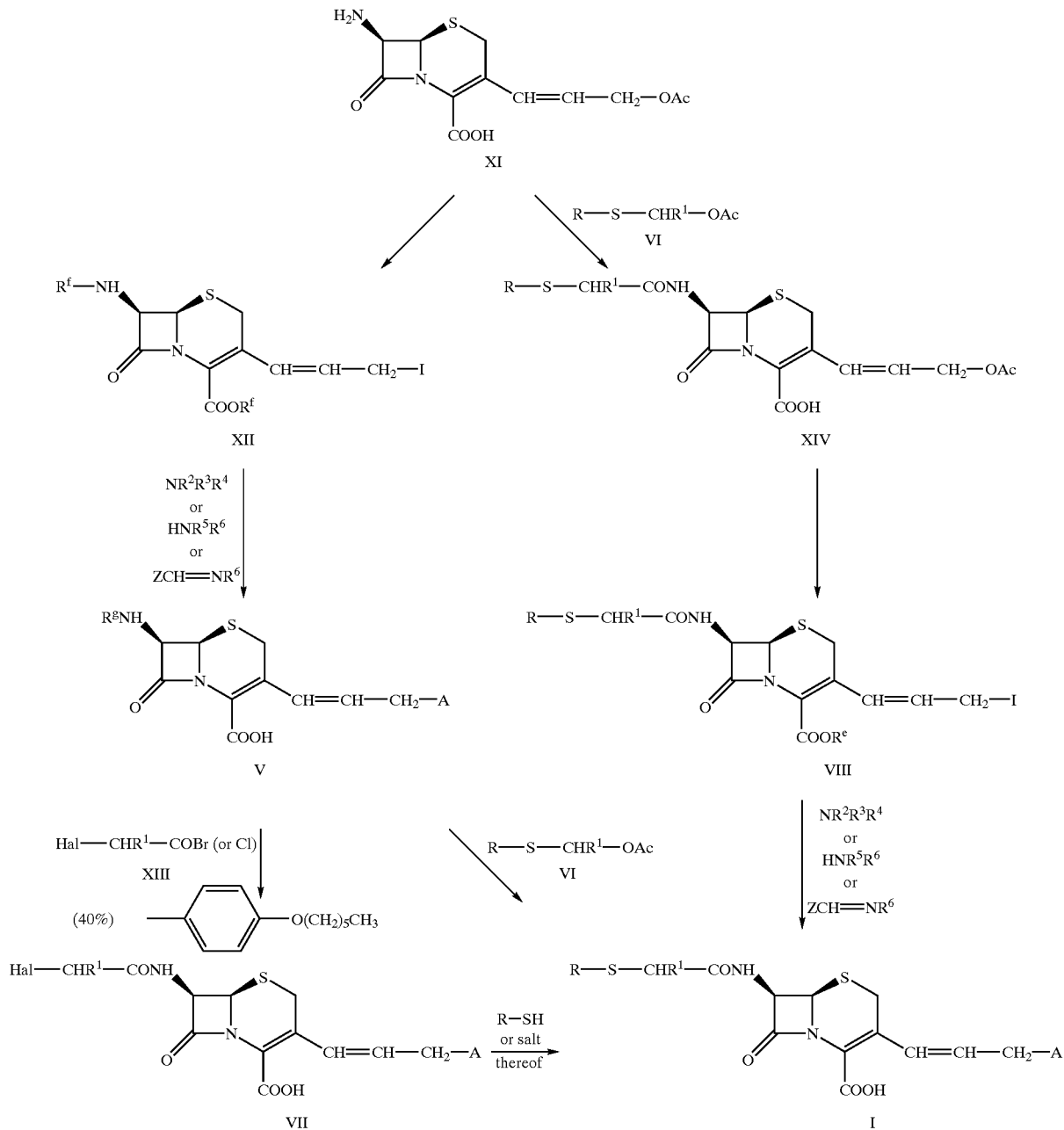

Scheme 1

Ac=acetyl;
$R^e$=carboxy protecting group, e.g. a silanyl group such as trimethylsilanyl;
$R^f$=a silanyl protecting group, e.g. trimethylsilanyl;
$R^g$=hydrogen or a silanyl protecting group, e.g. trimethylsilanyl;
Z=the residue of an aldehyde ZCHO, in which Z is alkyl, aryl or heterocyclyl; preferably phenyl;
Hal=a halogen atom, preferably chloro or bromo;
R, $R^1$, A, $R^2$, $R^3$, $R^4$, $R^5$ and $R^6$=as defined above.

The following examples illustrate the invention. All temperatures are in degrees centigrade (Celsius).

EXAMPLE 1

To a solution of 101 mg (0.6 mmol) of phenylsulfanyl-acetic acid in 1 ml of N,N-dimethylacetamide were added 97 mg (0.6 mmol) of 1,1'-carbonyldiimidazole and the reaction mixture was stirred for 0.5 h at 20° under an atmosphere of argon. To the yellow solution were added 195 mg (0.5 mmol) of (E)-(6R,7R)-7-amino-8-oxo-3-(3-pyridin-1-ium-1-yl-propenyl)-5-thia-1-aza-bicyclo[4.2.0]oct-2-ene-2-carboxylic acid chloride monohydro-chloride and stirring was continued for 2 h at 20°. The brown reaction mixture was added to 25 ml of vigorously stirred diethyl ether causing a brown precipitate to form. The solvent was decanted and the insoluble residue was stirred once more with 25 ml of diethyl ether and then isolated by filtration. The brown solid was taken up in ca. 10 ml of 20% aqueous acetonitrile and this solution was subjected to chromatographic purification on MCI gel CHP20P (Mitsubishi Chemical Corporation) using a gradient of 0–30% aqueous acetonitrile for elution. The product-containing fractions were concentrated in vacuo and freeze-dried to give 135 mg (58%) of (E)-(6R,7R)-8-oxo-7-(2-phenylsulfanyl-acetylamino)-3-(3-pyridin-1-ium-1-yl-propenyl)-5-thia-1-aza-bicyclo[4.2.0]oct-2-ene-2-carboxylate as light-yellow solid.

IR (KBr): 1766, 1670, 1650, 1604 cm$^{-1}$; MS (ISP): 468.1 (M+H$^+$).

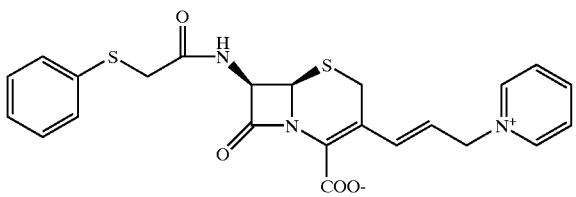

The starting material used above was prepared in the following way:

(a) To a solution of 20.0 g of (E)-(6R,7R)-3-(3-iodo-propenyl)-8-oxo-7-trimethyl-silanylamino-5-thia-1-aza-bicyclo[4.2.0]oct-2-ene-4-carboxylic acid trimethylsilanyl ester in 120 ml of dichloromethane were added at 0° over 5 min 11.3 ml (0.14 mol) of pyridine, and the reaction mixture was stirred at 0° for 22 h. Then, 160 ml of isopropanol were added and stirring was continued for 1h. The heterogeneous mixture was evaporated in vacuo and the dark-brown residue was suspended in ca. 100 ml of water and purified by chromatography on MCI gel using a gradient of 0–20% aqueous acetonitrile as eluent. The product-containing fractions were concentrated in vacuo, the remaining material was stirred with 300 ml of acetone and the insoluble material was isolated by filtration to give 5.92 g (47%) of (E)-(6R,7R)-7-amino-8-oxo-3-(3-pyridin-1-ium-1-yl-propenyl)-5-thia-1-aza-bicyclo[4.2.0]oct-2-ene-2-carboxylate as a beige solid.

NMR (D$_2$O): 3.71 (AB-system, J=15 Hz, 2H); 5.07 (d, J=5 Hz, 1H); 5.16 (m, 2H+1H); 6.08 (m, 1H); 7.04 (d, J=16 Hz, 1H); 8.03 (t, (2H); 8.57 (t, 1H); 8.84 (t, 2H) ppm. MS (ISP): 318.2 (M+H$^+$).

(b) A suspension of 1.59 g (10 mmol) of this material in 10 ml of methanol was stirred for 10 min at 200. The mixture was cooled to 0°, and upon addition of 3 ml of a 4 N solution of hydrochloric acid in diethyl ether, stirring was continued for 1 h at 0°. The insoluble material was isolated by filtration to give 1.50 g (77%) of (E)-(6R,7R)-7-amino-8-oxo-3-(3-pyridin-1-ium-1-yl-propenyl)-5-thia-1-aza-bicyclo[4.2.0]oct-2-ene-2-carboxylic acid chloride monohydrochloride as a beige solid.

IR (KBr): 1782, 1710, 1632, 1581 cm$^{-1}$; MS (ISP): 318.2 (M–2HCl+H$^+$).

EXAMPLE 2

To a solution of 88 mg (0.2 mmol) of (E)-(6R,7R)-7-(2-bromo-acetylamino)-8-oxo-3-(3-pyridin-1-ium-1-yl-propenyl)-5-thia-1-aza-bicyclo[4.2.0]oct-2-ene-2-carboxylic acid bromide in 0.4 ml of N,N-dimethylformamide were added 37 mg (0.22 mmol) of 2-mercapto-benzothiazole and 22 mg (0.22 mmol) of triethylamine. The brown solution was stirred at 20° for 1 h, then added drop-wise with stirring to 20 ml of diethyl ether and stirring was continued for one hour. The solid material was collected by filtration and purified by MCI gel chromatography in analogous manner as described in Example 1 to give 38 mg of (E)-(6R,7R)-7-[2-(benzothiazol-2-ylsulfanyl)-acetylamino]-8-oxo-3-(3-pyridin-1-ium-1-yl-propenyl)-5-thia-1-aza-bicyclo[4.2.0]oct-2-ene-2-carboxylate as a pale-yellow solid.

IR (KBr): 1774, 1646, 1602, 1546 cm$^{-1}$; MS (ISP): 525.0 (M+H$^+$).

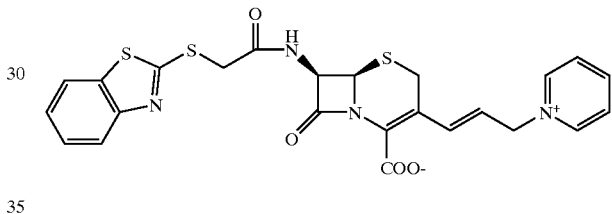

The starting material used above was prepared in the following way:

(a) To a suspension of 317 mg (1.0 mmol) of (E)-(6R,7R)-7-amino-8-oxo-3-(3-pyridin-1-ium-1-yl-propenyl)-5-thia-1-aza-bicyclo[4.2.0]oct-2-ene-2-carboxylate in 10 ml of dichloromethane was added 0.8 ml (3.0 mmol) of N,O-bis-trimethylsilanyl-trifluoroacetamide and the mixture was stirred at 20° for 15 min. After the addition of 202 mg (1.0 mmol) of bromoacetyl bromide, stirring was continued at 20° for 1 h. The heterogeneous mixture was added with stirring to 200 ml of diethyl ether containing 0.1 ml of water. After stirring for 1 h at 20°, the fine solid was isolated by filtration to give 420 mg (81%) of (E)-(6R,7R)-7-(2-bromo-acetylamino)-8-oxo-3-(3-pyridin-1-ium-1-yl-propenyl)-5-thia-1-aza-bicyclo[4.2.0]oct-2-ene-2-carboxylic acid bromide as light-brown crystals.

IR(KBr): 1749, 1663, 1646, 1586 cm$^{-1}$; MS (ISP): 438.1/440.1 (M–HBr+H$^+$).

EXAMPLES 3–6

By subjecting (E)-(6R,7R)-7-(2-bromo-acetylamino)-8-oxo-3-(3-pyridin-1-ium-1-yl-propenyl)-5-thia-1-aza-bicyclo[4.2.0]oct-2-ene-2-carboxylic acid bromide in an analogous manner to the procedure described in Example 2, but replacing 2-mercapto-benzothiazole by 5-ethoxycarbonyl-2-mercapto-4-methyl-thiazole, 2-mercapto-pyridine, 2-mercapto-pyrimidine or 2,4,5-trichloro-thiophenol, respectively, the following compounds were obtained as pale-yellow solids:

EXAMPLES 7–21

By operating in an analogous manner to the procedure described in Example 1, (E)-(6R,7R)-7-amino-3-[3-(2-methyl-pyridin-1-ium-1-yl)-propenyl]-8-oxo-5-thia-1-aza-bicyclo[4.2.0]oct-2-ene-2-carboxylic acid chloride monohydrochloride, (E)-(6R,7R)-7-amino-3-[3-(3-hydroxy-pyridin-1-ium-1-yl)-propenyl]-8-oxo-5-thia-1-aza-bicyclo[4.2.0]oct-2-ene-2-carboxylic acid chloride monohydrochloride, (E)-(6R,7R)-7-amino-8-oxo-3-[3-[4-(3-hydroxy-propyl)-pyridin-1-ium-1-yl]-propenyl]-5-thia-1-aza-bicyclo[4.2.0]oct-2-ene-2-carboxylic acid chloride monohydrochloride, (E)-(6R,7R)-7-amino-8-oxo-3-(3-quinolin-1-ium-1-yl-propenyl)-5-thia-1-aza-bicyclo[4.2.0]oct-2-ene-2-carboxylic acid chloride monohydrochloride and (E)-(6R,7R)-7-amino-3-[3-(1-methyl-pyrrolidin-1-ium-1-yl)-propenyl]-8-oxo-5-thia-1-aza-bicyclo[4.2.0]oct-2-ene-2-carboxylic acid chloride monohydrochloride were acylated with naphthalen-2-ylsulfanyl-acetic acid and with phenylsulfanyl-acetic acid, respectively, and (E)-(6R,7R)-7-amino-3-[3-(4-methyl-morpholin-4-ium-4-yl)-propenyl]-8-oxo-5-thia-1-aza-bicyclo[4.2.0]oct-2-ene-2-carboxylic acid chloride monohydrochloride, (E)-(6R,7R)-7-amino-8-oxo-3-(3-trimethylammonio-propenyl)-5-thia-1-aza-bicyclo[4.2.0]oct-2-ene-2-carboxylic acid chloride monohydrochloride, (E)-(6R,7R)-7-amino-3-[3-(carbamoylmethyl-dimethyl-ammonio)-propenyl]-8-oxo-5-thia-1-aza-bicyclo[4.2.0]oct-2-ene-2-carboxylic acid chloride monohydrochloride, (E)-(6R,7R)-7-amino-3-[3-(benzimidazol-1-ylamino)-propenyl]-8-oxo-5-thia-1-aza-bicyclo[4.2.0]oct-2-ene-2-carboxylic acid dihydrochloride and (E)-(6R,7R)-7-amino-8-oxo-3-(3-pyrrolidin-1-yl-propenyl)-5-thia-1-aza-bicyclo[4.2.0]oct-2-ene-2-carboxylic acid dihydrochloride were acylated with naphthalen-2-ylsulfanyl-acetic acid, respectively, to give the following compounds as pale-yellow solids:

| Example No | R | MS (ISP) (M + H⁺) | IR (KBr) (cm⁻¹) |
|---|---|---|---|
| 3 | ethyl 2-(methylthiazol-...)carboxylate group | 561.2 | 1774, 1711, 1692, 1665, 1632, 1550 |
| 4 | pyridin-2-yl-methyl | 469.1 | 1765, 1662, 1632, 1601, 1578, 1559 |
| 5 | pyrimidin-2-yl-methyl | 470.1 | 1768, 1663, 163, 1601, 1562, 1553 |
| 6 | 2,4,5-trichlorophenyl-methyl | 486.3 | 1771, 1666, 1625, 1599, 1528 |

| Example No | R | A | MS (ISP) (M + H⁺) | IR (KBr) (cm⁻¹) |
|---|---|---|---|---|
| 7 | naphthalen-2-yl | 2-methyl-pyridin-1-ium-1-yl | 532.2 | 1762, 1654, 1603, 1544 |

-continued
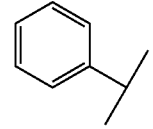
| Example No | R | A | MS (ISP) (M + H⁺) | IR (KBr) (cm⁻¹) |
|---|---|---|---|---|
| 8 | 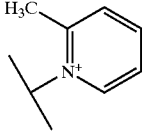 | 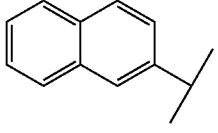 | 482.3 | 1769, 1672, 1630, 1605, 1581, |
| 8 | 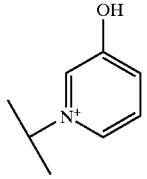 | 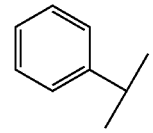 | 534.2 | 1753, 1658, 1590, 1537, 1501 |
| 10 | 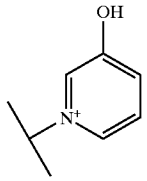 | 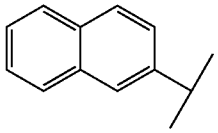 | 484.2 | 1782, 1712, 1638, 1592, 1573 |
| 11 | 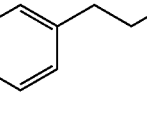 | 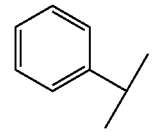 | 576.0 | 1779, 1654, 1641, 1601, 1570, 1543 |
| 12 | 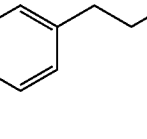 | 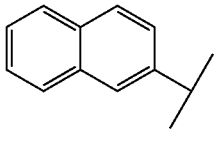 | 526.0 | 1764, 1653, 1633, 1607, 1541 |
| 13 | 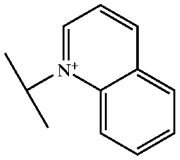 | 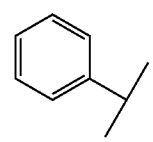 | 568.1 | 1768, 1658, 1594, 1545, 1530 |
| 14 | 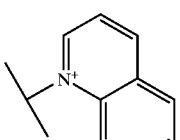 | 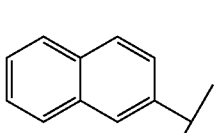 | 518.1 | 1765, 1666, 1606, 1547, 1528 |
| 15 | 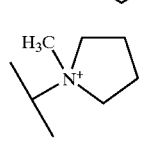 | | 524.2 | 1762, 1657, 1604 1537 |

-continued

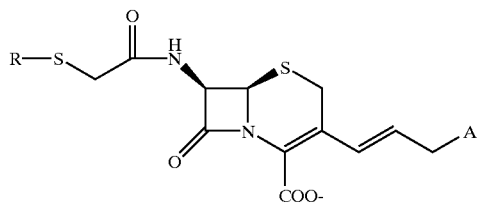

| Example No | R | A | MS (ISP) (M + H⁺) | IR (KBr) (cm⁻¹) |
|---|---|---|---|---|
| 16 | phenyl-CH< | H₃C-N⁺(pyrrolidine)-CH< | 474.3 | 1769, 1672, 1609, |
| 17 | 2-naphthyl-CH< | H₃C-N⁺(morpholine)-CH< | 540.2 | 1766, 1658, 1604 1543 |
| 18 | 2-naphthyl-CH< | (CH₃)₃N⁺-CH< | 498.2 | 1763, 1658, 1608, 1542 |
| 19 | 2-naphthyl-CH< | (CH₃)₂N⁺(CH₂CONH₂)-CH< | 541.1 | 1762, 1693, 1656, 1626, 1593, 1537 |
| 20 | 2-naphthyl-CH< | benzimidazolium-CH< | 557.1 | 1761, 1657, 1591, 1543 |
| 21 | 2-naphthyl-CH< | H-N⁺(pyrrolidine)-CH< | 510.4 | |

The starting material used above was prepared in the following way:

(a) By subjecting (E)-(6R,7R)-3-(3-iodo-propenyl)-8-oxo-7-trimethylsilanylamino-5-thia-1-aza-bicyclo[4.2.0]oct-2-ene-4-carboxylic acid trimethylsilanyl ester in an analogous manner to the procedure described in Example 1(a,b), but replacing pyridine by 2-methyl-pyridine, 3-hydroxy-pyridine, 4-(3-hydroxy-propyl)-pyridine, quinoline, 1-methyl-pyrrolidine, 4-methyl-morpholine, trimethylamine, 2-dimethylamino-acetamide, benzoimidazole or pyrrolidine, the following compounds were obtained as beige crystalline solids:

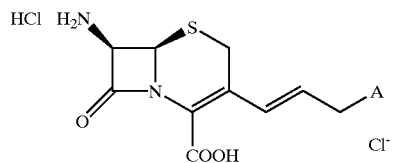

| Compound | A | MS (ISP) (M − 2HCl + H⁺) | IR (KBr) (cm⁻¹) |
|---|---|---|---|
| (E)-(6R,7R)-7-Amino-3-[3-2-methyl-pyridin-1-ium-1-yl)-propenyl]-8-oxo-5-thia-1-aza-bicyclo[4.2.0]oct-2-ene-2-carboxylic acid chloride monohydrochloride | 2-methylpyridinium | 332.2 | 1781, 1709 1631, 1579 |
| (E)-(6R,7R)-7-Amino-3-[3-(3-hydroxy-pyridin-1-ium-1-yl)-propenyl]-8-oxo-5-thia-1-aza-bicyclo[4.2.0]oct-2-ene-2-carboxylic acid chloride monohydrochloride | 3-hydroxypyridinium | 334.2 | 1782, 1709, 1632, 1602, 1585, 1510 |
| (E)-(6R,7R)-7-Amino-3-[3-[4-(3-hydroxy-propyl)-pyridin-1-ium-1-yl]-propenyl]-8-oxo-5-thia-1-aza-bicyclo[4.2.0]oct-2-ene-2-carboxylic acid chloride monohydrochloride | 4-(3-hydroxypropyl)pyridinium | 376.3 | 1780, 1708, 1639 |
| (E)-(6R,7R)-7-Amino-8-oxo-3-(3-quinolin-1-ium-1-yl-propenyl)-5-thia-1-aza-bicyclo[4.2.0]oct-2-ene-2-carboxylic acid chloride monohydrochloride | quinolinium | 368.1 | 1783, 1710, 1625, 1591, 1527, |
| (E)-(6R,7R)-7-Amino-3-[3-(1-methyl-pyrrolidin-1-ium-1-yl)-propenyl]-8-oxo-5-thia-1-aza-bicyclo[4.2.0]oct-2-ene-2-carboxylic acid chloride monohydrochloride | 1-methylpyrrolidinium | 324.3 | 1781, 1708, 1638, 1589, |
| (E)-(6R,7R)-7-Amino-3-[3-(4-methyl-morpholin-4-ium-4-yl)-propenyl]-8-oxo-5-thia-1-aza-bicyclo[4.2.0]oct-2-ene-2-carboxylic acid chloride monohydrochloride | 4-methylmorpholinium | 340.3 | 1782, 1711, |
| (E)-(6R,7R)-7-Amino-8-oxo-3-(3-trimethylammonio-propenyl)-5-thia-1-aza-bicyclo[4.2.0]oct-2-ene-2-carboxylic acid chloride monohydrochloride | trimethylammonio | 298.3 | 1774, 1719, 1681, 1632, 1582, 1536 |
| (E)-(6R,7R)-7-Amino-3-[3-(carba-moylmethyl-dimethyl-ammonio)-propenyl]-8-oxo-5-thia-1-aza-bicyclo[4.2.0]oct-2-ene-2-carboxylic acid chloride monohydrochloride | carbamoylmethyl-dimethylammonio | 341.2 | 1781, 1691, 1629, 1593 |

-continued

| Compound | A | MS (ISP) (M − 2HCl + H+) | IR (KBr) (cm⁻¹) |
|---|---|---|---|
| (E)-(6R,7R)-7-Amino-3-[3-(benzimidazol-1-ylamino)-propenyl]-8-oxo-5-thia-1-aza-bicyclo[4.2.0]oct-2-ene-2-carboxylic acid dihydrochloride | | 357.3 | 1779, 1706, |
| (E)-(6R,7R)-7-Amino-8-oxo-3-(3-pyrrolidin-1-yl-propenyl)-5-thia-1-aza-bicyclo[4.2.0]oct-2-ene-2-carboxylic acid dihydrochloride | | 310.3 | |

EXAMPLE 22

A mixture of 2.49 g of (Z)-(6R,7R)-3-(3-acetoxy-propenyl)-7-[2-(naphthalen-2-ylsulfanyl)-acetylamino]-8-oxo-5-thia-1-aza-bicyclo[4.2.0]oct-2-ene-2-carboxylic acid, 1.62 g of hexamethyldisilazane and 0.07 g of saccharin in 15 ml of dichloromethane was heated at reflux temperature for 2 h. The clear solution formed was cooled to 0° and 2.60 g of iodotrimethylsilane were added. The mixture was stirred at 0° for 18 h. To the so formed (6R,7R)-3-(3-iodo-propenyl)-7-[2-(naphthalen-2-ylsulfanyl)-acetylamino]-8-oxo-5-thia-1-aza-bicyclo[4.2.0]oct-2-ene-2-carbocylic acid 2.0 ml of pyridine were added and stirring was continued at 0° for 8 h. The heterogeneous mixture was treated with 20 ml of 2-propanol and stirred for 1 h at 0°. After the addition of 8 ml of diethyl ether, stirring was continued for 0.5 h and the insoluble material was isolated by filtration. The yellow solid was subjected to MCI gel chromatography in analogous manner as described in Example 1, using 0–30% aqueous acetonitrile as eluent, to give after freeze-drying of the product-containing fractions 0.59 g of (E)-(6R,7R)-7-[2-(naphthalen-2-ylsulfanyl)-acetylamino]-8-oxo-3-(3-pyridin-1-ium-1-yl-propenyl)-5-thia-1-aza-bicyclo[4.2.0]oct-2-ene-2-carboxylate as a pale-yellow solid.

IR (KBr): 1778, 1654, 1602, 1521 cm⁻¹; MS (ISP): 518.1 (M+H⁺).

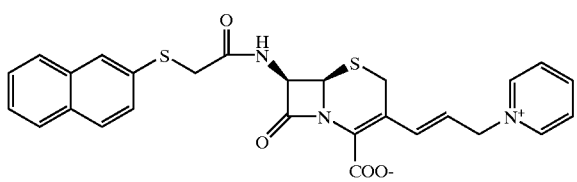

The starting material used above was prepared in the following way:

(a) To a solution of 10.5 g (48 mmol) of naphthalen-2-ylsulfanyl-acetic acid in 80 ml of N,N-dimethylacetamide were added 7.8 g (48 mmol) of 1,1'-carbonyldiimidazole and the reaction mixture was stirred for 0.5 h at 20° under an atmosphere of argon. To the yellow solution were added 11.93 g (0.5 mmol) of (Z and E)-(6R,7R)-3-(3-acetoxy-propenyl)-7-amino-8-oxo-5-thia-1-aza-bicyclo [4.2.0]oct-2-ene-2-carboxylic acid and stirring was continued for 3 h at 20°. The brown solution was diluted with ethyl acetate (0.5 1), washed with 1 N hydrochloric acid (0.2 1) and with water (5×0.1 1), dried over sodium sulfate and evaporated in vacuo. The remaining material was crystallized from ethyl acetate to give 11.7 g (58%) of (Z)-(6R,7R)-3-(3-acetoxy-propenyl)-7-[2-(naphthalen-2-ylsulfanyl)-acetylamino]-8-oxo-5-thia-1-aza-bicyclo [4.2.0]oct-2-ene-2-carboxylic acid as a light brown solid.

IR (KBr): 1771, 1731, 1701, 1643, 1623, 1588, 1535 cm⁻¹; MS (ISP): 499.1 (M+H⁺).

EXAMPLE 23–25

By operating in an analogous manner to the procedure described in Example 1, (E)-(6R,7R)-7-amino-3-[3-(4-hydroxy-piperidin-1-yl)-propenyl]-8-oxo-5-thia-1-aza-bicyclo[4.2.0]oct-2-ene-2-carboxylic acid monohydroiodide was acylated with naphthalen-2-ylsulfanyl-acetic acid, with benzothiazol-2-ylsulfanyl-acetic acid, and with (3,5-dimethyl-phenylsulfanyl)-acetic acid, respectively, to give the following compounds as pale-yellow solids:

| Example No | R | MS (ISP) (M + H⁺) | IR (KBr) (cm⁻¹) |
|---|---|---|---|
| 23 | naphthalen-2-ylmethyl | 540.3 | 1772, 1656, 1593, 1538 |
| 24 | benzothiazol-2-ylmethyl | 547.3 | 1774, 1663, 1597, 1537 |
| 25 | 3,5-dimethylphenylmethyl | 518.4 | 1760, 1674, 1653, 1601, 1537 |

The starting materials used above were prepared in the following way:

(a) A solution of 2.0 g of 4-hydroxy-piperidine, 1.61 g of hexamethyldisilazane and 0.15 g of saccharin in 30 ml of acetonitrile was heated to 80° for 2 h, the ammonia gas formed being vented by passing nitrogen gas through the reaction apparatus. The solution was cooled to 0° and then added to an ice-cold solution of 5.2 g of (E)-(6R,7R)-3-(3-iodo-propenyl)-8-oxo-7-trimethysilanylamino-5-thia-1-aza-bicyclo[4.2.0]oct-2-ene-4-carboxylic acid trimethylsilanyl ester in 30 ml of dichloromethane, and the dark reaction mixture was stirred at 0° for 4 h. Then, 30 ml of isopropanol was added and stirring was continued for 1 h at 20°. The heterogeneous mixture was kept at 0° for 15 h and the precipitate formed was isolated by filtration. The dark-brown solid was dissolved in 50 ml of water, and the pH of the solution was adjusted to 2.5 by the addition of 47% aqueous hydroiodic acid. The precipitate formed was isolated by filtration, washed with 30 ml of water and dried to give 0.4 g of (E)-(6R,7R)-7-amino-3-[3-(4-hydroxy-piperidin-1-yl)-propenyl]-8-oxo-5-thia-1-aza-bicyclo[4.2.0]oct-2-ene-2-carboxylic acid iodide monohydroiodide, as a light-brown solid.

MS (ISP): 340.4 (M−2HI+H⁺); IR (Nujol): 1780, 1690, 1614 cm⁻¹.

EXAMPLES 26–32

By operating in an analogous manner to the procedure described in Example 1, (E)-(6R,7R)-7-amino-8-oxo-3-(3-pyridin-1-ium-1-yl-propenyl)-5-thia-1-azabicyclo[4.2.0]oct-2-ene-2-carboxylic acid chloride monohydrochloride, and (E)-(6R,7R)-7-amino-3-[3-(2-methyl-pyridin-1-ium-1-yl)-propenyl]-8-oxo-5-thia-1-aza-bicyclo[4.2.0]oct-2-ene-2-carboxylic acid chloride monohydrochloride, and (E)-(6R,7R)-7-amino-3-[3-(1-methyl-pyrrolidin-1-ium-1-yl)-propenyl]-8-oxo-5-thia-1-aza-bicyclo[4.2.0]oct-2-ene-2-carboxylic acid chloride monohydrochloride were acylated with (3,5-dimethyl-phenylsulfanyl) acetic acid, and (E)-(6R,7R)-7-amino-3-[3-(carbamoylmethyl-dimethyl-ammonio)-propenyl]-8-oxo-5-thia-1-aza-bicyclo[4.2.0]oct-2-ene-2-carboxylic acid chloride monohydrochloride was acylated with (3,5-dimethyl-phenylsulfanyl)acetic acid, with pyridin-4-ylsulfanyl-acetic acid, with 2-(biphenyl-4-ylsulfanyl)-acetic acid, and with 2-(4'-methoxy-biphenyl-4-ylsulfanyl)-acetic acid, respectively, to give the following compounds as pale-yellow solids:

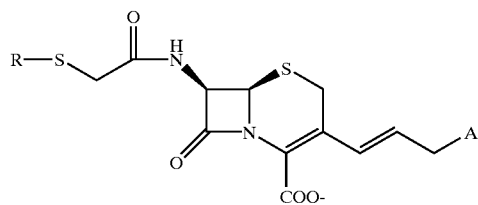

| Example No | R | A | MS (ISP) (M + H⁺) | IR (KBr) (cm⁻¹) |
|---|---|---|---|---|
| 26 | 3,5-dimethylphenyl-CH₂ | pyridinium-CH₂ | 496.1 | 1764, 1656, 1630, 1601 |
| 27 | 3,5-dimethylphenyl-CH₂ | 2-methylpyridinium-CH₂ | 510.3 | 1763, 1659, 1633, 1602, 1546 |
| 28 | 3,5-dimethylphenyl-CH₂ | 1-methylpyrrolidinium-CH₂ | 502.2 | 1769, 1667, 1633, 1602, 1550 |
| 29 | 3,5-dimethylphenyl-CH₂ | (CH₃)₂N⁺-CH₂C(O)NH₂ | 519.2 | 1768, 1690, 1631, 1600, 1548 |
| 30 | 4-pyridyl-CH₂ | (CH₃)₂N⁺-CH₂C(O)NH₂ | 492.2 | 1767, 1691, 1631, 1601, 1582 |
| 31 | biphenyl-4-yl-CH₂ | (CH₃)₂N⁺-CH₂C(O)NH₂ | 567.3 | 1758, 1693, 1653, 1597, 1529 |
| 32 | 4'-methoxybiphenyl-4-yl-CH₂ | (CH₃)₂N⁺-CH₂C(O)NH₂ | 597.3 | 1766, 1691, 1660, 1603, 1517 |

The starting material used above was prepared in the following way:

(a) To a solution of 4.30 g of 4'-methoxy-biphenyl-4-thiol and 3.34 g of ethyl 2-bromo-acetate in 10 ml of ethanol was added over 5 min a solution of 1.12 g of potassium hydroxide in 20 ml of ethanol. The reaction mixture was stirred at 20° for 4 h and then, 1.68 g of potassium hydroxide and 3 ml of water were added and stirring was continued for 15 h at 20°. The mixture was poured onto 150 ml of ice/water and the pH of the mixture set to 2 by the addition of 3N hydrochloric acid. The precipitate was collected by filtration, washed with water and dried to give 4.21 g of 2-(4'-methoxy-biphenyl-4-ylsulfanyl)-acetic acid as white crystals.

NMR (DMSO-$d_6$): 3.79 (s, 3H); 3.81 (s, 2H); 7.01 (d, 2H); 7.39 (d, 2H); 7.56 (d, 2H); 7.60 (d, 2H) ppm.

EXAMPLES 33–43

By operating in an analogous manner to the procedure described in Example 1, (E)-(6R,7R)-7-amino-3-[3-[(3-hydroxy-2,2-dimethyl-propyl)-dimethyl-ammonio]-propenyl]-8-oxo-5-thia-1-aza-bicyclo[4.2.0]oct-2-ene-2-carboxylic acid chloride monohydrochloride and (E)-(6R,7R)-7-amino-3-[-3-(1-azonia-bicyclo[2.2.2]oct-1-yl)-propenyl]-8-oxo-5-thia-1-aza-bicyclo[4.2.0]oct-2-ene-2-carboxylic acid chloride monohydrochloride were acylated with naphthalen-2-ylsulfanyl-acetic acid, (E)-(6R,7R)-7-amino-3-[3-(4-carbamoyl-pyridin-1-ium-1-yl)-propenyl]-8-oxo-5-thia-1-aza-bicyclo[4.2.0]oct-2-ene-2-carboxylic acid chloride monohydrochloride was acylated with (3,5- and with (3,4-dimethylphenylsulfanyl)-acetic acid, (E)-(6R,7R)-7-amino-3-[3-(1,4-dimethyl-piperazin-1-ium-1-yl)-propenyl]-8-oxo-5-thia-1-aza-bicyclo[4.2.0]oct-2-ene-2-carboxylic acid chloride dihydrochloride was acylated with naphthalen-2-ylsulfanyl-acetic acid, with benzothiazol-2-ylsulfanyl-acetic acid, and with (3,4-dimethyl-phenylsulfanyl)acetic acid, and (E)-(6R,7R)-7-amino-3-[3-[(2-hydroxy-ethyl)-dimethyl-ammonio]-propenyl]-8-oxo-5-thia-1-aza-bicyclo[4.2.0]oct-2-ene-2-carboxylic acid chloride monohydrochloride was acylated with naphthalen-2-ylsulfanyl-acetic acid, with benzothiazol-2-ylsulfanyl-acetic acid, with (3,4- and with (3,5-dimethyl-phenylsulfanyl)-acetic acid, respectively, to give the following compounds as pale-yellow solids:

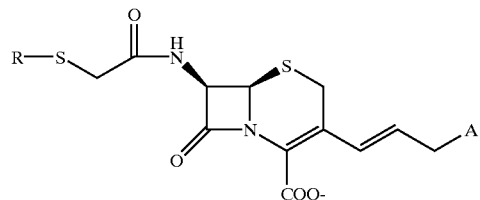

| Example No | R | A | MS (ISP) (M + H⁺) | IR (Nujol) (cm⁻¹) |
|---|---|---|---|---|
| 33 | naphthalen-2-yl | –N⁺(CH₃)₂–C(CH₃)₂–CH₂OH | 570.2 | 1769, 1667, 1606, 1556 |
| 34 | naphthalen-2-yl | 1-azonia-bicyclo[2.2.2]oct-1-yl | 550.1 | 1764, 1663, 1612, 1558, 1501 |
| 35 | 3,5-dimethylphenyl | 4-carbamoyl-pyridin-1-ium-1-yl | 539.2 | 1766, 1687, 1640, 1600 |
| 36 | 3,4-dimethylphenyl | 4-carbamoyl-pyridin-1-ium-1-yl | 539.2 | 1767, 1689, 1640, 1598 |
| 37 | naphthalen-2-yl | 1,4-dimethyl-piperazin-1-ium-1-yl | 553.1 | 1768, 1667, 1606, 1501 |

-continued

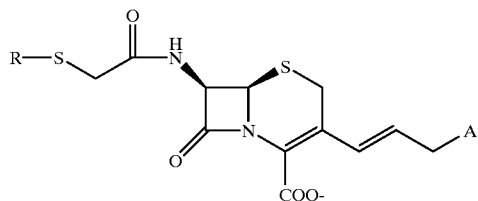

| Example No | R | A | MS (ISP) (M + H⁺) | IR (Nujol) (cm⁻¹) |
|---|---|---|---|---|
| 38 | benzothiazol-2-yl-CH₂– | 4,4-dimethyl-1-methylpiperazinium | 560.3 | 1770, 1678, 1611, 1561 |
| 39 | 3,4-dimethylphenyl-CH₂– | 4,4-dimethyl-1-methylpiperazinium | 531.2 | 1768, 1667, 1606 |
| 40 | naphthalen-2-yl-CH₂– | (2-hydroxyethyl)trimethylammonium | 528.1 | 1765, 1659, 1601 |
| 41 | benzothiazol-2-yl-CH₂– | (2-hydroxyethyl)trimethylammonium | 535.3 | 1769, 1677, 1609 |
| 42 | 3,5-dimethylphenyl-CH₂– | (2-hydroxyethyl)trimethylammonium | 506.2 | 1766, 1666, 1601 |
| 43 | 3,4-dimethylphenyl-CH₂– | (2-hydroxyethyl)trimethylammonium | 506.3 | 1769, 1666, 1606 |

The starting materials used above were prepared in the following way:

(a) By subjecting (E)-(6R,7R-3-(3-iodo-propenyl)-8-oxo-7-trimethylsilanyl amino 5-thia-1-aza-bicyclo[4.2.0]oct-2-ene-4-carboxylic acid trimethylsilanyl ester in an analogous manner to the procedure described in Example 1(a,b), but replacing pyridine by 1-aza-bicyclo[2.2.2]octane, 1,4-dimethyl-piperazine, or in an analogous manner to the procedure described in Examples 23–25(a), but replacing trimethylsilanylated 4-hydroxy-piperidine by trimethyl-silanylated 4-carbamoyl-pyridine, 2,2-dimethyl-3-dimethylamino-1-propanol or 2-dimethylamino-ethanol, respectively, the following compounds were obtained as beige crystalline solids:

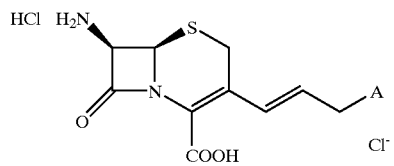

| Compound | A | MS (ISP) (M − 2HCl + H⁺) | IR (KBr) (cm⁻¹) |
|---|---|---|---|
| (E)-(6R,7R)-7-Amino-3-[1-azonia-bicyclo[2.2.2]oct-1-yl)-propenyl]-8-oxo-5-thia-1-aza-bicyclo[4.2.0]oct-2-ene-2-carboxylic acid chloride mononohydrochloride | | 350.3 | |
| (E)-(6R,7R)-7-Amino-3-[3-(1,4-dimethyl-piperazin-1-ium-1-yl)-propenyl]-8-oxo-5-thia-1-aza-bicyclo[4.2.0]oct-2-ene-2-carboxylic acid chloride dihydrochloride | | 353.3 (M − 3HCl + H⁺) (M − 3HCl + H) | 1781, 1708, 1666, 1640, 1590 |
| (E)-(6R,7R)-7-Amino-3-[3-(4-carbamoyl-pyridin-1-ium-1-yl)-propenyl]-8-oxo-5-thia-1-aza-bicyclo[4.2.0]oct-2-ene-2-carboxylic acid chloride monohydrochloride | | 361.1 | 1803, 1789, 1662, 1615 1589, 1570 |
| (E)-(6R,7R)-7-Amino-3-[3-[(3-hydroxy-2,2-dimethyl-propyl)-dimethyl-ammonio]-propenyl]-8-oxo-5-thia-1-aza-bicyclo[4.2.0]oct-2-ene-2-carboxylic acid chloride monohydrochloride | | 370.4 | 1779, 1707, 1638, 1614, 1574 |
| (E)-(6R,7R)-7-Amino-3-[3-[(2-hydroxy-ethyl)-dimethyl-ammonio]-propenyl]-8-oxo-5-thia-1-aza-bicyclo[4.2.0]oct-2-ene-2-carboxylic acid chloride monohydrochloride | | 328.2 | 1780, 1702, 1640, 1590 |

EXAMPLES 44–55

By operating in an analogous manner to the procedure described in Example 1, (E)-(6R,7R)-7-amino-3-[3-(4-methyl-morpholin-4-ium-4-yl)-propenyl]-8-oxo-5-thia-1-aza-bicyclo[4.2.0]oct-2-ene-2-carboxylic acid chloride monohydrochloride was acylated with
(3,5-dimethyl-phenylsulfanyl)-acetic acid,
benzothiazol-2-ylsulfanyl-acetic acid,
(1H-indol-4-ylsulfanyl)-acetic acid,
[4-(1,1-dimethylethyl)-phenylsulfanyl]-acetic acid,
(4-trifluoromethyl-phenylsulfanyl)-acetic acid,
(2-trifluoromethyl-phenylsulfanyl)-acetic acid,
(3,4-dimethyl-phenylsulfanyl)-acetic acid,
phenylmethylsulfanyl-acetic acid,
1,1-dimethylethylsulfanyl-acetic acid,
cyclohexylsulfanyl-acetic acid,
butylsulfanyl-acetic acid, and with
(biphenyl-4-ylsulfanyl)-acetic acid,
respectively, to give the following compounds as pale-yellow solids:

| Example No | R | MS (ISP) (M + H⁺) | IR (Nujol) (cm⁻¹) |
|---|---|---|---|
| 44 | | 518.2 | 1768, 1666, 1631, 1601 |
| 45 | | 547.1 | 1768, 1673, 1605 |

-continued

Structure (Examples 46–54): R—S—CH2—C(=O)—NH— attached to cephem core with 3-[propenyl-(N-methyl-morpholinium)] and 2-carboxylate.

| Example No | R | MS (ISP) (M + H⁺) | IR (Nujol) (cm⁻¹) |
|---|---|---|---|
| 46 | 1H-indol-4-ylmethyl | 529.2 | 1769, 1667, 1605 |
| 47 | 4-tert-butylbenzyl | 546.2 | 1768, 1667, 1605, 1543 |
| 48 | 4-(trifluoromethyl)benzyl | 558.1 | 1763, 1668, 1602 |
| 49 | 2-(trifluoromethyl)benzyl | 558.2 | 1769, 1672, 1605, 1556 |
| 50 | 3,4-dimethylbenzyl | 518.2 | 1769, 1662, 1606 |
| 51 | benzyl (phenylethyl) | 504.2 | 1768, 1667, 1606 |
| 52 | neopentyl (2,2-dimethylpropyl) | 470.2 | 1768, 1665, 1632 |
| 53 | cyclohexylmethyl | 496.1 | 1768, 1666, 1605, 1547 |
| 54 | n-pentyl | 470.2 | 1761, 1664, 1600 |
| 55 | 4-biphenylmethyl | 566.3 | 1759, 1659, 1599, 1530 |

EXAMPLES 56–81

By operating in an analogous manner to the procedure described in Example 1, (E)-(6R,7R)-7-amino-3-[3-[(1R,2S- and [(1S,2S)-2-hydroxymethyl-1-methyl-pyrrolidin-1-ium-1-yl-propenyl]-8-oxo-5-thia-1-aza-bicyclo[4.2.0]oct-2-ene-2-carboxylate monohydroiodide and (E)-(6R,7R)-7-amino-3-[3-(4-aza-1-azonia-bicyclo[2,2,2]oct-1-yl)-propenyl]-8-oxo-5-thia-1-aza-bicyclo[4.2.0]oct-2-ene-2-carboxylate dihydroiodide were acylated with naphthalen-2-ylsulfanyl-acetic acid, with benzothiazol-2-ylsulfanyl-acetic acid, and with (3,5-dimethyl-phenylsulfanyl)-acetic acid, respectively, (E)-(6R,7R)-7-amino-3-[3-[(3-hydroxy-propyl)-dimethyl-ammonio]-propenyl]-8-oxo-5-thia-1-aza-bicyclo[4.2.0]oct-2-ene-2-carboxylate monohydroiodide and (E)-(6R,7R)-7-amino-3-[3-(2,3,4,6,7,8,9,10-octahydro-pyrimido[1,2-a]azepin-1-ium-1-yl]-propenyl]-8-oxo-5-thia-1-aza-bicyclo[4.2.0]oct-2-ene-2-carboxylate monohyroiodide and (E)-(6R,7R)-7-amino-3-[3-[(2-hydroxy-1-hydroxymethyl-ethyl)-dimethyl-ammonio]-propenyl]-8-oxo-5-thia-1-aza-bicyclo[4.2.0]oct-2-ene-2-carboxylate monohydroiodide were acylated with naphthalen-2-ylsulfanyl-acetic acid and with benzothiazol-2-ylsulfanyl-acetic acid, respectively, (E)-(6R,7R)-7-amino-3-[3-[(bis-2-hydroxy-ethyl)-methyl-ammonio]-propenyl]-8-oxo-5-thia-1-aza-bicyclo[4.2.0]oct-2-ene-2-carboxylate monohydroiodide and (E)-(6R,7R)-7-amino-3-[3-(cis- and -(trans-4-hydroxy-1-methyl-piperidin-1-ium-1-yl)-propenyl]-8-oxo-5-thia-1-aza-bicyclo[4.2.0]oct-2-ene-2-carboxylate monohydroiodide and (E)-(6R,7R)-7-amino-3-[3-(4-carbamoylmethyl-pyridin-1-ium-1-yl)-propenyl]-8-oxo-5-thia-1-aza-bicyclo[4.2.0]oct-2-ene-2-carboxylate monohydroiodide were acylated with naphthalen-2-ylsulfanyl-acetic acid, and with (3,5-dimethylphenylsulfanyl)-acetic acid, respectively, (E)-(6R,7R)-7-amino-3-[3-(carboxymethyl-dimethyl-ammonio)-propenyl]-8-oxo-5-thia-1-aza-bicyclo[4.2.0]oct-2-ene-2-carboxylate monohydroiodide, and (E)-(6R,7R)-7-amino-3-[3-(4-dimethylamino-pyridin-1-ium-1-yl)-propenyl]-8-oxo-5-thia-1-aza-bicyclo[4.2.0]oct-2-ene-2-carboxylate monohydroiodide, and (E)-(6R,7R)-7-amino-3-[3-(4-carboxymethylsulfanyl-pyridin-1-ium-1-yl)-propenyl]-8-oxo-5-thia-1-aza-bicyclo[4.2.0]oct-2-ene-2-carboxylate monohydroiodide, and (E)-(6R,7R)-7-amino-3-[3-(4-methyl-pyridin-1-ium-1-yl)-propenyl]-8-oxo-5-thia-1-aza-bicyclo[4.2.0]oct-2-ene-2-carboxylate monohydroiodide, and (E)-(6R,7R)-7-amino-3-[3-[[(S)-1-carboxy-2-phenyl-ethyl]-dimethyl-ammonio]-propenyl]-8-oxo-5-thia-1-aza-bicyclo[4.2.0]oct-2-ene-2-carboxylate monohydroiodide were acylated with naphthalen-2-ylsulfanyl-acetic acid, respectively, (E)-(6R,7R)-7-amino-3-[3-[4-[N-(2-hydroxy-ethyl)-carbamoylmethyl]-pyridin-1-ium-1-yl]-propenyl]-8-oxo-5-thia-1-aza-bicyclo[4.2.0]oct-2-ene-2-carboxylate monohydroiodide was acylated with (3,5-dimethyl-phenylsulfanyl)-acetic acid, (E)-(6R,7R)-7-amino-3-[3-[4-[N-[2-(2-hydroxy-ethoxy)-ethyl]-carbamoylmethyl]-pyridin-1-ium-1-yl]-propenyl]-8-oxo-5-thia-1-aza-bicyclo[4.2.0]oct-2-ene-2-carboxylate monohydroiodide was acylated with benzothiazol-2-ylsulfanyl-acetic acid, and (E)-(6R,7R)-7-amino-3-[3-(carbamoylmethyl-dimethyl-ammonio)-propenyl]-8-oxo-5-thia-1-aza-bicyclo[4.2.0]oct-2-ene-2-carboxylate monohydroiodide was acylated with ((Z)-2-cyano-vinylsulfanyl)-acetic acid, to give the following compounds as pale-yellow solids:

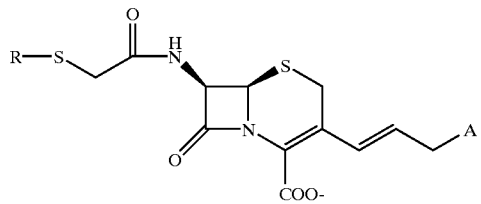

| Example No | R | A | MS (ISP) (M + H+) | IR (Nujol) (cm−1) |
|---|---|---|---|---|
| 56 | naphthalen-2-ylmethyl | 2-(hydroxymethyl)-1,1-dimethylpyrrolidinium | 554.3 | 1761, 1666, 1588, 1500 |
| 57 | benzothiazol-2-ylmethyl | 2-(hydroxymethyl)-1,1-dimethylpyrrolidinium | 561.3 | 1770, 1676, 1607 |
| 58 | 3,5-dimethylphenylmethyl | 2-(hydroxymethyl)-1,1-dimethylpyrrolidinium | 532.3 | 1765, 1668, 1600 |
| 59 | naphthalen-2-ylmethyl | 1-methyl-DABCO | 551.4 | 1758, 1660, 1614, 1590 |
| 60 | benzothiazol-2-ylmethyl | 1-methyl-DABCO | 558.4 | 1763, 1680, 1650, 1600 |

-continued
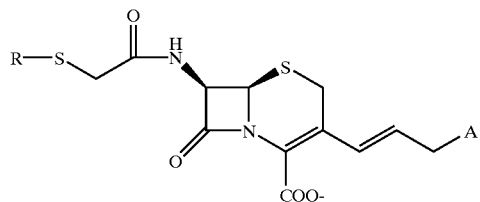
| Example No | R | A | MS (ISP) (M + H+) | IR (Nujol) (cm$^{-1}$) |
|---|---|---|---|---|
| 61 | 3,5-dimethylphenyl-CH< | 1-methyl-DABCO | 529.4 | 1757, 1658, 1614, 1544 |
| 62 | 2-naphthyl-CH< | $-N^+(CH_3)_2CH_2CH_2CH_2OH$ | 542.3 | 1765, 1657, 1603 |
| 63 | benzothiazol-2-yl-CH< | $-N^+(CH_3)_2CH_2CH_2CH_2OH$ | 549.3 | 1769, 1672, 1605 |
| 64 | 2-naphthyl-CH< | methyl-DBU | 591.4 | 1769, 1677, 1618 |
| 65 | benzothiazol-2-yl-CH< | methyl-DBU | 598.4 | 1770, 1680, 1618 |
| 66 | 2-naphthyl-CH< | $-N^+(CH_3)_2CH(CH_2OH)_2$ | 558.4 | 1767, 1658, 1607 |
| 67 | benzothiazol-2-yl-CH< | $-N^+(CH_3)_2CH(CH_2OH)_2$ | 565.3 | 1761, 1672, 1598 |
| 68 | 2-naphthyl-CH< | $-N^+(CH_3)(CH_2CH_2OH)_2$ | 558.3 | 1761, 1669, 1588 |

-continued

| Example No | R | A | MS (ISP) (M + H⁺) | IR (Nujol) (cm⁻¹) |
|---|---|---|---|---|
| 69 | 3,5-dimethylphenyl-CH(CH₃)- | -N⁺(CH₃)(CH₂CH₂OH)₂ | 536.3 | 1769, 1667, 1602 |
| 70 | 2-naphthyl-CH(CH₃)- | 1,1-dimethyl-4-hydroxypiperidinium | 554.4 | 1767, 1659, 1609 |
| 71 | 3,5-dimethylphenyl-CH(CH₃)- | 1,1-dimethyl-4-hydroxypiperidinium | 532.3 | 1771, 1674, 1610 |
| 72 | 2-naphthyl-CH(CH₃)- | 1-methyl-4-(carbamoylmethyl)pyridinium | 575.2 | 1764, 1675, 1658, 1601 |
| 73 | 3,5-dimethylphenyl-CH(CH₃)- | 1-methyl-4-(carbamoylmethyl)pyridinium | 553.4 | 1765, 1685, 1655, 1603 |
| 74 | 2-naphthyl-CH(CH₃)- | -N⁺(CH₃)₂CH₂COOH | 542.4 | 1780, 1680, 1638, 1624, 1600 |
| 75 | 2-naphthyl-CH(CH₃)- | 1-methyl-4-(dimethylamino)pyridinium | 561.3 | 1767, 1649, 1605, 1570 |
| 76 | 2-naphthyl-CH(CH₃)- | 1-methyl-4-(carboxymethylthio)pyridinium | 608.2 | 1760, 1665, 1625, 1603 |

-continued

| Example No | R | A | MS (ISP) (M + H⁺) | IR (Nujol) (cm⁻¹) |
|---|---|---|---|---|
| 77 | 2-naphthylmethyl | 4-methyl-N-methylpyridinium | 532.3 | 1778, 1654, 1602 |
| 78 | 3,5-dimethylbenzyl | 1-methyl-4-pyridinium-CH₂-C(O)-NH-CH₂CH₂-OH | 597.4 | 1766, 1664, 1638, 1602 |
| 79 | 2-naphthylmethyl | (S)-trimethylammonio-CH(CH₂Ph)-C(O)-OH | 632.4 | 1769, 1667, 1630 |
| 80 | benzothiazol-2-ylmethyl | 1-methyl-4-pyridinium-CH₂-C(O)-NH-CH₂CH₂-O-CH₂CH₂-OH | 670.4 | 1765, 1658, 1645, 1600 |
| 81 | NC-CH=CH-CH(CH₃)- | trimethylammonio-CH₂-C(O)-NH₂ | 466.3 | 2210, 1773, 1696, 1682, 1659, 1610 |

The starting materials used above were prepared in the following way:

(a) To a solution of 30.6 g (0.06 mol) of (E)-(6R,7R)-3-(3-iodo-propenyl)-8-oxo-7-trimethylsilanylamino-5-thia-1-aza-bicyclo[4.2.0]oct-2-ene-4-carboxylic acid trimethylsilanyl ester in 0.22 l of dichloromethane was added at 0° over 5 min a solution of 16.8 g (0.15 mol) of 1,4-diazobicyclo[2.2.2]octane in 0.15 l of acetonitrile. The dark reaction mixture was stirred at 0° for 4 h and then, 0.15 l of 2-propanol were added over 3 min, a precipitate being formed. After stirring was continued for 0.5 h, the pecipitated material was filtered off, washed with 0.1 l of 2-propanol and dried. For purification, this material was dissolved in 0.5 l of water and the pH of the solution was adjusted to 2.5 by the addition of 47% aqueous hydroiodic acid. After stirring for 15 min at 20°, a brown precipitate was filtered off and the clear solution was concentrated in vacuo to a volume of 0.25 l. Upon addition of 1.8 l of 2-propanol a precipitate formed which was isolated by filtration. The crude product was dissolved again in 0.4 l of water, and, after removing insoluble material and concentration of the solution to a volume of 0.25 l, the product was precipitated by the addition of 1.5 l of 2-propanol to give 20.4 g of (E)-(6R,7R)-7-amino-3-[3-(4-aza-1-azonia-bicyclo[2,2,2]octan-1-yl)-propenyl]-8-oxo-5-thia-1-aza-bicyclo[4.2.0]oct-2-ene-2-carboxylic acid dihydroiodide as a pale-yellow solid.

MS (ISP): 332.2 (m−2HI+H⁺); IR (Nujol): 1781, 1709, 1631, 1579 cm⁻¹.

(b) By operating in an analogous manner to the procedure described in Examples 56–81(a), (E)-(6R,7R)-3-(3-iodo-propenyl)-8-oxo-7-trimethylsilanylamno-5-thia-1-aza-bicyclo[4.2.0]oct-2-ene-4-carboxylic acid trimethylsilanyl ester was reacted with 2,3,4,6,7,8,9,10-octahydro-pyrimido[1,2-a]azepine,
4-dimethylamino-pyridine, and with
4-methyl-pyridine,
  respectively, and by operating in an analogous an manner to the procedure described in Examples 23(a), with trimethylsilanylated
(S)-2-hydroxymethyl-1-methyl-pyrrolidine, 3-dimethylamino-1-propanol,
5-2-dimethylamino-1,3-propandiol,
(Bis-2-hydroxy-ethyl)-methyl-amine,
4-hydroxy-1-methyl-piperidine,
Dimethylamino-acetic acid
Pyridin-4-ylsulfanyl-acetic acid, 2-Pyridin-4-yl-acetamide,
N-(2-hydroxy-ethyl)-2-pyridin-4-yl-acetamide, and with
N-[2-(2-hydroxy-ethoxy)-ethyl]-2-pyridin-4-yl-acetamide, respectively, to give the following compounds as light-brown solids:

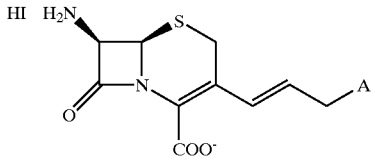

| Compound | A | MS (ISP) (M − HI + H⁺) | IR (Nujol) (cm⁻¹) |
|---|---|---|---|
| (E)-(6R,7R)-7-Amino-3-[3-(2,3,4,6,7,8,9,10-octahydro-pyrimido[1,2-a]azepin-1um-1-yl]-propenyl]-8-oxo-5-thia-1-aza-bicyclo[4.2.0]oct-2-ene-2-carboxylate monohydroiodide | | 334.2 | 1782, 1709, 1632, 1602, 1585, 1510 |
| (E)-(6R,7R)-7-Amino-3-[3-(4-dimethylamino-pyridin-1-ium-1-yl)-propenyl]-8-oxo-5-thia-1-aza-bicyclo[4.2.0]oct-2-ene-2-carboxylate monohydroiodide | | 376.3 | 1780, 1708, 1639 |
| (E)-(6R,7R)-7-Amino-3-[3-(4-methyl-pyridin-1-ium-1-yl)-propenyl]-8-oxo-5-thia-1-aza-bicyclo[4.2.0]oct-2-ene-2-carboxylate monohydroiodide | | 368.1 | 1783, 1710 1625, 1591, 1527, |
| (E)-(6R,7R)-7-Amino-3-[3-[(1R,2S- and [(1S, 2S)-2-hydroxymethyl-1-methyl-pyrrolidin-1-ium-1-yl]-propenyl]-8-oxo-5-thia-1-aza-bicyclo[4.2.0]oct-2-ene-2-carboxylate monohydroiodide | | 324.3 | 1781, 1708, 1638, 1589, |
| (E)-(6R,7R)-7-Amino-3-[3-[(3-hydroxy-propyl)-dimethyl-ammonio)-propenyl]-8-oxo-5-thia-1-aza-bicyclo[4.2.0]oct-2-ene-2-carboxylate monohydroiodide | | 340.3 | 1782, 1711, |
| (E)-(6R,7R)-7-Amino-3-[3-[(2-hydroxy-1-hydroxymethyl-ethyl)-dimethyl-ammonio]-propenyl]-8-oxo-5-thia-1-aza-bicyclo[4.2.0]oct-2-ene-2-carboxylate monohydroiodide | | 298.3 | 1774, 1719, 1681, 1632, 1582, 1536 |
| (E)-(6R,7R)-7-Amino-3-[3-[(bis-2-hydroxy-ethyl)-methyl-ammonio]-propenyl]-8-oxo-5-thia-1-aza-bicyclo[4.2.0]oct-2-ene-2-carboxylate monohydroiodide | | 341.2 | 1781, 1691, 1629, 1593 |
| (E)-(6R,7R)-7-Amino-3-[3-(cis- and -(trans-4-hydroxy-1-methyl-piperidin-1-ium-1-yl)-propenyl]-8-oxo-5-thia-1-aza-bicyclo[4.2.0]oct-2-ene-2-carboxylate monohydroiodide | | 357.3 | 1779, 1706, |
| (E)-(6R,7R)-7-Amino-3-[3-(carboxymethyl-dimethyl-ammonio)-propenyl]-8-oxo-5-thia-1-aza-bicyclo[4.2.0]oct-2-ene-2-carboxylate monohydroiodide | | 342.3 | 1782, 1628, 1528 |

-continued

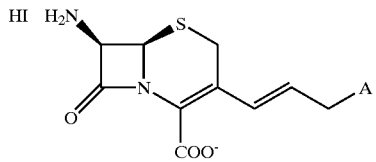

| Compound | A | MS (ISP) (M − HI + H⁺) | IR (Nujol) (cm⁻¹) |
|---|---|---|---|
| (E)-(6R,7R)-7-Amino-3-[3-(4-carboxymethylsulfanyl)-pyridin-1-ium-1-yl)-propenyl]-8-oxo-5-thia-1-aza-bicyclo(4.2.0)oct-2-ene-2-carboxylate monohydroiodide | | 408.2 | 1800, 1720, 1627, 1592 |
| (E)-(6R,7R)-7-Amino-3-[3-(4-carbamoylmethyl-pyridin-1-ium-1-yl)-propenyl]-8-oxo-5-thia-1-aza-bicyclo[4.2.0]oct-2-ene-2-carboxylate monohydroiodide | | 375.3 | 1801, 1676, 1639, 1574 |
| (E)-(6R,7R)-7-Amino-3-[3-[4-[N-(2-hydroxy-ethyl)-carbamoylmethyl]-pyridin-1-ium-1-yl]-propenyl]-8-oxo-5-thia-1-aza-bicyclo[4.2.0]oct-2-ene-2-carboxylate monohydroiodide | | 419.3 | 1801, 1639, 1543 |
| (E)-(6R,7R)-7-Amino-3-[3-[[(S)-1-carboxy-2-phenyl-ethyl]-dimethyl-ammonio]-propenyl]-8-oxo-5-thia-1-aza-bicyclo[4.2.0]oct-2-ene-2-carboxylate monohydroiodide | | 432.4 | 1786, 1628 |
| (E)-(6R,7R)-7-Amino-3-(3-[4-[N-[2-(2-hydroxy-ethoxyl-ethyl]-carbamoylmethyl]-pyridin-1-ium-1-yl]-propenyl]-8-oxo-5-thia-1-aza-bicyclo[4.2.0]oct-2-ene-2-carboxylate monohydroiodide | | 463.4 | 1802, 1640, 1543 |

EXAMPLE 82

By operating in an analogous manner to the procedure described in Example 2, (E)-(6R,7R)-7-(2-bromo-acetylamino)-8-oxo-3-(3-(quinolin-1-ium-1-yl-propenyl)-5-thia-1-aza-bicyclo[4.2.0]oct-2-ene-2-carboxylic acid bromide was reacted with 2,4,5-trichloro-benzenethiol to give (E)-(6R,7R)-7-[2-(2,4,5-trichloro-phenylsulfanyl)-acetylamino]-8-oxo-3-(3-(quinolin-1-ium-1-yl-propenyl)-5-thia-1-aza-bicyclo[4.2.0]oct-2-ene-2-carboxylate as a pale-yellow solid.

IR (Nujol): 1765, 1670, 1650, 1604 cm⁻¹; MS (ISP): 620.0 (M+H⁺($^{79}$Br)).

The starting material used above was prepared in the following way:
(a) By operating in an analogous manner to the procedure described in Example 2(a), (E)-(6R,7R)-7-amino-8-oxo-3-(3-quinolin-1-ium-1-yl-propenyl)-5-thia-1-aza-bicyclo[4.2.0]oct-2-ene-2-carboxylic acid chloride monohydrochloride was reacted with bromoacetyl bromide to give (E)-(6R,7R)-7-(2-bromo-acetylamino)-8-oxo-3-(3-quinulin-1-ium-1-yl-propenyl)-5-thia-1-aza-bicyclo[4.2.0]oct-2-ene-2-carboxylic acid bromide as a light-brown solid.
MS (ISP): 488.2 (M+H⁺($^{79}$Br)).

EXAMPLE 83–102

By operating in an analogous manner to the procedure described in Example 2, (E)-(6R,7R)-7-(2-bromo-acetylamino)-3-[3-(4-methyl-morpholin-4-ium-4-yl)-propenyl]-8-oxo-5-thia-1-aza-bicyclo[4.2.0]oct-2-ene-2-carboxylic acid bromide was reacted with benzooxazole-2-thiol,
2,4,5-trichloro-benzenethiol,
2-methoxy-benzenethiol,
3,5-dimethoxy-benzenethiol,
3-mercapto-benzoic acid,
4-mercapto-benzoic acid,
(2-mercapto-phenyl)-methanol
3,4-dimethoxy-benzenethiol,
2-phenoxy-benzenethiol,
4-acetylamino-benzenethiol,
4-(4-chlorophenoxy)-benzenethiol,
6-mercapto-naphththalene-2-carboxylic acid, and with
7-mercapto-4-methyl-chromen-2-one respectively, and (E)-(6R,7R)-7-(2-bromo-acetylamino)-3-[3-(carbamoylmethyl-dimethylammonio)-propenyl]-8-oxo-5-thia-1-aza-bicyclo[4.2.0]oct-2-ene-2-carboxylic acid bromide was reacted with
benzooxazole-2-thiol,
benzothiazole-2-thiol,
2,4,5-trichloro-benzenethiol,
6-mercapto-naphthalene-2-carboxylic acid,
7-mercapto-4-methyl-chromen-2-one,
benzothiazole-2-thiol, and with
rac-5-(4-mercapto-phenyl)-piperidin-2-one,
respectively, to give the following compounds as pale-yellow solids:

| Example No | R | A | MS (ISP) (M + H$^+$) | IR (Nujol) (cm$^{-1}$) |
|---|---|---|---|---|
| 83 | benzoxazol-2-ylmethyl | 4,4-dimethylmorpholin-4-ium-yl | 531.1 | 1769, 1677, 1606, 1559 |
| 84 | 2,4,5-trichlorophenylmethyl | 4,4-dimethylmorpholin-4-ium-yl | 592.0 ($^{35}$Cl) | 1762, 1672, 1644, 1598 |
| 85 | 2-methoxyphenylmethyl | 4,4-dimethylmorpholin-4-ium-yl | 520.2 | 1768, 1667, 1605 |
| 86 | 3,5-dimethoxyphenylmethyl | 4,4-dimethylmorpholin-4-ium-yl | 550.5 | 1769, 1672, 1603 |
| 87 | 3-carboxyphenylmethyl | 4,4-dimethylmorpholin-4-ium-yl | 534.2 | 1769, 1673, 1638, 1594 |
| 88 | 4-carboxyphenylmethyl | 4,4-dimethylmorpholin-4-ium-yl | 534.2 | 1769, 1677, 1633, 1593 |
| 89 | 2-(hydroxymethyl)phenylmethyl | 4,4-dimethylmorpholin-4-ium-yl | 520.2 | 1768, 1666, 1605 |

-continued

| Example No | R | A | MS (ISP) (M + H⁺) | IR (Nujol) (cm⁻¹) |
|---|---|---|---|---|
| 90 | 3,4-dimethoxyphenyl-CH₂- | N-methylmorpholinium | 549.3 | 1767, 1665, 1606 |
| 91 | 2-phenoxyphenyl-CH₂- | N-methylmorpholinium | 582.1 | 1765, 1672, 1602 |
| 92 | 4-acetamidophenyl-CH₂- | N-methylmorpholinium | 547.1 | 1766, 1672, 1591 |
| 93 | 4-(4-chlorophenoxy)phenyl-CH₂- | N-methylmorpholinium | 616.1 (³⁵Cl) | 1766, 1670, 1600 |
| 94 | 6-carboxynaphth-2-yl-CH₂- | N-methylmorpholinium | 584.4 | 1771, 1681, 1625, 1609 |
| 95 | 4-methyl-2-oxo-2H-chromen-7-yl-CH₂- | N-methylmorpholinium | 632.4 | |
| 96 | benzoxazol-2-yl-CH₂- | -N⁺(CH₃)₂CH₂C(O)NH₂ | 532.1 | 1768, 1692, 1631, 1601 |
| 97 | benzothiazol-2-yl-CH₂- | -N⁺(CH₃)₂CH₂C(O)NH₂ | 548.1 | 1767, 1691, 1631, 1602 |
| 98 | 2,4,5-trichlorophenyl-CH₂- | -N⁺(CH₃)₂CH₂C(O)NH₂ | 592.9 (³⁵Cl) | 1763, 1692, 1688, 1647, 1596 |

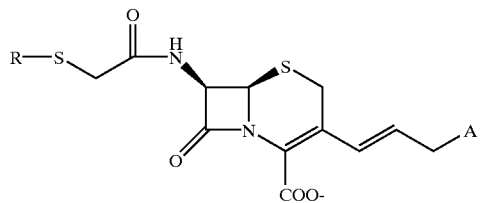

| Example No | R | A | MS (ISP) (M + H⁺) | IR (Nujol) (cm⁻¹) |
|---|---|---|---|---|
| 99 | HOOC-naphthyl- | -CH₂N⁺(CH₃)₂CH₂C(O)NH₂ | 585.4 | 1772, 1750, 1702, 1664, 1628, 1590 |
| 100 | 4-methyl-coumarin-7-yl | -CH₂N⁺(CH₃)₂CH₂C(O)NH₂ | 573.4 | 1758, 1712, 1683, 1648, 1598 |
| 101 | 2-methyl-benzothiazol-5-yl | -CH₂N⁺(CH₃)₂CH₂C(O)NH₂ | 562.2 | 1766, 1675, 1631, 1606 |
| 102 | 4-(2-oxo-piperidin-5-yl)phenyl | -CH₂N⁺(CH₃)₂CH₂C(O)NH₂ | 588.4 | 1766, 1689, 1637, 1601 |

The starting materials used above were prepared in the following way:
(a) By operating in an analogous manner to the procedure described in Example 2(a),
 (E)-(6R,7R)-7-amino-3-[3-(4-methyl-morpholin-4-ium-4-yl)-propenyl]-8-oxo-5-thia-1-aza-bicyclo[4.2.0]oct-2-ene-2-carboxylic acid chloride monohydrochloride, and
 (E)-(6R,7R)-7-3-[3-(carbamoylmethyl-dimethyl-ammonio)-propenyl]-8-oxo-8-thia-1-aza-bicyclo[4.2.0]oct-2-ene-2-carboxylic acid chloride monohydrochloride
 were reacted with bromoacetyl bromide, to give
(E)-(6R,7R)-7-(2-bromo-acetylamino)-3-[3-(4-methyl-morpholin-4-ium-4-yl)-propenyl]-8-oxo-5-thia-1-aza-bicyclo[4.2.0]oct-2-ene-2-carboxylic acid bromide,
MS (ISP): 460.1 (M−HBr+H⁺(⁷⁹Br)), and
(E)-(6R,7R)-7-(2-bromo-acetylamino)-3-[3-(carbamoylmethyl-dimethyl-ammonio)-propenyl]-8-oxo-5-thia-1-aza-bicyclo[4.2.0]oct-2-ene-2-carboxylic acid bromide,
MS (ISP): 461.1 (M−HBr+H+(⁷⁹Br)) respectively, as a light-brown solids.

EXAMPLES 103–104

By operating in an analogous manner to the procedure described in Example 2, but replacing triethylamine by an equimolar amount of 4-methyl-morpholine, (E)-(6R,7R)-7-(2-bromo- and (E)-(6R,7R)-7-(2-iodo-acetylamino)-3-[3-(4-carbamoylmethyl-1,4-diazonia-bicyclo[2.2.2]octan-4-yl)-propenyl]-8-oxo-5-thia-1-aza-bicyclo[4.2.0]oct-2-ene-2-carboxylate was reacted with benzothiazole-2-thiol, and with 3,5-dimethyl-benzenethiol, respectively. During the chromatographic purification on MCI gel CHP20P, elution was at first performed with 0.5% aqueous sodium chloride solution before a gradient of 0–30% aqueous acetonitrile was used. The product-containing fractions were concentrated in vacuo and freeze-dried, and the amorphous products obtained were triturated with ethyl acetate to give the following products as light-yellow solids:

(E)-(6R,7R)-3-[3-(4-carbamoylmethyl-1,4-diazonia-bicyclo[2.2.2]oct-4-yl)-propenyl]-7-[2-(naphthalen-2-ylsulfanyl)-acetylamino]-8-oxo-5-thia-1-aza-bicyclo[4.2.0]oct-2-ene-2-carboxylate chloride.
MS (ISP): 608.3 (M−Cl⁻)⁺.
(E)-(6R,7R)-3-[3-(4-carbamoylmethyl-1,4diazonia-bicyclo[2.2.2]octan-4-yl)-propenyl]-7-(2-[3,5-dimethyl-phenylsulfanyl)-acetylamino]-8-oxo-5-thia-1-aza-bicyclo[4.2.0]oct-2-ene-2-carboxylate chloride.
MS (ISP): 586.3 (M−Cl⁻)⁺.

The starting material used above was prepared in the following way:
(a) To an ice-cold solution of 1.12 g of 1,4-aza-bicyclo[2.2.2]octane in 10 ml of N,N-dimethylacetamide was added 1.85 g of 2-iodo-acetamide. The solution was stirred for 3 h at 20° and then, 0.15 l of ethyl acetate were added in portions. After the mixture had been stirred for 1 h, the crystals were isolated by filtration, washed thoroughly with 0.1 l of ethyl acetate and dried to give 2.9 g of 4-carbamoylmethyl-1-aza-4-azonia-bicyclo[2.2.2] octane iodide as white crystals.

NMR (DMSO-$d_6$): 3.06 (broad t, 6H); 3.51 (broad t, 6H); 3.97 (s, 2H); 7.70 (broad s, 1H); 7.90 (broad s, 1H) ppm.

(b) By operating in an analogous manner to the procedure described in Examples 23–25(a), 4-carbamoylmethyl-1-aza-4-azonia-bicyclo[2.2.2]octane iodide was silanylated with hexamethyldisilazane in acetonitrile and then reacted with (E)-(6R,7R)-3-(3-iodo-propenyl)-8-oxo-7-trimethylsilanylamno-5-thia-1-aza-bicyclo[4.2.0]oct-2-ene-4-carboxylic acid trimethylsilanyl ester to give (E)-(6R,7R)-7-amino-3-[3-(4-carbamoylmethyl-1,4-diazonia-bicyclo[2.2.2]octan-4-yl)-propenyl]-8-oxo-5-thia-1-aza-bicyclo[4.2.0]oct-2-ene-2-carboxylate iodide monohydroiodide as a light-yellow solid.

IR (Nujol): 1811, 1688, 1640, 1598 cm$^{-1}$; MS (ISP): 408.4 (M–HI–I$^-$)$^+$.

(c) To a suspension of 0.66 g (E)-(6R,7R)-7-amino-3-[3-(4-carbamoylmethyl-1,4-diazonia-bicyclo[2.2.2]octan-4-yl)-propenyl]-8-oxo-5-thia-1-aza-bicyclo[4.2.0]oct-2-ene-2-carboxylate iodide monohydroiodide in 8 ml of dichloromethane/acetonitrile (1:1) was added 1.3 ml of N,O-bis(trimethylsilanyl)trifluoroacetamide and the mixture was stirred at 20° for 1 h. After cooling of the reaction mixture to 0°, 0.35 ml of bromoacetyl bromide was added and stirring was continued for 30 min. The solution was dropped onto 0.15 l of diethyl ether containing 0.1 ml of water. The mixture was stirred for 0.5 h at 20° and subsequently, the precipitate was isolated by filtration, washed with 30 ml of diethyl ether, and dried. The brown solid was suspended in 10 ml of water. After adjusting the pH to 2.5 by the addition of 2N NaOH, 0.15 l of 2-propanol were added and the mixture was stirred at 20° for 0.5 h. The precipitate was filtered off, washed with 30 ml of diethyl ether and dried, to give 0.48 g of a mixture of (E)-(6R,7R)-7-(2-bromo- and (E)-(6R,7R)-7-(2-iodo-acetylamino)-3-[3-(4-carbamoylmethyl-1,4-diazonia-bicyclo[2.2.2]octan-4-yl)-propenyl]-8-oxo-5-thia-1-aza-bicyclo[4.2.0]oct-2-ene-2-carboxylate as a light-brown powder.

MS (ISP): 528.4 (M+H$^+$($^{79}$Br-product)), 576.2 (M+H$^+$(I-product)).

EXAMPLE 105

By operating in an analogous manner to the procedure described in Example 1, (E)-(6R,7R)-7-amino-3-[3-(carbamoylmethyl-dimethyl-ammonio)-propenyl]-8-oxo-8-thia-1-aza-bicyclo[4.2.0]oct-2-ene-2-carboxylic acid chloride monohydrochloride was acylated with (E)-[2,5-dichloro-4-(2-tert-butoxycarbonyl-vinyl)-phenylsulfanyl]-acetic acid to give after chromatographic purification of the crude reaction mixture on MCI gel CHP20P, using a gradient of 0–50% aqueous acetonitrile for elution, (6R,7R)-3-[3-((E)-carbamoylmethyl-dimethyl-ammonio)-propenyl]-7-[(E)-2-[2,5-dichloro-4-(2-tert-butoxycarbonyl-vinyl)-phenylsulfanyl]-acetylamino]-8-oxo-8-thia-1-aza-bicyclo [4.2.0]oct-2-ene-2-carboxylate as a pale-yellow. solid. A solution of 0.25 g of this material in 4 ml of dichloromethane/0.5 ml of anisole/2 ml of trifluoroacetic acid was stirred at 20° for 2 h. The solution was evaporated in vacuo and the oily residue was triturated with 50 ml of diethyl ether to give 0.24 g of (6R,7R)-3-[(E)-3-(carbamoylmethyl-dimethyl-ammonio)-propenyl]-7-[(E)-2-[4-(2-carboxy-vinyl)-2,5-dichloro-phenylsulfanyl)-acetylamino]-8-oxo-8-thia-1-aza-bicyclo[4.2.0]oct-2-ene-2-carboxylic acid monotrifluoroacetate as a pale-yellow solid.

IR (Nujol): 1776, 1695, 1632, 1575, 1544 cm$^{-1}$; MS (ISP): 629.2 (M–CF$_3$COOH+H$^+$($^{35}$Cl)).

EXAMPLES 106–108

By operating in an analogous manner to the procedure described in Example 105, (E)-(6R,7R)-7-amino-3-[3-(4-methyl-morpholin-4-ium-4-yl)-propenyl]-8-oxo-5-thia-1-aza-bicyclo[4.2.0]oct-2-ene-2-carboxylic acid chloride monohydrochloride, (E)-(6R,7R)-7-amino-3-[3-[(bis-2-hydroxy-ethyl)-methyl-ammonio]-propenyl]-8-oxo-5-thia-1-aza-bicyclo[4.2.0]oct-2-ene-2-carboxylate monohydroiodide, and (E)-(6R,7R)-7-amino-3-[3-(4-aza-1-azonia-bicyclo[2,2,2]oct-1-yl)-propenyl]-8-oxo-5-thia-1-aza-bicyclo[4.2.0]oct-2-ene-2-carboxylate dihydroiodide were acylated with with (E)-2-[2,5-dichloro-4-(2-tert-butoxycarbonyl-vinyl)-phenylsulfanyl)]-acetic acid to give, after cleavage of the tert-butyl ester, (6R,7R)-7-[(E)-2-[4-(2-carboxy-vinyl)-2,5-dichloro-phenylsulfanyl)-acetylamino]-3-[(E)-3-(4-methyl-morpholin-4-ium-4-yl)-propenyl]-8-oxo-5-thia-1-aza-bicyclo[4.2.0]oct-2-ene-2-carboxylic acid monotrifluoroacetate IR (Nujol): 1772, 1664, 1632, 1577 cm$^{-1}$; MS (ISP): 628.2 (M–CF$_3$COOH+H$^+$($^{35}$Cl));

(6R,7R)-3-[(E)-3-[(bis-2-hydroxy-ethyl)-methyl-ammonio]-propenyl]-7-[(E)-2-[4-(2-carboxy-vinyl)-2,5-dichloro-phenylsulfanyl)-acetylamino]- -8-oxo-5-thia-1-aza-bicyclo[4.2.0]oct-2-ene-2-carboxylic acid monotrifluoroacetate IR (Nujol): 1773, 1670, 1630, 1577 cm$^{-1}$; MS (ISP): 646.2 (M–CF$_3$COOH+H$^+$($^{35}$Cl));

and (6R,7R)-3-[(E)-3-(4-aza-1-azonia-bicyclo[2,2,2]oct-1-yl)-propenyl]-7-[(E)-2-[4-(2-carboxy-vinyl)-2,5-dichloro-phenylsulfanyl)-acetylamino]-8-oxo-5-thia-1-aza-bicyclo[4.2.0]oct-2-ene-2-carboxylic acid ditrifluoroacetate, IR (Nujol): 1773, 1670, 1630, 1577 cm$^{-1}$; MS (ISP): 639.2 (M–2CF$_3$COOH+H$^+$($^{35}$Cl)) respectively, as pale yellow solids.

EXAMPLE 109

By operating in an analogous manner to the procedure described in Example 105, (E)-(6R,7R)-7-amino-3-[3-(4-methyl-morpholin-4-ium-4-yl)-propenyl]-8-oxo-5-thia-1-aza-bicyclo[4.2.0]oct-2-ene-2-carboxylic acid chloride monohydrochloride, was acylated with (E)-(2-[4-[2-(tert-butoxycarbonylmethyl-carbamoyl)-vinyl]-2,5-dichloro-phenylsulfanyl]-acetic acid to give, after cleavage of the tert-butyl ester, (6R,7R)-7-[2-[4-[2-(E)-2-(carboxymethyl-carbamoyl)-vinyl]-2,5-dichloro-phenylsulfanyl]-acetylamino]-3-[(E)-3-(4-methyl-morpholin-4-ium-4-yl)-propenyl]-8-oxo-5-thia-1-aza-bicyclo[4.2.0]oct-2-ene-2-carboxylic acid trifluoroacetate as a pale-yellow solid.

IR (Nujol): 1772, 1721, 1658, 1630 cm$^{-1}$; MS (ISP): 685.2 (M–CF$_3$COOH+H$^+$; $^{35}$Cl).

EXAMPLE 110

By operating in an analogous manner to the procedure described in Example 105, (E)-(6R,7R)-7-amino-3-[3-(carbamoylmethyl-dimethyl-ammonio)-propenyl]-8-oxo-5-thia-1-aza-bicyclo[4.2.0]oct-2-ene-2-carboxylic acid chloride monohydrochloride was acylated with (E)-(2-[4-(2-tert-butoxycarbonyl-vinyl)-phenylsulfanyl]-acetic acid to give, after cleavage of the tert-butyl ester, (6R,7R)-3-[(E)-3-(carbamoylmethyl-dimethyl-ammonio)-propenyl]-7-[(E)-2-[4-(2-carboxy-vinyl)-phenylsulfanyl)-acetylamino]-8-oxo-8-thia-1-aza-bicyclo[4.2.0]oct-2-ene-2-carboxylic acid monotrifluoroacetate as a pale-yellow solid.

IR (Nujol): 1779, 1694, 1634, 1592 cm$^{-1}$; MS (ISP): 561.3 (M–CF$_3$COOH+H$^+$).

The starting material used above was prepared in the following way:

(a) A solution of 2.24 g of (4-formyl-phenylsulfanyl)-acetic acid ethyl ester and 4.72 g of (triphenylphosphoranylidene)-acetic acid tert-butyl ester in 50 ml of dichloromethane was kept at 20° for 15 h. The solvent was evaporated in vacuo and the remaining oil was chromatographed on silica gel using dichloromethane/hexane (1:1) as eluent to give 2.53 g of (E)-2-[4-(2-tert-butoxycarbonyl-vinyl)-phenylsulfanyl]-acetic acid ethyl ester as a colorless oil. To a solution of this material in 20 ml of tetrahydrofuran were added 8 ml of 2N aqueous sodium hydroxide, and the mixture was stirred for 2 h at 20°. The clear solution was diluted with 20 ml of ethyl acetate and then extracted with 30 ml of water. The aqueous layer was cooled with ice, acidified to pH 2.8 by the addition of 3N HCl, and the mixture was extracted with 60 ml of ethyl acetate. The organic layer was dried over sodium sulfate, evaporated in vacuo, and the residue was crystallized from ethyl acetate/hexane to give 1.78 g (E)-2-[4-(2-tert-butoxycarbonyl-vinyl)-phenylsulfanyl]-acetic acid as white crystals.

NMR (DMSO-d$_6$): 1.48 (s, 9H); 3.89 (s, 2H); 6.50 (d, 1H); 7.31 (d, 2H); 7.53 (d, 1H); 7.64 (d, 2H) ppm.

EXAMPLES 111–113

By operating in an analogous manner to the procedure described in Example 105, (E)-(6R,7R)-7-amino-3-[3-(4-tert-butoxycarbonylmethyl)-1,4-diazonia-bicyclo[2.2.2]oct-1-yl]-propenyl]-8-oxo-5-thia-1-aza-bicyclo[4.2.0]oct-2-ene-2-carboxylate iodide monohydroiodide was acylated with naphthalen-2-ylsulfanyl-acetic acid,
benzothiazol-2-ylsulfanyl-acetic acid, and with
(3,5-dimethyl-phenylsulfanyl)-acetic acid,
respectively, to give, after cleavage of the tert-butyl ester, the following compounds as pale-yellow solids:

| Example No | R | MS (ISP) | IR (Nujol) (cm$^{-1}$) |
|---|---|---|---|
| 111 | naphthalen-2-yl | 631.9 (M$^+$ + Na) | |
| 112 | benzothiazol-2-yl | | 1766, 1632, 1612 |
| 113 | 3,5-dimethyl-phenyl | 587.4 (M$^+$ + H) | 1767, 1633, 1610 |

The starting material used above was prepared in the following way:

(a) To an ice-cold solution of 5.61 g of 1,4-diaza-bicyclo[2.2.2]octane in 50 ml of N,N-dimethylacetamide were added 7.33 ml of tert-butyl 2-bromo-acetate. The solution was stirred for 4 h at 20° and then, 0.5 l of ethyl acetate and 0.3 l of diethyl ether were added. The precipitate formed was isolated by filtration, washed thoroughly with 0.5 l of ethyl acetate and dried to give 14.7 g of 1-tert-butoxycarbonylmethyl-4-aza-1-azonia-bicyclo[2.2.2]octane bromide as white crystals.

NMR (DMSO-d$_6$): 1.48 (s, 9H); 3.07 (broad t, 6H); 3.48 (broad t, 6H); 4.28 (s, 2H) ppm.

(b) By operating in an analogous manner to the procedure described in Examples 23–25(a), 1-tert-butoxycarbonylmethyl-4-aza-1-azonia-bicyclo[2.2.2]octane bromide was silanylated with hexamethyldisilazane in acetonitrile, and subsequently reacted with (E)-(6R,7R)-3-(3-iodo-propenyl)-8-oxo-7-trimethylsilanylamno-5-thia-1-aza-bicyclo[4.2.0]oct-2-ene-4-carboxylic acid trimethylsilanyl ester to give (E)-(6R,7R)-7-amino-3-[3-(4-tert-butoxycarbonylmethyl)-1,4-diazonia-bicyclo[2.2.2]octan-1-yl)-propenyl]-8-oxo-5-thia-1-aza-bicyclo[4.2.0]oct-2-ene-2-carboxylate iodide monohydroiodide as a light-yellow solid.

IR (Nujol): 1743, 1611 cm$^{-1}$.

EXAMPLES 114–117

By operating in an analogous manner to the procedure described in Example 1, (E)-(6R,7R)-7-amino-3-[3-[4-(4-morpholin-4-yl-butyl)-morpholin-4-ium-4-yl]-propenyl]-8-oxo-5-thia-1-aza-bicyclo[4.2.0]oct-2-ene-2-carboxylate dihydroiodide and (E)-(6R,7R)-7-amino-3-[3-[dimethyl-(4-dimethylamino-butyl)-ammonio]-propenyl]-8-oxo-5-thia-1-aza-bicyclo[4.2.0]oct-2-ene-2-carboxylate dihydroiodide were acylated with naphthalen-2-ylsulfanyl-acetic acid and with benzothiazol-2-ylsulfanyl-acetic acid, respectively, to give the following compounds as pale-yellow solids:

The starting materials used above were prepared in the following way:

(a) By operating in an analogous manner to the procedure described in Examples 56–81(a), (E)-(6R,7R)-3-(3-iodo-propenyl)-8-oxo-7-trimethylsilanylamino-5-thia-1-aza-bicyclo[4.2.0]oct-2-ene-4-carboxylic acid trimethylsilanyl ester was reacted with 4,4'-butane-1,4-diyl-bis-morpholine, and with N,N,N',N'-tetramethyl-1,4-butanediamine, respectively, to give (E)-(6R,7R)-7-amino-3-[3-[4-(4-morpholin-4-yl-butyl)-morpholin-4-ium-4-yl]-propenyl]-8-oxo-5-thia-1-aza-bicyclo[4.2.0]oct-2-ene-2-carboxylate dihydroiodide IR (Nujol): 1781, 1593, 1520 cm$^{-1}$; MS (ISP): 467.4 (M−2HI+H$^+$);

and (E)-(6R,7R)-7-amino-3-[3-[dimethyl-(4-dimethylamino-butyl)-ammonio]-propenyl]-8-oxo-5-thia-1-aza-bicyclo[4.2.0]oct-2-ene-2-carboxylate dihydroiodide IR (Nujol): 1782, 1596, 1520 cm$^{-1}$; MS (ISP): 383.4 (M−2HI+H$^+$) as light-brown solids.

EXAMPLE 118

By operating in an analogous manner to the procedure described in Example 1, (E)-(6R,7R)-7-amino-3-[3-[3-(3-tert-butoxycarbonylaminoacetoxy-propyl]-dimethyl-ammonio)-propenyl]-8-oxo-5-thia-1-aza-bicyclo[4.2.0]oct-

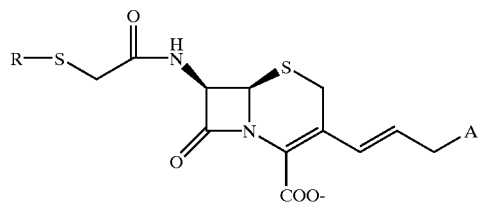

| Example No | R | A | MS (ISP) | IR (Nujol) (cm$^{-1}$) |
|---|---|---|---|---|
| 114 | naphthalen-2-ylmethyl | 4-(4-morpholinyl)butyl-N-methylmorpholinium | 667.5 | 1771, 1676, 1610 |
| 115 | benzothiazol-2-yl | 4-(4-morpholinyl)butyl-N-methylmorpholinium | 674.3 | 1770, 1679, 1610 |
| 116 | naphthalen-2-ylmethyl | trimethyl-(4-dimethylamino-butyl)ammonium | 583.4 | 1762, 1670, 1582 |
| 117 | benzothiazol-2-yl | trimethyl-(4-dimethylamino-butyl)ammonium | 590.4 | 1769, 1678, 1610 |

2-ene-2-carboxylate monohydroiodide was acylated with naphthalen-2-ylsulfanyl-acetic acid to give (E)-(6R,7R)-7-[2-(naphthalen-2-ylsulfanyl)-acetylamino]-3-[3-[-(3-tert-butoxycarbonylaminoacetoxy-propyl)-dimethyl-ammonio]-propenyl]-8-oxo-5-thia-1-aza-bicyclo[4.2.0]oct-2-ene-2-carboxylate. A solution of 40 mg of this material in 0.5 ml of trifluoroacetic acid was stirred at 0° for 20 min. The solvent was evaporated in vacuo and the residue was triturated for 1 h at 0 with 10 ml of a 0.4 N solution of hydrochloric acid in diethyl ether. The white solid was isolated by filtration, washed with 20 ml of diethyl ether and dried to give 34 mg of (E)-(6R,7R)-3-[3-[(3-aminoacetoxy-propyl)-dimethyl-ammonio)-propenyl]-7-[2-(naphthalen-2-ylsulfanyl)-acetylamino)-8-oxo-5-thia-1-aza-bicyclo[4.2.0]oct-2-ene-2-carboxylic acid chloride monohydrochloride as a white solid.

MS (ISP): 599.1 (M−2HCl+H$^+$).

The starting material used above was prepared in the following way:

(a) To an ice-cold solution of 6.2 g of 3-dimethylamino-1-propanol, 10.5 g of N-(tert-butoxycarbonyl)-glycine and 1.8 g of 4-dimethylamino-pyridine in 0.2 l of dichloromethane was added 13.8 g of N-(3-dimethylaminopropyl)-N'-ethylcarbodiimide monohydrochloride, and the reaction mixture was stirred for 4 h at 0°. The solvent was evaporated in vacuo and the remaining oil was subjected to column chromatography on silica gel, using ethyl acetate/acetone/triethylamine (5:5:1) as eluent, to give after evaporation of solvents 13.7 g of tert-butoxycarbonylamino-acetic acid 3-dimethylaminopropylester as a colorless oil.

NMR (CDCl$_3$): 1.45 (s, 9H); 1.82 (m, 2H); 2.22 (s, 6H); 2.34 (t, 2H); 3.90 (d, 2H); 4.20 (t, 2H); 5.30 (broad t, 1H) ppm.

(b) tert-Butoxycarbonylamino-acetic acid 3-dimethylaminopropyl ester was treated with hexamethyldisilazane and saccharin in acetonitrile, the resulting solution was reacted with (E)-(6R,7R)-3-(3-iodo-propenyl)-8-oxo-7-trimethylsilanylamino-5-thia-1-aza-bicyclo[4.2.0]oct-2-ene-4-carboxylic acid trimethylsilanyl ester in dichloromethane, and the product was precipitated by the addition of 2-propanol in an analogous manner to the procedure described in Examples 23–25(a). A solution of 5 g of crude reaction product in 20 ml of water showed pH 6.2. Upon addition of 50 ml of 2-propanol, a fine precipitate formed which was filtered off. The clear solution was concentrated in vacuo to a volume of 20 ml and then treated with stirring with 300 ml of 2-propanol. The precipitate was isolated by filtration and dried to give 1.0 g of (E)-(6R,7R)-7-amino-3-[3-(3-tert-butoxycarbonylaminoacetoxy-propyl]-dimethyl-ammonio]-propenyl]-8-oxo-5-thia-1-aza-bicyclo[4.2.0]oct-2-ene-2-carboxylate monohydrolodide as a light-brown solid.

IR (Nujol): 1755, 1697, 1598 cm$^{-1}$; MS (ISP): 499.4 (M−2HI+H$^+$).

EXAMPLES 119–122

By operating in an analogous manner to the procedure described in Example 118, (E)-(6R,7R)-7-amino-3-[3-[(3-tert-butoxycarbonylamino-propyl)-dimethyl-ammonio]-propenyl)-8-oxo-5-thia-1-aza-bicyclo[4.2.0]oct-2-ene-2-carboxylate monohydroiodide was acylated with naphthalen-2-ylsulfanyl-acetic acid and with benzothiazol-2-ylsulfanyl-acetic acid, respectively, and (E)-(6R,7R)-7-amino-3-[3-[[3-(tert-butoxycarbonyl-methyl-amino)-propyl]-dimethyl-ammonio]-propenyl]-8-oxo-5-thia-1-aza-bicyclo[4.2.0]oct-2-ene-2-carboxylate monohydroiodide, and (E)-(6R,7R)-7-amino-3-[3-[4-(3-tert-butoxycarbonylamino-propylcarbamoyl)-pyridin-1-ium-1-yl]-propenyl]-8-oxo-5-thia-1-aza-bicyclo[4.2.0]oct-2-ene-2-carboxylate monohydroiodide were acylateted with benzothiazol-2-ylsulfanyl-acetic acid. The resulting products were treated with trifluoroacetic acid and with 0.4 N solution of hydrochloric acid in diethyl ether to give the following products as white solids:

| Example No | R | A | MS (ISP) (M − 2HCl + H$^+$) |
|---|---|---|---|
| 119 | naphthalen-2-yl-CH- | -N$^+$(CH$_3$)$_2$-(CH$_2$)$_3$-NH$_2$ | 541.4 |
| 120 | benzothiazol-2-yl-CH- | -N$^+$(CH$_3$)$_2$-(CH$_2$)$_3$-NH$_2$ | 548.4 |

-continued

| Example No | R | A | MS (ISP) (M − 2HCl + H⁺) |
|---|---|---|---|
| 121 | benzothiazol-2-ylmethyl | -N⁺(CH₃)₂-CH₂CH₂CH₂-NH-CH₃ | 562.4 |
| 122 | benzothiazol-2-ylmethyl | 1-methylpyridinium-4-C(O)NH-CH₂CH₂CH₂-NH₂ | 625.4 |

The starting materials used above were prepared in the following way:

(a) N,N-Dimethyl-1,3-propanediamine, N,N,N'-trimethyl-1,3-propanediamine and 4-(3-tert-butoxycarbonylamino-propylcarbamoyl)-pyridine were treated with hexamethyldisilazane and saccharin in acetonitrile, the resulting solutions were each reacted with (E)-(6R,7R)-3-(3-iodo-propenyl)-8-oxo-7-trimethylsilanylamino-5-thia-1-aza-bicyclo[4.2.0]oct-2-ene-4-carboxylic acid trimethylsilanyl ester in dichloromethane, and the respective products were precipitated by the addition of 2-propanol, in an analogous manner to the procedure described in Examples 23–25(a). The crude reaction product were purified by precipitation from aqueous solution by the addition of 2-propanol at a pH between 5 and 7 in analogy to the procedure described in Example 118(a) to give (E)-(6R,7R)-7-amino-3-[3-[(3-tert-butoxycarbonylamino-propyl)-dimethyl-ammonio]-propenyl]-8-oxo-5-thia-1-aza-bicyclo[4.2.0]oct-2-ene-2-carboxylate monohydroiodide
MS (ISP): 441.4 (M–HI+H⁺);
and (E)-(6R,7R)-7-amino-3-[3-[[3-(tert-butoxycarbonyl-methyl-amino)-propyl]-dimethyl-ammonio]-propenyl]-8-oxo-5-thia-1-aza-bicyclo[4.2.0]oct-2-ene-2-carboxylate monohydroiodide,
MS (ISP): 455.3 (M–HI+H⁺);
and (E)-(6R,7R)-7-amino-3-[3-[4-(3-(tert-butoxycarbonylamino-propylcarbamoyl)-pyridin-1-ium-1-yl]-propenyl]-8-oxo-5-thia-1-aza-bicyclo[4.2.0]oct-2-ene-2-carboxylate monohydroiodide
MS (ISP): 518.5 (M–HI+H⁺),
respectively, as light-brown solids.

(b) To a solution of 10.2 g of N,N-dimethyl-1,3-propanediamine in 200 ml of 66% aqueous dioxane were added 24.1 g of dicarbonic acid bis-(1,1-dimethylethyl) ester and 50 ml of 2N aqueous sodium hydroxide solution. The mixture was stirred for 1 h at 20° and the clear solution was then partitioned between 300 ml of ethyl acetate and 200 ml of saturated sodium chloride solution. The organic layer was dried over sodium sulfate and evaporated in vacuo to give 12.4 g of crude N,N-dimethylamino-N'-tert-butoxycarbonyl-1,3-propanediamine as a colorless oil.
NMR (DMSO-d₆): 1.37 (s, 9H); 1.48 (m, 2H); 2.09 (s, 6H); 2.16 (t, 2H); 2.91 (m, 2H); 6.77 (broad t, 1H) ppm.

(c) N,N,N'-Trimethyl-1,3-propanediamine and N-(3-aminopropyl)-pyridine-4-carboxamide were subjected in an analogous manner to the procedure described above to give N'-tert-butoxycarbonyl-N,N,N'-trimethyl-1,3-propanediamine as a colorless oil,
and N-[3-tert-butoxycarbonylamino-propyl]-pyridine-4-carboxamide as white crystals.
NMR (DMSO-d₆): 1.37 (s, 9H); 1.63 (m, 2H); 2.97 (m, 2H); 3.26 (m, 2H); 6.83 (broad t, 1H); 7.73 (d, 2H); 8.72 (d, 2H); 8.78 (broad t, 1H) ppm.

EXAMPLE 123

To a stirred suspension of 122 mg of (E)-(6R,7R)-3-[3-[(3-amino-propyl)-dimethyl-ammonio]-propenyl]-7-[2-(naphthalen-2-ylsulfanyl)-acetylamino]-8-oxo-5-thia-1-aza-bicyclo[4.2.0]oct-2-ene-2-carboxylic acid chloride monohydrochloride in 2 ml of N,N-dimethylformamide were added at 20° over 1 h 3 portions of 52 mg of methanimidic acid phenylmethyl ester hydrochloride, with each portion being added simultaneously 0.04 ml of tetramethylguanidine. Stirring was continued for 1 h, and then, the reaction mixture was subjected to chromatographic purification on MCI gel CHP20P using a gradient of 0–30% aqueous acetonitrile for elution. The product-containing fractions were concentrated in vacuo and freeze-dried and the remaining amorphous material was triturated with 10 ml of a 0.4 N solution of hydrochloric acid in diethyl ether. The white solid was isolated by filtration, washed with 20 ml of diethyl ether and dried to give 53 mg of (E)-(6R,7R)-3-[3-[3-(formimidoylamino-propyl)-dimethyl-ammonio]-propenyl]-7-[2-(naphthalen-2-ylsulfanyl)-acetylamino]-8-oxo-5-thia-1-aza-bicyclo[4.2.0]oct-2-ene-2-carboxylic acid chloride monohydrochloride as a white solid.

MS (ISP): 568.4 (M−2HCl+H$^+$).

EXAMPLE 124

To a stirred suspension of 122 mg of (E)-(6R,7R)-3-[3-[(3-amino-propyl)-dimethyl-ammonio]-propenyl-7-[2-(naphthalen-2-ylsulfanyl)-acetylamino]-8-oxo-5-thia-1-aza-bicyclo[4.2.0]oct-2-ene-2-carboxylic acid chloride monohydrochloride in 2 ml of dimethylsulfoxide was added 60 mg of 1H-1,2,4-triazole-1-carboximidamide monohydrochloride followed by 0.05 ml of tetramethylguanidine. The mixture was stirred for 2 h at 20° and then subjected to chromatographic purification on MCI gel CHP20P using a gradient of 0–30% aqueous acetonitrile for elution. The product-containing fractions were concentrated in vacuo and freeze-dried, and the remaining amorphous material was triturated with 10 ml of a 0.4 N solution of hydrochloric acid in diethyl ether. The white solid was isolated by filtration, washed with 20 ml of diethyl ether and dried to give 48 mg of (E)-(6R,7R)-3-[3-[(3-guanidino-propyl)-dimethyl-ammonio]-propenyl]-7-[2-(naphthalen-2-ylsulfanyl)-acetylamino]-8-oxo-5-thia-1-aza-bicyclo[4.2.0]oct-2-ene-2-carboxylic acid chloride monohydrochloride as a white solid.

MS (ISP): 583.4 (M−2HCl+H$^+$).

EXAMPLES 125–126

By operating in an analogous manner to the procedure described in Example 123, (E)-(6R,7R)-7-[2-(benzothiazol-2-ylsulfanyl)-acetylamino]-3-[3-[dimethyl-(3-methylamino-propyl)-ammonio]-propenyl]-8-oxo-5-thia-1-aza-bicyclo[4.2.0]oct-2-ene-2-carboxylic acid chloride monohydrochloride, and (E)-(6R,7R)-3-[3-[4-(3-amino-propylcarbamoyl)-pyridin-1-ium-1-yl]-propenyl]-7-(2-(benzothiazol-2-ylsulfanyl)-acetylamino]-8-oxo-5-thia-1-aza-bicyclo[4.2.0]oct-2-ene-2-carboxylic acid chloride monohydrochloride were reacted with methanimidic acid phenylmethyl ester hydrochloride, to give (E)-(6R,7R)-7-[2-(benzothiazol-2-ylsulfanyl)-acetylamino]-3-[3-[[3-(formimidoyl-methyl-amino)-propyl]-dimethyl-ammonio]-propenyl]-8-oxo-5-thia-1-aza-bicyclo[4.2.0]oct-2-ene-2-carboxylic acid chloride monohydrochloride, MS (ISP): 589.4 (M−2HCl+H$^+$), and (E)-(6R,7R)-7-[2-(benzothiazol-2-ylsulfanyl)-acetylamino]-3-[3-[4-(3-formimidoylamino-propylcarbamoyl]-pyridin-1-ium-1-yl]-propenyl]-8-oxo-5-thia-1-aza-bicyclo[4.2.0]oct-2-ene-2-carboxylic acid chloride monohydrochloride, MS (ISP): 652.4 (M−2HCl+H$^+$), respectively, as white solids.

EXAMPLES 127–128

By operating in an analogous manner to the procedure described in Example 124, (E)-(6R,7R)-7-[2-(benzothiazol-2-ylsulfanyl)-acetylamino]-3-[3-[dimethyl-(3-methylamino-propyl)-ammonio]-propenyl]-8-oxo-5-thia-1-aza-bicyclo[4.2.0]oct-2-ene-2-carboxylic acid chloride monohydrochloride, and (E)-(6R,7R)-3-[3-[4-(3-amino-propylcarbamoyl)-pyridin-1-ium-1-yl]-propenyl]-7-[2-(benzothiazol-2-ylsulfanyl)-acetylamino]-8-oxo-5-thia-1-aza-bicyclo[4.2.0]oct-2-ene-2-carboxylic acid chloride monohydrochloride, were reacted with 1H-1,2,4-triazole-1-carboximidamide monohydrochloride, to give (E)-(6R,7R)-7-[2-(benzothiazol-2-ylsulfanyl)-acetylamino]-3-[3-[dimethyl-[3-(1-methyl-guanidino)-propyl]-ammonio]-propenyl]-8-oxo-5-thia-1-aza-bicyclo[4.2.0]oct-2-ene-2-carboxylic acid chloride monohydrochloride, MS (ISP): 604.4 (M−2HCl+H$^+$), and (E)-(6R,7R)-7-[2-(benzothiazol-2-ylsulfanyl)-acetylamino]-3-[3-[4-(3-guanidino-propylcarbamoyl)-pyridin-1-ium-1-yl]-propenyl]-8-oxo-5-thia-1-aza-bicyclo[4.2.0]oct-2-ene-2-carboxylic acid chloride monohydrochloride, MS (ISP): 667.4 (M−2HCl+H$^+$), respectively, as white solids.

EXAMPLES 129–134

By operating in an analogous manner to the procedure described in Example 2, but replacing triethylamine by an equimolar amount of 4-methylmorpholine, (E)-(6R,7R)-7-[(R)-2-bromo-propionylamino]-3-[3-(carbamoylmethyl-dimethyl-ammonio)-propenyl]-8-oxo-5-thia-1-aza-bicyclo[4.2.0]oct-2-ene-2-carboxylate was reacted with benzothiazole-2-thiol, 3,5-dimethyl-benzenethiol, 6-mercapto-naphthalen-2-carboxylic acid, and with 7-mercapto-4-methyl-chromen-2-one, respectively, and (E)-(6R,7R)-7-[(R)-2-bromo-propionylamino]-3-[3-(4-methyl-morpholin-4-ium-4-yl)-propenyl]-8-oxo-5-thia-1-aza-bicyclo[4.2.0]oct-2-ene-2-carboxylate was reacted with benzothiazole-2-thiol, and with 3,5-dimethyl-benzenethiol, respectively, to give the following compounds as pale-yellow solids:

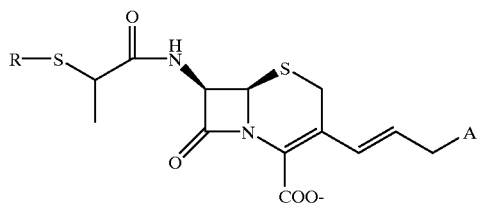

| Example No | R | A | MS (ISP) (M + H⁺) | IR (Nujol) (cm⁻¹) |
|---|---|---|---|---|
| 129 | benzothiazol-2-yl-methyl | trimethylammonio-acetamide | 562.3 | 1769, 1692, 1604 |
| 130 | 3,5-dimethylphenyl-methyl | trimethylammonio-acetamide | 533.4 | 1768, 1685, 1664, 1601 |
| 131 | 6-carboxynaphth-2-yl-methyl | trimethylammonio-acetamide | 599.4 | 1770, 1692, 1625, 1505 |
| 132 | 4-methyl-coumarin-7-yl-methyl | trimethylammonio-acetamide | 587.4 | 1769, 1690, 1602 |
| 133 | benzothiazol-2-yl-methyl | 4-methylmorpholin-4-ium-4-yl | 561.4 | 1769, 1674, 1609 |
| 134 | 3,5-dimethylphenyl-methyl | 4-methylmorpholin-4-ium-4-yl | 532.4 | 1769, 1670, 1608 |

The starting materials used above were prepared in the following way:

(a) (E)-(6R,7R)-3-(3-iodo-propenyl)-8-oxo-7-trimethylsilanylamino-5-thia-1-aza-bicyclo[4.2.0]oct-2-ene-4-carboxylic acid trimethylsilanyl ester was reacted in an analogous manner to the procedure described in Example 23–25(a), but replacing 4-hydroxy-piperidine by 2-dimethylamino-acetamide, or by 4-methyl-morpholine, to give the following compounds as light-brown solids:

(E)-(6R,7R)-7-amino-3-[3-(carbamoylmethyl-dimethyl-ammonio)-propenyl]-8-oxo-5-thia-1-aza-bicyclo[4.2.0]oct-2-ene-2-carboxylate monohydroiodide
MS (ISP): 341.2 (M−HI+H⁺);

(E)-(6R,7R)-7-amino-3-[3-(4-methyl-morpholin-4-ium-4-yl)-propenyl]-8-oxo-5-thia-1-aza-bicyclo[4.2.0]oct-2-ene-2-carboxylate monohydroiodide
MS (ISP): 340.3 (M−HI+H⁺).

(b) To a suspension of 1.4 g (E)-(6R,7R)-7-amino-3-[3-(carbamoylmethyl-dimethyl-ammonio)-propenyl]-8-oxo- 5-thia-1-aza-bicyclo[4.2.0]oct-2-ene-2-carboxylate monohydroiodide in 24 ml of dichloromethane/acetonitrile (1:1) was added 4 ml of N,O-Bis(trimethylsilanyl)trifluoroacetamide and the mixture was stirred at 20° for 0.5 h. After cooling of the reaction mixture to 0°, 2.05 g of (R)-2-bromo-propionyl chloride was added and stirring was continued for 5 min. The solution was dropped onto 0.5 l of diethyl ether containing 0.2 ml of water. The mixture was stirred for 0.5 h and subsequently, the precipitate was isolated by filtration, washed with 50 ml of diethyl ether, and dried. The brown solid was suspended in 5 ml of water. After adjusting the pH to 2.5 by the addition of 2N NaOH, 0.3 l of 2-propanol were added and the mixture was stirred at 20° for 0.5 h. The precipitate was filtered off, washed with 50 ml of diethyl ether and dried, to give 1.3 g of (E)-(6R,7R)-7-[(R)-2-bromo-propionylamino]-3-[3-(carbamoylmethyl-dimethyl-ammonio)-propenyl]-8-oxo-5-thia-1-aza-bicyclo[4.2.0]oct-2-ene-2-carboxylate as a light-brown powder.

NMR (D$_2$O): 1.66 (d,3H); 3.11 (s, 3H); 3.12 (s, 3H); 3.56 (dd, 2H); 3.91 (s, 2H); 4.10 (d, 2H); 4.47 (q, 1H); 5.08 (d, 1H); 5.50 (d, 1H); 5.83 (m, 1H); 6.83 (d, 1H) ppm. MS (ISP): 475.1 (M+H$^+$($^{79}$Br)).

(c) (E)-(6R,7R)-7-amino-3-[3-(4-methyl-morpholin-4-ium-4-yl)-propenyl]-8-oxo-5-thia-1-aza-bicyclo[4.2.0]oct-2-ene-2-carboxylate monohydroiodide was subjected in an analogous manner to the procedure described above to give (E)-(6R,7R)-7-((R)-2-bromo-propionylamino)-3-[3-(4-methyl-morpholin-4-ium-4-yl)-propenyl]-8-oxo-5-thia-1-aza-bicyclo[4.2.0]oct-2-ene-2-carboxylate as a light-yellow solid.

MS (ISP): 474.2 (M+H$^+$($^{79}$Br)).

The following example illustrates pharmaceutical preparations containing the cephalosporin derivatives provided by the present invention:

EXAMPLE A

Production of dry ampoules for intramuscular administration:

A lyophilisate of 1 g of propenyl cephalosporin is prepared in the usual manner and filled into an ampoule. The sterile water ampoule contains 10% propylene glycol. Prior to the administration, the lyophilisate is treated with 2.5 ml or 2% aqueous lidocaine hydrochloride solution.

As active ingredient can be used one of the end products prepared according to the above Examples.

EXAMPLE B

Production of dry ampoules for parenteral administration:

A sample of 0.25–8 g of propenyl-cephalosporin derivative optionally in admixture with 0.25–8 g of carbapenem antibiotic or 0.25–8 g of β-lactamase inhibitor is prepared in a usual manner and filled into an ampoule as a) a dry powder (crystalline, amorphous or lyophilisate powder) of propenyl cephalosporin derivate, optionally in admixture with a dry powder of carbapenem antibiotic or β-lactamase inhibitor; or b) a lyophilisate of the solution of propenyl cephalosporin derivative, optionally mixed with a lyophilisate of a solution of the carbapenem antibiotic or of the β-lactamase inhibitor.

The dry powder (crystalline, amorphous or lyophilized powder) of the propenyl cephalosporin derivate, optionally in combination with carbapenem antibiotic or β-lactamase inhibitor, can be filled in separate ampoules and mixed prior to the administration.

EXAMPLE C

Interlocking gelatine capsules each containing the following ingredients are manufactured in the usual manner:

| | |
|---|---|
| Readily hydrolyzable ester of propenyl cephalosporin of formula I | 500 mg |
| Luviskol (water-soluble polyvinylpyrrolidone) | 20 mg |
| Mannitol | 20 mg |
| Talc | 15 mg |
| Magnesium stearate | 2 mg |
| | 557 mg |

What is claimed is:
1. A compound having the formula

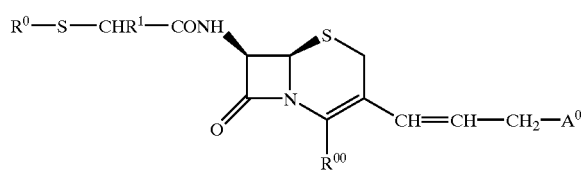

wherein
R$^{00}$ represents COOH when A$^0$ has no net positive charge and represents COO$^-$ when A$^0$ has a net positive charge;

R$^o$ is an organic residue with a molecular weight not exceeding 400 and is taken from the group consisting of lower alkyl, lower alkenyl, lower alkyl substituted by one or more substituent(s) R$^7$ and lower alkenyl substituted by one or more substituent(s) R$^7$, wherein R$^7$ is taken from the group consisting of halogen, lower cycloalkyl, naphthyl, phenyl or heterocyclyl, lower alkoxy- cyano-, hydroxy-, carbamoyl-, or one to three halogen-substituted phenyl or hydroxy-, halogen-, lower alkoxy-, carboxy-, amino-, lower alkyl amino-, di lower alkyl amino-, cyano-, or oxo-substituted heterocycyl, the subgroup of lower alkanoyl and lower cycloalkanoyl and benzoyl, any one of which is unsubstituted or hydroxy-, lower alkoxy-, amino-, lower alkyl amino-, di lower alky amino-, carbamoyl-, carbamoyloxy-, cyano-, phenyl-, or one to three halogen-substituted, hydroxy, acylated hydroxy, the subgroup of lower alkoxy and phenoxy and lower cycloalkoxy any one of which is unsubstituted or amino-, hydroxy-, methoxy-, carbamoyloxy-, carboxy-, carbamoyl-, or one to three halogen-substituted, amino, acylated amino, (lower alkyl)amino, (di-lower alkyl) amino, lower cycloalkylamino, carboxy, esterified carboxy, the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, carboxy-, carbamoyl-, carbamoyloxy-, or one to three halogen-substituted, the subgroup of lower alkylthio and lower cycloalkylthio and phenylthio and lower alkyl amino sulfonyl and cycloalkyl amino sulfonyl any one of which is unsubstituted or amino-, lower alkyl amino-, dilower alkyl amino-, hydroxy-, carboxy-, carbamoyl-, carbamoyloxy-, or one to three halogen-substituted, lower alkylsulfinyl, phenylsulfinyl, lower alkylsulfonyl, phenylsulfonyl, cyano, amidino, (lower alkyl)amidino, (di-lower alkyl)amidino, guanidino, (lower alkyl)guanidino, (di-lower alkyl)guanidino; or is taken from the group consisting of phenyl, naphthyl, heterocyclyl, phenyl substituted by one or more substituents $R^8$, naphthyl substituted by one or more substituents $R^8$, and heterocyclyl substituted by one or more substituents $R^8$, wherein $R^8$ is taken from the group consisting of halogen, the subgroup of lower alkyl and lower alkenyl and lower cycloalkyl any one of which is unsubstituted or is hydroxy-, lower alkoxy-, cyano-, carboxy-, amino-, lower alkyl amino-, di lower alkyl amino-, carbamoyl-, carbamoyl-oxy-, or one to three halogen-substituted, unsubstituted phenyl or heterocyclyl, lower alkoxycyano-, hydroxy-, carbamoyl-, or one to three halogen-substituted phenyl or hydroxy-, halogen-, lower alkoxy-, carboxy-, amino-, lower alkyl amino-, di lower alkyl amino-, cyano-, or oxo-substituted heterocycyl, the subgroup of lower alkanoyl and lower cycloalkanoyl and benzoyl, any one of which is unsubstituted or hydroxy-, lower alkoxy-, amino-, lower alkyl amino-, di lower alkyl amino-, carbamoyl-, carbamoyloxy-, cyano-, phenyl- or one to three halogen-substituted, hydroxy, the subgroup of lower alkoxy and phenoxy and lower cycloalkoxy any one of which is unsubstituted or amino-, hydroxy-, methoxy-, carbamoyloxy-, carboxy-, carbamoyl-, or one to three halogen-substituted, acylated hydroxy, amino, acylated amino, (lower alkyl)amino, (di-lower alkyl)amino, lower cycloalkylamino, carboxy, esterified carboxy or the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, methoxy, carboxy-, carbamoyl-, carbamoyloxy-, or one to three halogen-substituted, the subgroup of lower alkylthio and lower cycloalkylthio and phenylthio and lower alkyl amino sulfonyl and cycloalkyl amino sulfonyl any one of which is unsubstituted or amino-, lower alkyl amino-, dilower alkyl amino-, hydroxy-, methoxy-, carboxy-, carbamoyl-, carbamoyloxy-, or one to three halogen-substituted, lower alkylsulfinyl, phenylsulfinyl, sulfonyl, lower alkylsulfonyl, phenylsulfonyl, and cyano;

$A^o$ is a quaternary nitrogen residue substituted by an organic residue with a molecular weight not exceeding 400 of the formula

wherein $R^2$, $R^3$ and $R^4$ may be the same or different and each are taken from the group consisting of alkyl, substituted alkyl, cycloalkyl, alkenylalkyl, saturated heterocyclyl and saturated heterocyclyl substituted by one or more substituents $R^8$; or $R^2$ and $R^3$ together with the N atom represent a ring taken from the group consisting of saturated 5 to 8 membered heterocyclic rings, partly unsaturated 5 to 8 membered heterocyclic rings, saturated fused 10 to 14 membered heterocycic rings, partly unsaturated fused 10 to 14 membered heterocyclic rings and said heterocyclic rings substituted by one or more substituents $R^8$, said ring having one or more hetero atoms, $R^4$ being as above or may represent a 1-2-, 1-3-or 1-4-alkylene or vinylene bridge to the heterocyclic ring represented by $R^2$ and $R^3$; or $R^2$, $R^3$ and $R^4$ together with the N atom represent a ring taken from the group consisting of aromatic 5 and 6 membered heterocyclic rings, aromatic 10 to 12 membered fused heterocyclic rings and said heterocyclic rings substituted by one or more substituents $R^8$, said ring having one or more hetero atoms; or $A^o$ is a secondary or tertiary nitrogen residue substituted by an organic residue with a molecular weight not exceeding 400 of the general formula

IV

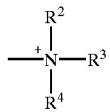

wherein $R^5$ and $R^6$ may be the same or different and each are taken from the group consisting of unsubstituted alkyl, hydroxy-, lower alkoxy-, cyano-, carboxy-, amino-, lower alkyl amino-, di lower alkyl amino-, carbamoyl-, or one to three halogen-substituted alkyl, cycloalkyl, alkenylalkyl, heterocyclyl, and heterocyclyl substituted by one or more substituents $R^8$, or $R^5$ is hydrogen; or $R^5$ and $R^6$ together with the N atom represent a ring taken from the group consisting of 5 and 6 membered heterocyclic rings, 10 to 12 membered fused heterocyclic rings and any of said heterocyclic rings substituted by one or more substituents $R^8$, said ring having one or more hetero atoms, and wherein, where $R^2$, $R^3$, $R^4$, $R^5$ or $R^6$ represent substituted alkyl the substituent of the alkyl group is carbamoyloxy or one or more substituents $R^7$; as well as esters thereof which are readily hydrolyzable in vivo, pharmaceutically acceptable salts of said compound and hydrates of the compound and of their esters and salts.

2. The compound according to claim 1, wherein the —CH═CH— moiety depicted in the formula through which substituent $A^0$ is attached to the 3-substituent of the cephalosporin ring is in the E-form.

3. A compound of the formula

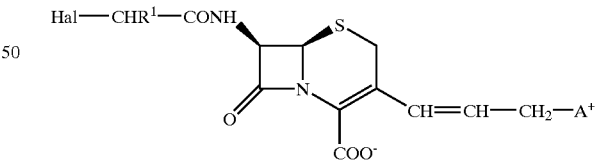

or

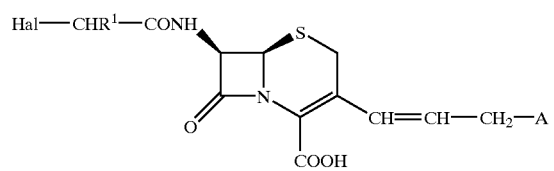

in which $R^1$ is hydrogen, lower alkyl, or phenyl; Hal is halogen; A+ is a quaternary nitrogen residue substituted by an organic residue with a molecular weight not exceeding 400 of the formula

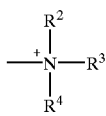

wherein $R^2$, $R^3$ and $R^4$ may be the same or different and each are taken from the group consisting of alkyl, substituted alkyl, cycloalkyl, alkenylalkyl, saturated heterocyclyl and saturated heterocyclyl substituted by one or more substituents; or $R^2$ and $R^3$ together with the N atom represent a ring taken from the group consisting of saturated 5 to 8 membered heterocyclic rings, partly unsaturated 5 to 8 membered heterocyclic rings, saturated fused 10 to 14 membered heterocyclic rings, partly unsaturated fused 10 to 14 membered heterocyclic rings and said heterocyclic rings substituted by one or more substituents $R^8$, said ring having one or more hetero atoms, $R^4$ being as above or may represent a 1-2-, 1-3- or 1-4-alkylene or vinylene bridge to the heterocyclic ring represented by $R^2$ and $R^3$; or $R^2$, $R^3$ and $R^4$ together with the N atom represent a ring taken from the group consisting of aromatic 5 and 6 membered heterocyclic rings, aromatic 10 to 12 membered fused heterocyclic rings and said heterocyclic rings substituted by one or more substituents $R^8$, said ring having one or more hetero atoms; and A is a secondary or tertiary nitrogen residue substituted by an organic residue with a molecular weight not exceeding 400 of the general formula

IV

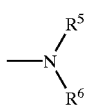

wherein $R^5$ and $R^6$ may be the same or different and each are taken from the group consisting of unsubstituted alkyl, hydroxy-, lower alkoxy-, cyano-, carboxy-, amino-, lower alkyl amino-, di lower alkyl amino-, carbamoyl-, or one to three halogen-substituted alkyl, cycloalkyl, alkenylalkyl, heterocyclyl, and heterocyclyl substituted by one or more substituents $R^8$, or $R^5$ is hydrogen; or $R^5$ and $R^6$ together with the N atom represent a ring taken from the group consisting of 5 and 6 membered heterocyclic rings, 10 to 12 membered fused heterocyclic rings and any of said heterocyclic rings substituted by one, or more substituents $R^8$, said ring having one or more hetero atoms, and wherein, where $R^2$, $R^3$, $R^4$, $R^5$ or $R^6$ represent substituted alkyl, the substituent of the alkyl group is carbamoyloxy or one or more substituents $R^7$; and esters and salts thereof;

wherein $R^7$ is taken from the group consisting of halogen, lower cycloalkyl, naphthyl, phenyl or heterocyclyl, lower alkoxy- cyano-, hydroxy-, carbamoyl-, or one to three halogen-substituted phenyl or hydroxy-, halogen,- lower alkoxy-, carboxy-, amino-, lower alkyl amino-, di lower alkyl amino-, cyano-, or oxo- substituted heterocycyl, the subgroup of lower alkanoyl and lower cycloalkanoyl and benzoyl, any one of which is unsubstituted or hydroxy-, lower alkoxy-, amino-, lower alkyl amino-, di lower alky amino-, carbamoyl-, carbamoyloxy-, cyano-, phenyl-, or one to three halogen-substituted, hydroxy, acylated hydroxy, the subgroup of lower alkoxy and phenoxy and lower cycloalkoxy any one of which is unsubstituted or amino-, hydroxy-, methoxy-, carbamoyloxy-, carboxy-, carbamoyl-, or one to three halogen-substituted, amino, acylated amino, (lower alkyl)amino, (di-lower alkyl) amino, lower cycloalkylamino, carboxy, esterified carboxy, the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, methoxy, carboxy-, carbamoyl-, carbamoyloxy-, or one to three halogen-substituted, the subgroup of lower alkylthio and lower cycloalkylthio and phenylthio and lower alkyl amino sulfonyl and cycloalkyl amino sulfonyl any one of which is unsubstituted or amino-, lower alkyl amino-, dilower alkyl amino-, hydroxy-, methoxy-, carboxy-, carbamoyl-, carbamoyloxy-, or one to three halogen-substituted, lower alkylsulfinyl, phenylsulfinyl, lower alkylsulfonyl, phenylsulfonyl, cyano, amidino, (lower alkyl)amidino, (di-lower alkyl) amidino, guanidino, (lower alkyl)guanidino, (di-lower alkyl)guanidino; and wherein $R^8$ is taken from the group consisting of halogen, the subgroup of lower alkyl and lower alkenyl and lower cycloalkyl any one of which is unsubstituted or is hydroxy-, lower alkoxy-, cyano-, carboxy-, amino-, lower alkyl amino-, di lower alkyl amino-, carbamoyl-, carbamoyl-oxy-, or one to three halogen-substituted, unsubstituted phenyl or heterocyclyl, lower alkoxy- cyano-, hydroxy-, carbamoyl-, or one to three halogen-substituted phenyl or hydroxy-, halogen-, lower alkoxy-, carboxy-, amino-, lower alkyl amino-, di lower alkyl amino-, cyano-, or oxo-substituted heterocycyl, the subgroup of lower alkanoyl and lower cycloalkanoyl and benzoyl, any one of which is unsubstituted or hydroxy-, lower alkoxy-, amino-, lower alkyl amino-, di lower alkyl amino-, carbamoyl-, carbamoyloxy-, cyano-, phenyl- or one to three halogen-substituted, hydroxy, the subgroup of lower alkoxy and phenoxy and lower cycloalkoxy any one of which is unsubstituted or amino-, hydroxy-, methoxy-, carbamoyloxy-, carboxy-, carbamoyl-, or one to three halogen-substituted, acylated hydroxy, amino, acylated amino, (lower alkyl)amino, (di-lower alkyl)amino, lower cycloalkylamino, carboxy, esterified carboxy or the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, methoxy, carboxy-, carbamoyl-, carbamoyloxy, or one to three halogen-substituted, the subgroup of lower alkylthio and lower cycloalkylthio and phenylthio and lower alkyl amino sulfonyl and cycloalkyl amino sulfonyl any one of which is unsubstituted or amino-, lower alkyl amino-, dilower alkyl amino-, hydroxy-, methoxy-, carboxy-, carbamoyl-, carbamoyloxy-, or one to three halogen-substituted, lower alkylsulfinyl, phenylsulfinyl, sulfonyl, lower alkylsulfonyl, phenylsulfonyl, and cyano.

4. A compound of the formula

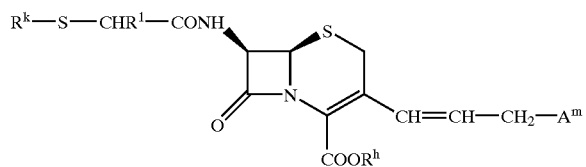

in which $R^1$ is hydrogen, lower alkyl, or phenyl; $R^h$ represents a negative charge when $A^m$ has a net positive charge or a carboxy protecting group when $A^m$ has no net positive charge; $R^k$ is an organic residue with a molecular weight not exceeding 400 and is taken from the group consisting of lower alkyl, lower alkenyl, lower alkyl substituted by one or more substituent(s) $R^7$ and lower alkenyl substituted by one or more substituent(s) $R^7$, wherein $R^7$ is taken from the group consisting of halogen, lower cycloalkyl, naphthyl, phenyl or heterocyclyl, lower alkoxy- cyano-, hydroxy-, carbamoyl-, or one to three halogen-substituted phenyl or hydroxy-, halogen,- lower alkoxy-, carboxy-, amino-, lower alkyl amino-, di lower alkyl amino-, cyano-, or oxo-substituted heterocycyl, the subgroup of lower alkanoyl and lower cycloalkanoyl and benzoyl, any one of which is unsubstituted or hydroxy-, lower alkoxy-, amino-, lower alkyl amino-, di lower alky amino-, carbamoyl-, carbamoyloxy-, cyano-, phenyl-, or one to three halogen-substituted, hydroxy, acylated hydroxy, the subgroup of lower alkoxy and phenoxy and lower cycloalkoxy any one of which is unsubstituted or amino-, hydroxy-, methoxy-, carbamoyloxy-, carboxy-,carbamoyl-, or one to three halogen-substituted, amino, acylated amino, (lower alkyl) amino, (di-lower alkyl)amino, lower cycloalkylamino, carboxy, esterified carboxy, the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, carboxy-, carbamoyl-, carbamoyloxy-, or one to three halogen-substituted, the subgroup of lower alkylthio and lower cycloalkylthio and phenylthio and lower alkyl amino sulfonyl and cycloalkyl amino sulfonyl any one of which is unsubstituted or amino-, lower alkyl amino-, dilower alkyl amino-, hydroxy-, methoxy-, carboxy-, carbamoyl-, carbamoyloxy-, or one to three halogen-substituted, lower alkylsulfinyl, phenylsulfinyl, lower alkylsulfonyl, phenylsulfonyl, cyano, amidino, (lower alkyl)amidino, (di-lower alkyl)amidino, guanidino, (lower alkyl)guanidino, (di-lower alkyl)guanidino; or is taken from the group consisting of phenyl, naphthyl, heterocyclyl, phenyl substituted by one or more substituents $R^8$, naphthyl substituted by one or more substituents $R^8$, and heterocyclyl substituted by one or more substituents $R^8$, wherein $R^8$ is taken from the group consisting of halogen, the subgroup of lower alkyl and lower alkenyl and lower cycloalkyl any one of which is unsubstituted or is hydroxy-, lower alkoxy-, cyano-, carboxy-, amino-, lower alkyl amino-, di lower alkyl amino-, carbamoyl-, carbamoyl-oxy-, or one to three halogen-substituted, unsubstituted phenyl or heterocyclyl, lower alkoxy-cyano-, hydroxy-, carbamoyl-, or one to three halogen-substituted phenyl or hydroxy-, halogen-, lower alkoxy-, carboxy-, amino-, lower alkyl amino-, di lower alkyl amino-, cyano-, or oxo-substituted heterocycyl, the subgroup of lower alkanoyl and lower cycloalkanoyl and benzoyl, any one of which is unsubstituted or hydroxy-, lower alkoxy-, amino-, lower alkyl amino-, di lower alkyl amino-, carbamoyl-, carbamoyloxy-, cyano-, phenyl- or one to three halogen-substituted, hydroxy, the subgroup of lower alkoxy and phenoxy and lower cycloalkoxy any one of which is unsubstituted or amino-, hydroxy-, methoxy-, carbamoyloxy-, carboxy-, carbamoyl-, or one to three halogen-substituted, acylated hydroxy, amino, acylated amino, (lower alkyl)amino, (di-lower alkyl)amino, lower cycloalkylamino, carboxy, esterified carboxy or the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, carboxy-, carbamoyl-, carbamoyloxy-, or one to three halogen-substituted, the subgroup of lower alkylthio and lower cycloalkylthio and phenylthio and lower alkyl amino sulfonyl and cycloalkyl amino sulfonyl any one of which is unsubstituted or amino-, lower alkyl amino-, dilower alkyl amino-, hydroxy-, methoxy-, carboxy-, carbamoyl-, carbamoyloxy-, or one to three halogen-substituted, lower alkylsulfinyl, phenylsulfinyl, sulfonyl, lower alkylsulfonyl, phenylsulfonyl, and cyano;

$A^m$ is a quaternary nitrogen residue substituted by an organic residue with a molecular weight not exceeding 400 of the formula

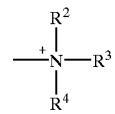

wherein $R^2$, $R^3$ and $R^4$ may be the same or different and each are taken from the group consisting of unsubstituted alkyl, hydroxy-, lower alkoxy-, cyano-, carboxy-, amino-, lower alkyl amino-, di lower alkyl amino-, carbamoyl-, or one to three halogen-substituted alkyl, cycloalkyl, alkenylalkyl, saturated heterocyclyl and saturated heterocyclyl substituted by one or more substituents $R^8$; or $R^2$ and $R^3$ together with the N atom represent a ring taken from the group consisting of saturated 5 to 8 membered heterocyclic rings, partly unsaturated 5 to 8 membered heterocyclic rings, saturated fused 10 to 14 membered heterocyclic rings, partly unsaturated fused 10 to 14 membered heterocyclic rings and said heterocyclic rings substituted by one or more substituents $R^8$, said ring having one or more hetero atoms, $R^4$ being as above or may represent a 1-2-, 1-3- or 1-4-alkylene or vinylene bridge to the heterocyclic ring represented by $R^2$ and $R^3$; or $R^2$, $R^3$ and $R^4$ together with the N atom represent a ring taken from the group consisting of aromatic 5 and 6 membered heterocyclic rings, aromatic 10 to 12 membered fused heterocyclic rings and said heterocyclic rings substituted by one or more substituents $R^8$, said ring having one or more hetero atoms; or $A^m$ is s secondary or tertiary nitrogen residue substituted by an organic residue with a molecular weight not exceeding 400 of the general formula

IV

wherein $R^5$ and $R^6$ may be the same or different and each are taken from the group consisting of unsubstituted alkyl, hydroxy-, lower alkoxy-, cyano-, carboxy-, amino, lower alkyl amino-, di lower alkyl amino-, carbamoyl-, or one to three halogen-substituted alkyl, cycloalkyl, alkenylalkyl, heterocyclyl, and heterocyclyl substituted by one or more substituents $R^8$, or $R^5$ is hydrogen; or $R^5$ and $R^6$ together with the N atom represent a ring taken from the group consisting of 5 and 6 membered heterocyclic rings, 10 to 12 membered fused heterocyclic rings and any of said heterocyclic rings substituted by one or more substituents $R^8$, said ring having one or more hetero atoms, and wherein, where $R^2$, $R^3$, $R^4$, $R^5$ or $R^6$ represent substituted alkyl, the substituent of the alkyl group is carbamoyloxy or one or more substituents $R^7$;

and in addition with the proviso that at least one of the following provisions is fulfilled:
(i) $R^h$ is a carboxylic acid protecting group,
(ii) $R^k$ includes therein, at least one of a protected amino group, a protected hydroxy group and a protected carboxylic group,
(iii) $A^m$ includes therein, at least one of a protected amino group, a protected hydroxy group and a protected carboxylic group.

5. The compound of claim 1 having the formula

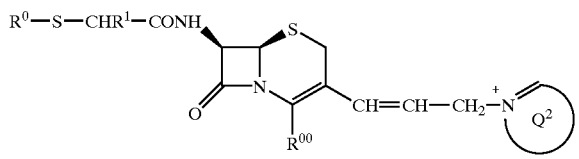

wherein $Q^2$ is taken from the group consisting of aromatic 5 or 6 membered heterocyclic rings, aromatic 10 to 12 membered fused heterocyclic rings and said heterocyclic rings substituted by $R^8$, as well as readily hydrolyzable esters thereof, pharmaceutically acceptable salts of said compound and hydrates of the compound and of their esters and salts.

6. The compound of claim 1 wherein $R^8$ is vinyl substituted by carbamoyl.

7. The compound of claim 1 wherein $A^o$ is a quaternary nitrogen of the formula

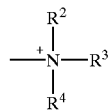

wherein $R^2$, $R^3$ and $R^4$ may be the same or different and each are taken from the group consisting of alkyl, alkyl substituted by $R^7$, cycloalkyl, alkenylalkyl, saturated heterocyclyl and heterocyclyl substituted by $R^8$, as well as esters thereof which are readily hydrolyzable in vivo, pharmaceutically acceptable salts of said compound and hydrates of the compound and of their esters and salts.

8. A compound which is (E)-(6R,7R)-7-[2-(benzothiazol-2-ylsulfanyl)-acetylamino]-8-oxo-3-[3-(1-carboxylatomethyl)-1,4-diazonia-bicyclo[2.2.2]octan-4-yl)-propenyl]-5-thia-1-aza-bicyclo[4.2.0]oct-2-ene-2-carboxylate.

9. The compound of claim 1 having the formula

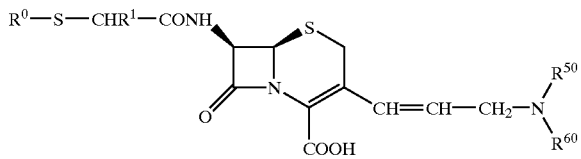

wherein $R^{50}$ and $R^{60}$ are the same or different and each are taken from the group consisting of alkyl, alkyl substituted by $R^7$, cycloalkyl, alkenylalkyl, saturated heterocyclyl and saturated heterocyclyl substituted by $R^8$, or $R^{50}$ is hydrogen;

as well as readily hydrolyzable esters thereof, pharmaceutically acceptable salts of said compound and hydrates of the compound and of their esters and salts.

10. The compound of claim 1 having the formula

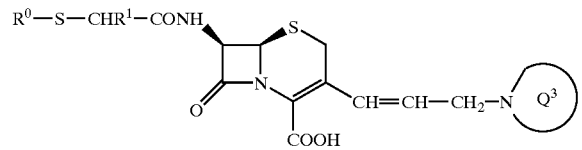

wherein $Q^3$ is taken from the group consisting of 5 and 6 membered heterocyclic rings, 5 and 6 membered fused heterocyclic rings, and said heterocyclic rings substituted by $R^8$, said ring having one or more hetero atoms, as well as readily hydrolyzable esters thereof, pharmaceutically acceptable salts of said compound and hydrates of the compound and of their esters and salts.

11. The compound according to claim 1, wherein when $R^8$ is a substituted lower alkyl, substituted lower alkenyl or substituted lower cycloalkyl, the substituent is taken from the group consisting of a hydroxy, lower alkoxy, cyano, carboxy, amino, lower alkylamino, di-(lower alkyl)amino, carbamoyl, carbamoyloxy and 1–3 halogens.

12. The compound according to claim 1, wherein $R^8$ is vinyl substituted by a substituent taken from the group consisting of cyano, carboxy, and the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, carboxy-, carbamoyl-, carbamoyloxy-, or one to three halogen-substituted.

13. The compound according to claim 1, wherein $R^8$ is taken from the group consisting of 2-carboxy-vinyl and 2-(carboxymethyl-carbamoyl)-vinyl.

14. The compound according to claim 11, wherein $R^8$ is a carbamoylmethyl group.

15. The compound according to claim 1, wherein $R^8$ is taken from the group consisting of hydroxyethylcarbamoylmethyl and hydroxyethoxyethylcarbamoylmethyl.

16. The compound according to claim 1, wherein substituted phenyl is phenyl substituted by a substituent taken from the group consisting of 1–3 halogens, lower alkoxy, cyano, hydroxy and carbamoyl.

17. The compound according to claim 1, wherein $R^7$ is heterocyclyl which is a 5 to 6 membered heterocyclic ring.

18. The compound according to claim 1, wherein $R^7$ is substituted heterocyclyl which is a 5 to 6 membered heterocyclic ring substituted by a substituent taken from the group consisting of hydroxy, halogen, lower alkoxy, carboxy, amino, lower alkylamino, di-(lower alkyl)amino, cyano and oxo.

19. The compound according to claim 1, wherein $R^8$ is a heterocyclyl which is a 5 or 6 membered heterocyclic ring.

20. The compound according to claim 1, wherein $R^8$ is a substituted heterocyclyl which is a 5 to 6 membered heterocyclic ring substituted by a substituent taken from the group consisting of hydroxy, halogen, lower alkoxy, carboxy, amino, lower alkylamino, di-(lower alkyl)amino, cyano and oxo.

21. The compound according to claim 1, wherein $R^7$ is taken from the group consisting of acyl and substituted acyl taken from the group consisting of lower alkanoyl, lower cycloalkanoyl, benzoyl and benzoyl substituted by a subtituent taken from the group consisting of 1–3 halogens, hydroxy, lower alkoxy, amino, lower alkylamino, di-(lower alkyl)amino, carbamoyl, carbamoyloxy, cyano and phenyl.

22. The compound according to claim 1, wherein $R^8$ is taken from the group consisting of acyl and substituted acyl taken from the group consisting of lower alkanoyl, lower cycloalkanoyl, benzoyl and benzoyl substituted by a substitutent taken from the group consisting of 1–3 halogens, hydroxy, lower alkoxy, amino, lower alkylamino, di-(lower alkyl)amino, carbamoyl, carbamoyloxy, cyano and phenyl.

23. The compound according to claim 1, wherein $R^7$ is taken from the group consisting of lower alkoxy, lower cycloalkoxy, phenoxy, substituted alkoxy, substituted lower cycloalkoxy and substituted phenoxy, where each $R^7$ which is a substituted group has a substituent taken from the group consisting of 1, 2 or 3 halogen atoms, amino, hydroxy, methoxy, carbamoyloxy, carboxy and carbamoyl.

24. The compound according to claim 1, wherein acylated hydroxy is taken from the group consisting of lower alkanoyloxy, benzoyloxy, heterocyclyl-carbonyloxy, lower alkoxycarbonyloxy, substituted alkanoyloxy, substituted benzoyloxy, substituted heterocyclylcarbonyloxy and substituted lower alkoxy carbonyloxy, wherein each acylated hydroxy which is a substituted group has a substituent taken from the group consisting of amino, (lower alkyl)amino, (di-lower alkyl)amino, methoxy, carboxy, carbamoyl, carbamoyloxy and 1, 2, and 3 halogen atoms.

25. The compound according to claim 1, wherein acylated amino is taken from the group consisting of lower alkanoylamino, lower cycloalkylamino, benzoylamino, heterocyclylcarbonylamino, lower alkoxycarbonylamino, substituted lower alkanoylamino, substituted lower cycloalkylamino, substituted benzoylamino, substituted heterocyclylcarbonylamino and substituted lower alkoxy carbonylamino, wherein each acylated amino which is a substituted group has a substituent taken from the group consisting of amino, (lower alkyl)amino, (di-lower alkyl) amino, hydroxy, methoxy, carboxy, carbamoyl, carbamoyloxy and 1, 2 and 3 halogen atoms.

26. The compound according to claim 1, wherein esterified carboxy is taken from the group consisting of lower alkoxycarbonyl, cycloalkoxycarbonyl, phenoxycarbonyl, phenyl-lower alkoxycarbonyl, substituted lower alkoxy carbonyl, substituted cycloalkylcarbonyl, substituted phenoxycarbonyl and substituted phenyl-lower alkoxycarbonyl, wherein each esterified carboxy which is a substituted group has a substituent taken from the group consisting of amino, (lower alkyl)amino, (di-lower alkyl) amino, methoxy, carboxy, carbamoyl, carbamoyloxy and 1, 2, and 3 halogen atoms.

27. A method for treating or preventing bacterial infection in a patient which comprises administering a compound of claim 1 to said patient.

28. The compound according to claim 1, wherein $R^8$ is taken from the group consisting of substituted lower alkylcarbamoyl and substituted lower cycloalkylcarbamoyl, wherein the substituent of each group is taken from the group consisting of hydroxy, lower alkoxy, hydroxy-lower alkoxy, amidino, (lower alkyl)-amidino, (di-lower alkyl) amidino, guanidino, (lower alkyl)guanidino, (di-lower alkyl)guanidino and heterocyclyl.

29. The compound according to claim 1, wherein $R^7$ is taken from the group consisting of lower alkylthio, lower cycloalkylthio, phenylthio, substituted lower alkylthio, substituted lower cyclo alkylthio and substituted phenylthio, wherein each $R^7$ which is a substituted group has a substituent taken from the group consisting of methoxy, amino, (lower alkyl)amino, (di-lower alkyl)amino, hydroxy, methoxy, carboxy, carbamoyl, carbamoyloxy and 1, 2 and 3 halogen atoms.

30. A compound of the formula

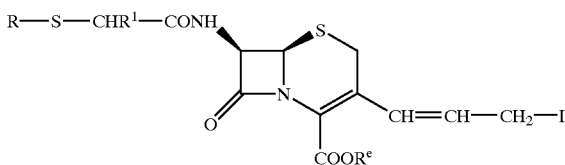

in which R is an organic residue with a molecular weight not exceeding 400 and is taken from the group consisting of lower alkyl, lower alkenyl, lower alkyl substituted by one or more substituent(s) $R^7$ and lower alkenyl substituted by one or more substituent(s) $R^7$, wherein $R^7$ is taken from the group consisting of halogen, lower cycloalkyl, naphthyl, phenyl or heterocyclyl, lower alkoxy- cyano-, hydroxy-, carbamoyl-, or one to three halogen-substituted phenyl or hydroxy-, halogen-, lower alkoxy-, carboxy-, amino-, lower alkyl amino-, di lower alkyl amino-, cyano-, or oxo-substituted heterocycyl, the subgroup of lower alkanoyl and lower cycloalkanoyl and benzoyl, any one of which is unsubstituted or hydroxy-, lower alkoxy-, amino-, lower alkyl amino-, di lower alky amino-, carbamoyl-, carbamoyloxy-, cyano-, phenyl-, or one to three halogen-substituted, hydroxy, acylated hydroxy, the subgroup of lower alkoxy and phenoxy and lower cycloalkoxy any one of which is unsubstituted or amino-, hydroxy-, methoxy-, carbamoyloxy-, carboxy-, carbamoyl-, or one to three halogen-substituted, amino, acylated amino, (lower alkyl) amino, (di-lower alkyl)amino, lower cycloalkylamino, carboxy, esterified carboxy, the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, carboxy-, carbamoyl-, carbamoyloxy-, or one to three halogen-substituted, the subgroup of lower alkylthio and lower cycloalkylthio and phenylthio and lower alkyl amino sulfonyl and cycloalkyl amino sulfonyl any one of which is unsubstituted or amino-, lower alkyl amino-, dilower alkyl amino-, hydroxy-, methoxy-, carboxy-, carbamoyl-, carbamoyloxy-, or one to three halogen-substituted, lower alkylsulfinyl, phenylsulfinyl, lower alkylsulfonyl, phenylsulfonyl, cyano, amidino, (lower alkyl)amidino, (di-lower alkyl)amidino, guanidino, (lower alkyl)guanidino, (di-lower alkyl)guanidino; or is taken from the group consisting of phenyl, naphthyl, heterocyclyl, phenyl substituted by one or more substituents $R^8$, naphthyl substituted by one or more substituents $R^8$, and heterocyclyl substituted by one or more substituents $R^8$, wherein $R^8$ is taken from the group consisting of halogen, the subgroup of lower alkyl and lower alkenyl and lower cycloalkyl any one of which is unsubstituted or is hydroxy-, lower alkoxy-, cyano-, carboxy-, amino-, lower alkyl amino-, di lower alkyl amino-, carbamoyl-, carbamoyl-, oxy-, or one to three halogen-substituted, unsubstituted phenyl or heterocyclyl, lower alkoxy-, cyano-, hydroxy-, carbamoyl-, or one to three halogen-substituted phenyl or hydroxy-, halogen-, lower alkoxy-, carboxy-, amino-, lower alkyl amino-, di lower alkyl amino-, cyano-, or oxo-substituted heterocycyl, the subgroup of lower alkanoyl and lower cycloalkanoyl and benzoyl, any one of which is unsubstituted or hydroxy-, lower alkoxy-, amino-, lower alkyl amino-, di lower alkyl amino-, carbamoyl-, carbamoyloxy-, cyano-, phenyl- or one to three halogen-substituted, hydroxy, the subgroup of lower alkoxy and phenoxy and lower cycloalkoxy any one of which is unsubstituted or amino-, hydroxy-, methoxy-, carbamoyloxy-, carboxy-, carbamoyl-, or one to three halogen-substituted, acylated hydroxy, amino, acylated amino, (lower alkyl)amino, (di-lower alkyl)amino, lower cycloalkylamino, carboxy, esterified carboxy or the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, carboxy-, carbamoyl-, carbamoyloxy-, or one to three halogen-substituted, the subgroup of lower alkylthio and lower cycloalkylthio and phenylthio and lower alkyl amino sulfonyl and cycloalkyl amino sulfonyl any one of which is unsubstituted or amino-, lower alkyl amino-, dilower alkyl amino-, hydroxy-, methoxy-, carboxy-, carbamoyl-, carbamoyloxy-, or one to three halogen-substituted, lower alkylsulfinyl, phenylsulfinyl, sulfonyl, lower alkylsulfonyl, phenylsulfonyl, and cyano;

$R^1$ is hydrogen, lower alkyl, or phenyl; and $R^e$ is a carboxy protecting group.

31. The compound according to claim 1, wherein $R^o$ is taken from the group consisting of phenyl and substituted phenyl.

32. The compound according to claim 31, wherein the substituted phenyl is taken from the group consisting of phenyl, 2,4,5-trichlorophenyl, 3,4-dichlorophenyl, 2,5-dichlorophenyl and 4-hydroxymethylphenyl.

33. The compound according to claim 31, wherein the substituted phenyl is 3,5-dimethylphenyl.

34. The compound according to claim 1, wherein $R^o$ is taken from the group consisting of naphthyl and substituted naphthyl.

35. The compound according to claim 34, wherein $R^o$ is taken from the group consisting of 2-naphthyl and 6-carboxy-2-naphthyl.

36. The compound according to claim 1, wherein $R^o$ is taken from the group consisting of heterocyclyl and substituted heterocyclyl.

37. The compound according to claim 36, wherein $R^o$ is taken from the group consisting of 2-benzooxazolyl, 2-benzothiazolyl and 4-pyridinyl.

38. A compound of claim 1 wherein $R^o$ is taken from the group consisting of lower alkyl substituted by one or more substituents $R^7$, lower alkenyl substituted by one or more substituents $R^7$, phenyl substituted by one or more substituents $R^8$, naphthyl substituted by one or more substituents $R^8$ and heterocyclyl substituted by one or more substituents $R^8$, wherein $R^8$ is taken from the group consisting of halogen, the subgroup of lower alkyl and lower alkenyl and lower cycloalkyl any one of which is unsubstituted or is hydroxy-, lower alkoxy-, cyano-, carboxy-, aminocarboxy-, lower alkyl amino carboxy-, di lower alkyl amino carboxy-carboxylated amino acid-, lower alkyl amino-, di lower alkyl amino-, carbamoyl-, carbamoyloxy-, or one to three halogen-substituted, unsubstituted phenyl, lower alkoxy-cyano-, hydroxy-, carbamoyl-, or one to three halogen-substituted phenyl, the subgroup of lower alkanoyl and lower cycloalkanoyl and benzoyl, any one of which is unsubstituted or hydroxy-, lower alkoxy-, amino-, lower alkyl amino-, di lower alky amino-, carbamoyl-, carbamoyloxy-, cyano-, or phenyl-substituted, hydroxy, the subgroup of lower alkoxy and phenoxy and lower cycloalkoxy any one of which is unsubstituted or amino-, hydroxy-, methoxy-, carbamoyloxy-, carboxy-, carbamoyl-, or one to three halogen-substituted, acylated hydroxy, amino, acylated amino, (lower alkyl)amino, (di-lower alkyl) amino, lower cycloalkylamino, carboxy, esterified carboxy or the subgroup of carbamoyl and lower alkyl carbamoyl and di lower alkyl carbamoyl and lower cycloalkyl carbamoyl each of which is unsubstituted or amino-, lower alkyl amino-, di lower alkyl amino-, carboxy-, carbamoyl-, carbamoyloxy-, or one to three halogen-substituted, the subgroup of lower alkylthio and lower cycloalkylthio and phenylthio and lower alkyl amino sulfonyl and cycloalkyl amino sulfonyl any one of which is unsubstituted or amino-, lower alkyl amino-, dilower alkyl amino-, hydroxy-, methoxy-, carboxy-, carbamoyl-, carbamoyloxy-, or one to three halogen-substituted, lower alkylsulfinyl, phenylsulfinyl, sulfonyl, guanidino, lower alkylsulfonyl, phenylsulfonyl, and cyano.

39. The compound according to claim 7, wherein $A^o$ is taken from the group consisting of trimethyl-ammonio and carbamoylmethyl-dimethyl-ammonio.

40. The compound according to claim 7, wherein $A^o$ is taken from the group consisting of dimethyl-(2-hydroxyethyl)-ammonio, (2-hydroxy-1-hydroxymethyl-ethyl)-dimethyl-ammonio and bis-(2-hydroxy-ethyl)-methyl-ammonio.

41. The compound of claim 1 having the formula

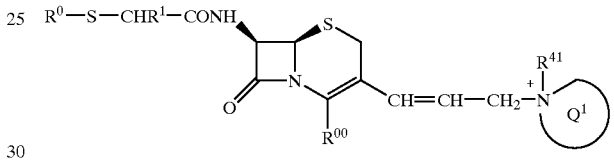

wherein $Q^1$ is a ring taken from the group consisting of saturated 5 to 8 membered heterocyclic rings, partly unsaturated 5 to 8 membered heterocyclic rings, saturated fused 10 to 14 membered heterocyclic rings, partly unsaturated fused 10 to 14 membered heterocyclic rings, and said heterocyclic rings substituted by $R^8$, said ring having one or more hetero atoms and $R^{41}$ is taken from the group consisting of alkyl, alkyl substituted by $R^7$, cycloalkyl, alkenylalkyl, saturated heterocyclyl, 1-2-, 1-3- and 1-4-alkylene bridges to the heterocyclic ring and 1-2-, 1-3- and 1-4-vinylene bridges to the heterocyclic ring, as well as readily hydrolyzable esters thereof, pharmaceutically acceptable salts of said compound and hydrates of the compound and of their esters and salts.

42. The compound according to claim 41 wherein $Q^1$ and the nitrogen by which it is attached form 1-methyl-pyrrolidin-1-ium or 4-methyl-morpholin-4-ium.

43. The compound according to claim 41, wherein $Q^1$ and the nitrogen by which it is attached form 4-aza-1-azonia-bicyclo[2,2,2]oct-1-yl or 1-azonia-bicyclo[2,2,2]oct-1-yl.

44. A composition comprising a compound according to claim 1, and a therapeutically inert carrier.

45. The compound according to claim 5, wherein $Q^2$ and the nitrogen by which it is attached form pyridin-1-ium, 2-methyl-pyridin-1-ium, 4-carbamoyl-pyridin-1-ium or quinolin-1-ium.

46. The compound according to claim 1, wherein the compound is taken from the group consisting of (E)-(6R,7R)-7-[2-(Benzothiazol-2-ylsulfanyl)-acetylamino]-8-oxo-3-(3pyridin-1-ium-1-yl-propenyl)-5-thia-1-aza-bicyclo[4.2.0]oct-2-ene-2-carboxylate, (E)-(6R,7R)-8-Oxo-3-(3-pyridin-1-ium-1-yl-propenyl)-7-[2-(2,4,5-trichlorophenyl-sulfanyl)-acetylamino]-5-thia-1-aza-bicyclo[4.2.0]oct-2-ene-2-carboxylate, (E)-(6R,7R)-3-[3-(3-Hydroxy-pyridin-1-ium-1-yl)-propenyl]-7-[2-(naphthalen-2-ylsulfanyl)- acetylamino]-8-oxo-5-thia-1-aza-bicyclo[4.2.0]oct-2-ene-2-carboxylate, (E)-(6R,7R)-7-[2-(Naphthalen-2-ylsulfanyl)-acetylamino]-8-oxo-3-(3-quinolin-1-ium-1-yl-propenyl)-5-thia-1-aza-bicyclo[4.2.0]oct-2-ene-2-carboxylate, (E)-(6R,7R)-3-[3-(1-Methyl-pyrrolidin-1-ium-1-yl)-propenyl]-7-[2-(naphtalen-2-ylsulfanyl)-acetylamino]-8-oxo-5-thia-1-aza-bicyclo[4.2.0]oct-2-ene-2-carboxylate, (E)-(6R,7R)-3-[3-(Carbamoylmethyl-dimethyl-ammonio)-propenyl]-7-[2-(naphthalen-2-ylsulfanyl)-acetylamino]-8-oxo-5-thia-1-aza-bicyclo[4.2.0]oct-2-ene-2-carboxylate, and (E)-(6R,7R)-7-[2-(Naphthalen-2-ylsulfanyl)-acetylamino]-8-oxo-3-[3-pyridin-1-ium-1-yl-propenyl]-5-thia-1-aza-bicyclo[4.2.0]oct-2-ene-2-carboxylate.

47. The compound according to claim 9, wherein $R^{50}$ and $R^{60}$ are both methyl or one is methyl and the other is cyclopropyl.

48. The compound according to claim 1, wherein the compound is taken from the group consisting of (E)-(6R,7R)-3-[3-[Dimethyl-(2-hydroxy-ethyl)-ammonio]-propenyl]-7-[2-(benzothiazol-2-ylsulfanyl)-acetylamino]-8-oxo-5-thia-1-aza-bicyclo[4.2.0]oct-2-ene-2-carboxylate, (E)-(6R,7R)-3-[3-(4-Aza-1-azonia-bicyclo[2,2,2]octan-1-yl)-propenyl]-7-[2-(naphthalen-2-ylsulfanyl)-acetylamino]-8-oxo-5-thia-1-aza-bicyclo[4.2.0]oct-2-ene-2-carboxylate, (E)-(6R,7R)-3-[3-[(3-Hydroxy-propyl)-dimethyl-ammonio]-propenyl]-7-[2-(naphthalen-2-ylsulfanyl)-acetylamino]-8-oxo-5-thia-1-aza-bicyclo[4.2.0]oct-2-ene-2-carboxylate, (E)-(6R,7R)-3-[3-[(2-Hydroxy-1-hydroxymethyl-ethyl)-dimethyl-ammonio]-propenyl]-2-[2-(naphthalen-2-ylsulfanyl)-acetylamino]-8-oxo-5-thia-1-aza-bicyclo[4.2.0]oct-2-ene-2-carboxylate, (E)-(6R,7R)-7-[2-(Benzothiazol-2-ylsulfanyl)-acetylamino]-8-oxo-3-[3-[(2-hydroxy-1-hydroxymethyl-ethyl)-dimethyl-ammonio]-propenyl]-5-thia-1-aza-bicyclo[4.2.0]oct-2-ene-2-carboxylate, (E)-(6R,7R)-3-[3-[Bis-(2-hydroxy-ethyl)-dimethyl-ammonio]-propenyl]-7-[2-(3,5-dimethyl-phenylsulfanyl)-acetylamino]-8-oxo-5-thia-1-aza-bicyclo[4.2.0]oct-2-ene-2-carboxylate, and (E)-(6R,7R)-3-[3-Carbamoylmethyl-dimethyl-ammonio]-propenyl]-7-[2-(6-carboxy-naphthalen-2-ylsulfanyl)-acetylamino]-8-oxo-5-thia-1-aza-bicyclo[4.2.0]oct-2-ene-2-carboxylate.

49. The compound according to claim 10, wherein $Q^3$ and the nitrogen by which it is attached form benzoimidazol-1-yl, pyrrolidin-1-yl or 4-hydroxy-piperidin-1-yl.

50. The compound according to claim 1, wherein the compound is taken from the group consisting of (E)-(6R,7R)-8-Oxo-7-(2-phenylsulfanyl-acetylamino)-3-(3-pyridin-1-ium-1-yl-propenyl)-5-thia-1-aza-bicyclo[4.2.0]oct-2-ene-2-carboxylate, (E)-(6R,7R)-7-[2-(5-Ethoxycarbonyl-4-methyl-thiazol-2-ylsulfanyl)-acetylamino]-8-oxo-3-(3-pyridin-1-ium-1-yl-propenyl)-5-thia-1-aza-bicyclo[4.2.0]oct-2-ene-2-carboxylate, (E)-(6R,7R)-3-[3-(2-Methyl-pyridin-1-ium-1-yl)-propenyl]-7-[2-(naphthalen-2-ylsulfanyl)-acetylamino]-8-oxo-5-thia-1-aza-bicyclo[4.2.0]oct-2-ene-2-carboxylate, (E)-(6R,7R)-3-[3-(2-methyl-pyridin-1-ium-1-yl)-propenyl]-8-oxo-7-(2-phenylsulfanyl-acetylamino)-5-thia-1-aza-bicyclo[4.2.0]oct-2-ene-2-carboxylate, (E)-(6R,7R)-3-[3-(3-Hydroxy-pyridin-1-ium-1-yl)-propenyl]-8-oxo-7-(2-phenylsulfanyl-acetylamino)-5-thia-1-aza-bicyclo[4.2.0]oct-2-ene-2-carboxylate, (E)-(6R,7R)-8-Oxo-7-[2-phenylsulfanyl)-acetylamino]-3-(3-quinolin-1-ium-1-yl-propenyl)-5-thia-1-aza-bicyclo[4.2.0]oct-2-ene-2-carboxylate, (E)-(6R,7R)-3-[3-(1-Methyl-pyrrolidin-1-ium-1-yl)-propenyl]-8-oxo-7-(2-phenylsulfanyl-acetylamino)-5-thia-1-aza-bicyclo[4.2.0]oct-2-ene-2-carboxylate, and (E)-(6R,7R)-7-[2-(Naphthalen-2-ylsulfanyl)-acetylamino]-8-oxo-3-(3-trimethylammonio-propenyl)-5-thia-1-aza-bicyclo[4.2.0]oct-2-ene-2-carboxylate.

51. The compound of claim 1 wherein $R^1$ is lower alkyl or phenyl.

* * * * *